United States Patent [19]
Griffin et al.

[11] Patent Number: 5,679,639
[45] Date of Patent: Oct. 21, 1997

[54] SERINE PROTEASE DERIVED-POLYPEPTIDES AND ANTI-PEPTIDE ANTIBODIES, SYSTEMS AND THERAPEUTIC METHODS FOR INHIBITING COAGULATION

[75] Inventors: John H. Griffin, Del Mar; Rolf M. Mesters, La Jolla, both of Calif.

[73] Assignee: The Scripps Research Institute, La Jolla, Calif.

[21] Appl. No.: 295,411

[22] Filed: Aug. 22, 1994

Related U.S. Application Data

[63] Continuation of Ser. No. 793,989, Nov. 18, 1991, abandoned.

[51] Int. Cl.$^6$ .............................. A61K 38/00; C07K 7/06; C07K 7/08
[52] U.S. Cl. .............................. 514/14; 514/15; 530/326; 530/328
[58] Field of Search .............................. 530/326, 328; 512/14–15

[56] References Cited

PUBLICATIONS

Kumar et al, *J. Biol. Chem*, vol. 266, No. 2, 15 Jan. 1991, pp. 915–921.
Haley, et al., *J. Biol. Chem*, vol. 264, No. 27, 25 Sep.
James et al, *Blood*, vol. 77, No. 2, (Jan. 15), 1991: pp. 317–323.
Esmon, et al, Proc. Natl. Acad. Sci, USA, vol. 78, No. 4, pp. 2249–2252, 1981.
Beckmann, et al., *Nucleic Acids Res.*, 13: 5233–5247 (1985).
Brown, et al., *Biochem. J.*, 101: 214–228 (1966).
Choo, et al., *Nature*, 299:178–180 (1982).
Degen, et al., *Biochemistry*, 22: 2087–2097 (1983).
Esmon, et al., *Ann. N.Y. Acad. Sci.*, 614: 30–43 (1991).
Foster, et al., *Proc. Natl. Acad. Sci. USA*, 82: 4673–4677 (1985).
Gruber, et al., *Blood*, 73: 639–642 (1989).
Hagen, et al., *Proc. Natl. Acad. Sci. USA*, 83: 2412–2416 (1986).
Haley, et al., *J. Biol. Chem.*, 264: 16303–16310 (1989).
Heeb, et al., *J. Biol. Chem.*, 265: 2365–2369 (1990).
James, et al., *Blood*, 77: 317–323 (1991).
Kisiel, et al., *J. Clin. Invest.*, 64: 761–769 (1979).
Krishnaswamy, et al., *J. Biol. Chem.*, 261: 9684–9693 (1986).
Kumar, et al., *J. Biol. Chem.*, 266: 915–921 (1991).
Leytus, et al., *Proc. Natl. Acad. Sci. USA*, 81: 3699–3702 (1984).
Marear, et al., *Blood*, 59: 1067–1072 (1982).
Mikes, et al, *Biochem. Biophys. Res. Comm.*, 24: 346–352 (1966).
Ohlin, et al., *Biochem*, 29: 644–651 (1990).
Plutzsky, et al., *Proc. Natl. Acad. Sci USA*, 83: 546–550 (1986).
Sadowski, et al., *J. Biol. Chem.*, 251: 2770–2776 (1976).
Seegers, et al., *Thrombosis Res.*, 13: 233–243 (1978).
Solymoss, et al., *J. Biol. Chem.*, 263: 14884–14890 (1988).
Sugo, et al., *J. Biol. Chem.*, 260: 10453–10457 (1985).
Suzuki, et al., *J. Biol. Chem.*, 258: 163–168 (1983).
Walker, et al., *J. Biol. Chem.*, 265: 1484–1489 (1990).

*Primary Examiner*—Cecilia J. Tsang
*Assistant Examiner*—S. G. Marshall
*Attorney, Agent, or Firm*—Thomas Fitting; Emily Holmes

[57] ABSTRACT

The present invention describes polypeptides and anti-peptide antibodies capable of inhibiting serine protease enzymatic activity. In particular, polypeptides and anti-peptide antibodies derived from the blood coagulation serine proteases Factor VIIa, Factor IXa, Factor Xa, Factor XIa, thrombin and plasma kallikrein are described that are capable of inhibiting coagulation. The polypeptide and antibody are useful in methods and systems for inhibiting serine proteases, and particularly for inhibiting blood coagulation processes mediated by serine proteases in vitro or in a human patient.

4 Claims, 4 Drawing Sheets

SERINE PROTEASE DERIVED-POLYPEPTIDES AND ANTI-PEPTIDE ANTIBODIES, SYSTEMS AND THERAPEUTIC METHODS FOR INHIBITING COAGULATION

CROSS-REFERENCE TO RELATED APPLICATION

This is a continuation of application Ser. No. 07/793,989, filed Nov. 18, 1991, now abandoned, the disclosures of which are incorporated by reference herein.

DESCRIPTION

This invention was made with the support of the United States Government, and the United States Government has certain rights in the invention pursuant to National Institutes of Health Contract HL-31950.

TECHNICAL FIELD

The present invention relates to polypeptides and anti-peptide antibodies useful for therapeutic methods and compositions for inhibiting coagulation.

BACKGROUND

Serine proteases are a class of proteins that proteolytically cleave other proteins. Members of this class of proteins contribute to important biological processes including the proteolytic cascade reactions of complement activation and blood coagulation.

Cleavage of a blood coagulation factor contributes to the coagulation cascade, resulting in blood coagulation. A variety of medical conditions can arise where it is advantageous to inhibit the coagulation cascade at the level of one or another proteolytic step. In addition, procedures involving blood product manipulation can activate members of the cascade, and therefore their specific inhibition is advantageous.

Protein C (PC) is a member of the class of vitamin K-dependent serine protease coagulation factors. Unlike the majority of coagulation factors, such as Factors VIIa, IXa, Xa, XIIa, thrombin, plasmin or plasma kallikrein which are procoagulants, Protein C regulates blood coagulation by acting as a natural anticoagulant that circulates in the blood in an inactive form that requires proteolytic activation to generate the anticoagulant enzyme. The activated form of Protein C, APC, inhibits blood coagulation at the levels of Factor V and VIII in the clotting cascade.

Similar to most other zymogens of extracellular proteases and the above recited blood coagulation factors, Protein C has the core structure of the chymotrypsin family having insertions and N-terminus extensions that enable regulation of the zymogen and the enzyme. See Owen W., in "Hemostasis and Thrombosis: Basic Principles and Clinical Practice", Colman et al., eds, pp. 235-241, J. B. Lippincott Co. (Philadelphia), 1987.

Protein C is composed of domains with discrete structure and function. See Foster et al., Proc. Natl. Acad. Sci. USA, 82:4673-4677 (1985) and Plutzky et al., Proc. Natl. Acad. Sci. USA, 83:546-550 (1986). The light chain contains an amino-terminal gamma-carboxyglutamic acid (Gla) region which is followed by two domains that are homologous to domains in the epidermal growth factor (EGF) precursor. The serine protease activity resides in the heavy chain. Ohlin et al., Biochem., 29:644-651 (1990).

The zymogen is activated by the action of thrombin at the site between the arginine residue at position number 12 and the leucine residue at position 13. See Kisiel, J. Clin. Invest., 64:761-769, (1976); Marlar et al., Blood, 59:1067-1072 (1982). Other proteins including Factor Xa (Haley et al., J. Biol. Chem., 264:16303-16310 (1989), Russell's viper venom and trypsin (Esmon et al., J. Biol. Chem., 251:2770-2776 (1976) have also been shown to enzymatically cleave inactive protein C to its activated form. Activated protein C hydrolyzes arginine esters and related substrates via a core triad of catalytic amino acid residues which occur at Ser-201, His-56, and Asp-102 of the heavy chain. The triad forms a hydrophobic substrate binding pocket. The enzyme's specificity is restricted to a small number of protein substrates; blood coagulation cofactors, activated Factors V and VIII, are the only known macromolecular substrates for the proteolytic inactivation by activated protein C. See Kisiel et al., Biochem., 16:5824-5831 (1977); Vehar et al., Biochem., 19:401-410 (1980); and Walker et al., Biochem. Biophys. Acta., 571:333-342 (1979).

Thrombin, the major physiological protein C activator, activates protein C slowly in purified systems, plasma, or blood, when in the presence of physiological concentrations of calcium. A membrane-bound thrombin receptor called thrombomodulin has been identified which accelerates protein C activation. Esmon et al., Proc. Natl. Acad. Sci. USA, 78:2249-2252 (1981). Liberated thrombin binds to thrombomodulin on the luminal surface of endothelial cells and undergoes an increase in specificity for circulating protein C. Calcium is required for this process and is bound to calcium-binding domains in the EGF-like regions of protein C. Additional studies have revealed that the membrane-lipid domain of protein C, the vitamin-K dependent Gla domain, is also required for activation of protein C. Esmon et al., in "Progress in Vascular Biology, Hemostasis, and Thrombosis", Ruggeri et al., eds., Annals of The New York Academy of Sciences, Vol. 614:30-43 (1991).

Inhibitors of members of the coagulation serine proteases have been described. For example, a region of Factor VIIa comprising residues 285 to 305 was reported to inhibit the Factor VIIa-tissue factor mediated conversion of Factor X to Factor Xa. Kumar et al, J. Biol. Chem., 266:915-921 (1991). In addition, a synthetic polypeptide corresponding to the region of prothrombin at residues 467 to 478 was reported to inhibit binding of thrombin to thrombomodulin and to inhibit thrombin induced clotting of fibrinogen. Suzuki et al, Blood, 77:317-323 (1991).

BRIEF DESCRIPTION OF THE INVENTION

Regions of the serine-protease domain of zymogen proteins have been identified that are involved in protein-protein interaction. The regions are shown to be located on the zymogen at a position away from the catalytic site of the zymogen. Polypeptides derived from any of the identified binding domain regions are shown to inhibit the proteolytic activity normally associated with the activated serine protease and therefore are useful for inhibiting proteolysis.

In addition, where a polypeptide is derived from a zymogen that participates in blood coagulation, it was found that the polypeptide inhibits coagulation in vivo and in vitro.

Thus, the present invention contemplates a variety of serine protease-derived polypeptides comprising no more than about 100 amino acid residues that have the capacity to inhibit coagulation and include an amino acid residue sequence that defines a serine protease binding domain essential for proteolytic activity.

In a related embodiment, the present invention contemplates an antibody comprising antibody molecules that inhibits coagulation and that immunoreacts with a polypeptide of this invention and immunoreacts with the serine protease from which the polypeptide was derived.

A method for inhibiting coagulation in a patient is also contemplated that comprises administering to said patient a coagulation-inhibiting amount of a coagulation inhibitor of this invention, namely a polypeptide or an anti-polypeptide antibody of this invention.

In addition, the invention contemplates an in vitro method for inhibiting coagulation in an aqueous composition with an coagulation-inhibiting amount of a polypeptide or anti-polypeptide antibody of this invention.

BRIEF DESCRIPTION OF THE DRAWINGS

In the drawings, forming a portion of this disclosure.

DETAILED DESCRIPTION OF THE INVENTION

A. Definitions

Figure 1:
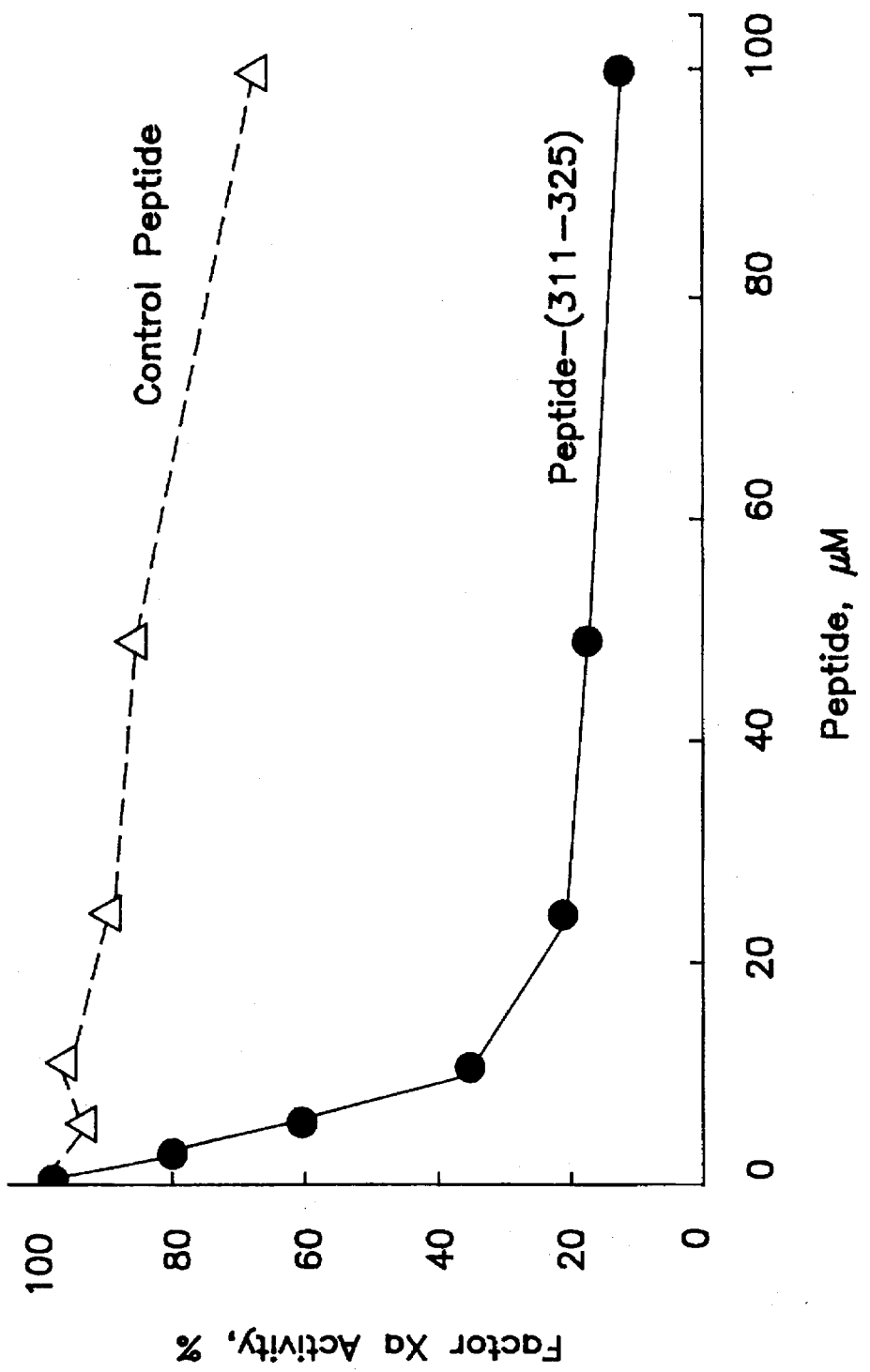
FIG. 1 illustrates factor Xa clotting activity in the presence of PC311-325. The assay was performed as described in Example 5a6). Solid circles with solid lines depict factor Xa activity of 0.15 nM factor Xa in the presence of PC311-325 and solid triangles with dashed lines depict factor Xa activity in the presence of the control peptide.

Amino Acid Residue: An amino acid formed upon chemical digestion (hydrolysis) of a polypeptide at its peptide linkages. The amino acid residues identified herein are preferably in the natural "L" isomeric form. However, residues in the "D" isomeric form can be substituted for any L-amino acid residue, as long as the desired functional property is retained by the polypeptide. $NH_2$ refers to the free amino group present at the amino terminus of a polypeptide. COOH refers to the free carboxy group present at the carboxy terminus of a polypeptide. In keeping with standard polypeptide nomenclature, *J. Biol. Chem.*, 243:3552–59 (1969) and adopted at 37 CFR §1.822(b)(2), abbreviations for amino acid residues are shown in the following Table of Correspondence:

| TABLE OF CORRESPONDENCE | | |
|---|---|---|
| SYMBOL | | |
| 1-Letter | 3-Letter | AMINO ACID |
| Y | Tyr | tyrosine |
| G | Gly | glycine |
| F | Phe | phenylalanine |
| M | Met | methionine |
| A | Ala | alanine |
| S | Ser | serine |
| I | Ile | isoleucine |
| L | Leu | leucine |
| T | Thr | threonine |
| V | Val | valine |
| P | Pro | proline |
| K | Lys | lysine |
| H | His | histidine |
| Q | Gln | glutamine |
| E | Glu | glutamic acid |
| W | Trp | tryptophan |
| R | Arg | arginine |
| D | Asp | aspartic acid |
| N | Asn | asparagine |
| C | Cys | cysteine |

It should be noted that all amino acid residue sequences are represented herein by formulae whose left and right orientation is in the conventional direction of amino-terminus to carboxy-terminus. In addition, the phrase "amino acid residue" is broadly defined to include modified and unusual amino acids, such as those listed in 37 CFR §1.822(b)(4), and are incorporated by reference. Furthermore, it should be noted that a dash at the beginning or end of an amino acid residue sequence indicates either a peptide bond to a further sequence of one or more amino acid residues or a covalent bond to a carboxyl or hydroxyl end group.

Activated Protein C: Activated Protein C refers to Protein C that is cleaved proteolytically by thrombin to yield an activated protein C (APC) which inactivates coagulation Factors Va and VIIIa thus inhibiting coagulation.

Activated Protein C Inhibitor: A PC polypeptide or anti-PC antibody or monoclonal antibody of this invention that inhibits APC in an APC activity assay.

Antibody: The term antibody in its various grammatical forms is used herein to refer to immunoglobulin molecules and immunologically active portions of immunoglobulin molecules, i.e., molecules that contain an antibody combining site or paratope. Exemplary antibody molecules are intact immunoglobulin molecules, substantially intact immunoglobulin molecules and portions of an immunoglobulin molecule, including those portions known in the art as Fab, Fab', F(ab')$_2$ and F(v).

Antibody Combining Site: An antibody combining site is that structural portion of an antibody molecule comprised of a heavy and light chain variable and hypervariable regions that specifically binds (immunoreacts with) an antigen. The term immunoreact in its various forms means specific binding between and antigenic determinant-containing molecule and a molecule containing an antibody combining site such as a whole antibody molecule or a portion thereof.

Anticoagulant: an agent that interrupts coagulation and thereby inhibits fibrin formation.

Coagulation: the sequential process in which the multiple coagulation factors of the blood interact resulting in the formation of fibrin.

Factor V: Factor V is a high molecular weight protein that, when activated by thrombin, can accelerate the conversion of prothrombin to thrombin by Factor Xa which promotes coagulation. Activated factor Va is inactivated by activated Protein C to inhibit the coagulation process.

Factor VIII: Factor VIII, also called the antihemophilic factor in blood coagulation, is a high molecular weight protein involved in the activation of Factor X in concert with Factor IXa. Activated Factor VIIIa is inactivated by activated Protein C to inhibit the coagulation process.

Factor IX: Factor IX is a zymogen of a serine protease which when activated functions in concert with Factor VIIIa to cause the conversion of Factor X to activated Factor X (Xa) which promotes coagulation.

Factor X: Factor X is a zymogen of a serine protease which when activated functions in concert with Factor Va to cause the conversion of prothrombin to thrombin which promotes coagulation.

Monoclonal Antibody: The phrase monoclonal antibody in its various grammatical forms refers to a population of antibody molecules that contains only one species of antibody combining site capable of immunoreacting with a particular antigen. A monoclonal antibody thus typically displays a single binding affinity for any antigen with which it immunoreacts. A monoclonal antibody may therefore contain an antibody molecule having a plurality of antibody combining sites, each immunospecific for a different antigen, e.g., a bispecific monoclonal antibody.

Polypeptide and Peptide: Polypeptide and peptide are terms used interchangeably herein to designate a linear series of amino acid residues connected one to the other by peptide bonds between the alpha-amino and carboxy groups of adjacent residues.

Protein C: Protein C (PC) is a vitamin K-dependent serine protease zymogen and is homologous with other known vitamin K-dependent serine proteases. In the presence of endothelial cell thrombomodulin and thrombin, Protein C is activated to a serine protease, APC, and becomes a potent inhibitor of blood coagulation by inactivating Factor Va and Factor VIIIa.

Protein S: Protein S (PS) is a vitamin K-dependent plasma protein which serves as a co-factor to activated Protein C in the inactivation of Factors Va and VIIIa.

Protease: A protein that catalyzes the cleavage of peptide bonds in other proteins.

Serine Protease: Serine protease refers to a member of a family of protein-cleaving (proteolytic) enzymes that share a functional domain defined by amino acid residues $Asp^{102}$, $Ser^{195}$, and $His^{57}$ of chymotrypsin. Examples of serine proteases include those in the complement convertase family (e.g., factors Clr, Cls, D, C3 convertase, C2, Factor B, Factor I); those in the plasminogen activator family (e.g., tissue plasminogen activator, urinary plasminogen activator, streptokinase-plasminogen complex); those in the blood coagulation pathway family (e.g., factors XIIIa, XIIa, XIa, Xa, IXa, VIIa, thrombin, plasma kallikrein, activated PC); those in the digestive enzyme family (e.g., trypsin, chymotrypsin, pancreatic elastase, enterokinase), those in the hormone family (e.g., tissue kallikrein, post proline cleaving enzyme), and the like. "Serine protease", as used herein, is further intended to encompass all substantially homologous molecules.

Synthetic Peptide: Synthetic Peptide refers to a chemically produced chain of amino acid residues linked together by peptide bonds that is free of naturally occurring proteins and fragments thereof.

Zymogen: A precursor protein lacking enzymatic activity that is cleaved to yield an active protease. Conventional terminology identifies the active protein with a small 'a': for example, Factor VII is the zymogen and Factor VIIa is the active protease.

B. Polypeptides

A polypeptide of the present invention comprises no more than about 100 amino acid residues, preferably no more than about 60 residues, more preferably no more than about 30 residues, and includes an amino acid residue sequence defining a serine protease binding domain sequence as described herein.

A serine protease binding domain sequence is an amino acid residue sequence that defines a surface-exposed region of a native and naturally folded serine protease protein, a region that participates in an essential protein-protein interaction between the serine protease and another protein during the catalytic process of the serine protease. By "essential protein-protein interaction" is meant that if the interaction is perturbed by a competition reaction using a polypeptide of the present invention, the catalytic activity of the serine protease is diminished or extinguished. Thus, the interaction is essential for the protease to exert its catalytic activity.

The discoveries described herein identify "exosites" on a serine protease which are each binding domain sequences. The term exosite indicates a region of a serine protease that is defined by amino acid residues which are not located at the region of the protease responsible for the catalytic activity. That is, an exosite is not located at the catalytic site.

Serine proteases are a class of proteolytic enzymes that include as a portion of the catalytic site characteristic amino acid residues including serine that participate in the catalytic reaction. As a class, the members are evolutionarily related, contain similar three-dimensional structures, i.e., the family members exhibit structural homology, and share a degree of homology in their amino acid residue sequences that allows the reproducible alignment of the individual sequence of each member with the sequence of other members. By alignment, one can identify the position of a exosite as defined herein on any serine protease.

Serine proteases as a class include the blood coagulation pathway family serine proteases including Factors XIIIa, XIIa, XIa, Xa, IXa, VIIa, thrombin, plasma kallikrein, and activated PC; the plasminogen activator family including tissue plasminogen activator (TPA), urinary plasminogen activator and streptokinase-plasminogen complex; the complement conversion family of proteases including Clr, Cls, D, C3 convertase, C2, Factor B, Factor I; the digestive enzyme family including trypsin, chymotrypsin, pancreatic elastase, enterokinase; and the hormone family proteases including tissue kallikrein, post proline cleaving enzyme and other hormone cleaving enzymes.

The blood coagulation family of serine proteases are particularly preferred because as participants in blood coagulation processes, they provide polypeptides useful as anticoagulants.

Sequence alignment of the amino acid residue sequence of a serine protease to identify a binding domain sequence in the protease that is homologous to a sequence defined herein can be accomplished by a variety of commercially available computer comparison programs. A preferred homology comparison program is the Genetics Computer Group Sequence Analysis Software Program GAP described by and available from Devereux et al, *Nucleic Acids Res.*, 12:386–395 (1984).

An alignment of preferred members of the class at two exosites on a serine protease are shown in Tables 1 and 2, using the methods of Devereux et al, supra.

TABLE 1

| SEQ ID NO | PROTEIN[1] | RESIDUE NUMBER[2] | AMINO ACID RESIDUE SEQUENCE[3] |
|---|---|---|---|
| (1) | PC | 390–404 | YGVYTKVSRYLDWIH |
| (2) | IX | 395–409 | YGIYTKVSRYVNWIK |
| (3) | X | 409–423 | YGIYTKVTAFLKWID |
| (4) | PT | 557–571 | YGFYTHVFRLKKWIQ |
| (5) | VII | 374–388 | FGVYTRVSQYIEWLQ |
| (10) | CT | 225–239 | PGVYARVTALVNWVQ |

[1]The abbreviations indicate the enzymes as follows: PC, protein C; IX, Factor IX; X, Factor X; PT, prothrombin; VII, Factor VII; CT, chymotrypsinogen.
[2]"Residue Number" designates a polypeptide having the amino acid residue sequence shown in the indicated SEQ ID NO spanning the indicated amino acid residues positions.
[3]The amino acid residue sequence is shown in single-letter code to allow for convenient alignment of the various protein sequences.

An additional exosite is identified by the alignment of the serine proteases shown in Table 2.

TABLE 2

| SEQ ID NO | PROTEIN[1] | RESIDUE NUMBER[2] | AMINO ACID RESIDUE SEQUENCE[3] |
|---|---|---|---|
| (1) | PC | 311–331 | KRNRTFVLNFIKIPVVPHNEC |
| (2) | IX | 316–336 | KGRSALVLQYLRVPLVDRATC |
| (3) | X | 330–350 | KGRQSTRLKMLEVPYVDRNSC |
| (4) | PT | 474–493 | KGQ.PSVLQVVNLPIVERPVC |
| (5) | VII | 290–310 | RGATALELMVLNVPRLMTQDC |
| (6) | CT | 148–168 | NANTPDRLQQASLPLLSNTNC |
| (7) | TP | 134–154 | GTSYPDVLKCLKAPILSDSSC |

[1-3]The legend to Table 2 is as shown in Table 1.
[2]TP, trypsinogen.

The complete amino acid residue sequence of the proteins shown in Tables 1, 2 and 3 are shown in the SEQ ID NO Listing herein and are also described in the following publications: Protein C, Beckmann et al., *Nucleic Acid Res.*, 13:5233–5247 (1985); Factor IX, Choo et al., *Nature*, 299:178–180 (1982); Factor X, Leytus et al., *Proc. Natl. Acad. Sci. USA*, 81:3699–3702 (1984); prothrombin, Degen et al, *Biochemistry*, 22:2087–2097 (1983); Factor VII, Hagen et al, *Proc. Natl. Acad. Sci. USA*, 83:2412–2416 (1986); chymotrypsinogen, Brown et al, *Biochem. J.*, 101:214–228 (1966); trypsinogen, Mikes et al, *Biochem. Biophys. Res. Comm.*, 24:346–352 (1966).

Using the alignments of the binding domain sequence of the serine proteases shown in Table 1, a serine protease-inhibiting polypeptide has a sequence that includes the conserved amino acid residues glycine (G) at position 2, tyrosine (Y) at position 4, valine (V) at position 7, and tryptophan (W) at position 13 of the binding domain sequence, corresponding to position numbers 391, 393, 396, and 402, respectively, of the complete sequence of protein C (SEQ ID NO 1). A preferred serine protease-inhibiting polypeptide has a sequence that also includes the conserved amino acid residue threonine (T) at position 5 of the binding domain sequence, corresponding to position number 394 of the complete sequence of protein C (SEQ ID NO 1). These conserved residues are useful landmarks in preparing a sequence alignment of the binding domain sequence identified by Table 1.

Using the alignments of the binding domain sequence of the serine proteases shown in Table 2, a serine protease-inhibiting polypeptide has a sequence that includes the conserved amino acid residues leucine (L) at position 8 and proline (P) at position 14 of the binding domain sequence, corresponding to position numbers 318 and 324, respectively, of the complete sequence of protein C (SEQ ID NO 1). A preferred serine protease-inhibiting polypeptide has a sequence that also includes the conserved amino acid residue cysteine (C) at position 21 of the binding domain sequence, corresponding to position number 331 of the complete sequence of protein C (SEQ ID NO 1). These conserved residues are useful landmarks in preparing a sequence alignment of the binding domain sequence identified by Table 2.

The following detailed description of preferred polypeptides identifies serine protease-inhibiting polypeptides of the present invention. The polypeptides shown include the blood coagulation serine proteases protein C, Factor IX, Factor X, prothrombin, and Factor VII, and is not intended to be construed as limiting. Applying the same teachings as is hereinbelow, serine protease-inhibiting polypeptides are defined that can be derived from other serine proteases.

Protein C

Protein C (PC) is activated in blood by the thrombin-thrombomodulin complex to form activated Protein C (APC) which functions in conjunction with its nonenzymatic cofactor protein S as a natural anticoagulant by proteolytic inactivation of the blood coagulation Factors Va and VIIIa.

Protein C consists of a 155 amino acid residue light chain and a 262 amino acid residue heavy chain. The amino acid residue sequence of protein C is listed as SEQ ID NO 1 in the sequence listing.

In one embodiment the invention contemplates a polypeptide that includes an amino acid residue sequence that defines a serine protease binding domain sequence derived from PC, i.e., the polypeptide is a PC polypeptide. A PC polypeptide inhibits the activity of its corresponding serine protease, APC, and has anticoagulant activity as described herein.

A preferred PC polypeptide includes an amino acid residue sequence represented by the formula: -Lys-Arg-Asn-Arg-Thr-Phe-Val-Leu-Asn-Phe-Ile-Lys-Ile-Pro-Val- (1:311–325).

The SEQ ID NO and corresponding residues of a described amino acid residue sequence are conveniently recited herein in parenthesis after a designated amino acid residue sequence, where the first number is the SEQ ID NO and the range following the colon represents the residue numbers of the indicated amino acid residues in the sequence listing. For example, "(1:311–325)" refers to the sequence "Lys-Arg-Asn-Arg-Thr-Phe-Val-Leu-Asn-Phe-Ile-Lys-Ile-Pro-Val" shown in SEQ ID NO 1.

More preferably, a contemplated PC polypeptide has an amino acid residue sequence represented by a formula selected from the group consisting of: Lys-Arg-Asn-Arg-Thr-Phe-Val-Leu-Asn-Phe-Ile-Lys-Ile-Pro-Val- (1:311–325), and Lys-Arg-Asn-Arg-Thr-Phe-Val-Leu-Asn-Phe-Ile-Lys-Ile-Pro-Val-Val-Pro-His-Asn-Glu-Cys (1:311–331).

In another embodiment, a PC polypeptide includes an amino acid residue sequence represented by the formula: -Gly-Arg-Pro-Trp-Lys-Arg-Met-Glu-Lys-Lys-Arg-Ser-His-Leu- (1:142–155), and has the ability to inhibit blood coagulation. More preferably, the polypeptide has an amino acid residue sequence represented by a formula selected from the group consisting of: Gly-Arg-Pro-Trp-Lys-Arg-Met-Glu-Lys-Lys-Arg-Ser-His-Leu (1:142–155).

Factor IX

In another embodiment, the invention contemplates a serine protease binding domain sequence derived from Factor IX, i.e., the polypeptide is a IX polypeptide. Exemplary domains are identified in Tables 1 and 2. A IX polypeptide inhibits the activity of its corresponding serine protease, Factor IX, and has anticoagulant activity as described herein.

A preferred IX polypeptide includes an amino acid residue sequence represented by the formula: -Lys-Gly-Arg-Ser-Ala-Leu-Val-Leu-Gln-Tyr-Leu-Arg-Val-Pro-Leu- (2:316–330).

In preferred embodiments, the polypeptide has an amino acid residue sequence represented by a formula selected from the group consisting of: His-Lys-Gly-Arg-Ser-Ala-Leu-Val-Leu-Gln-Tyr-Leu-Arg-Val-Pro-Leu (2:315–330), Lys-Gly-Arg-Ser-Ala-Leu-Val-Leu-Gln-Tyr-Leu-Arg-Val-Pro-Leu (2:316–330), and Lys-Gly-Arg-Ser-Ala-Leu-Val-Leu-Gln-Tyr-Leu-Arg-Val-Pro-Leu-Val-Asp-Arg-Ala-Thr-Cys (2:316–336).

Another related embodiment of the present invention contemplates a IX polypeptide that includes an amino acid residue sequence represented by the formula: -Leu-Val-Leu-Gln-Tyr-Leu-Arg-Val-Pro-Leu-(2:321–330). In preferred embodiments, the polypeptide has an amino acid residue sequence represented by a formula selected from the group consisting of: Leu-Val-Leu-Gln-Tyr-Leu-Arg-Val-Pro-Leu (2:321–330), and Leu-Val-Leu-Gln-Tyr-Leu-Arg-Val-Pro-Leu-Val-Asp-Arg-Ala-Thr (2:321–335).

Another related embodiment of the present invention contemplates a IX polypeptide that includes an amino acid residue sequence represented by the formula: -Tyr-Gly-Ile-Tyr-Thr-Lys-Val-Ser-Arg-Tyr-Val-Asn-Trp-Ile-Lys- (2:395–409), -Lys-Val-Ser-Arg-Tyr-Val-Asn-Trp-Ile-Lys- (2:400–409), or -Lys-Val-Ser-Arg-Tyr-Val-Asn-Trp-Ile-Lys-Glu-Lys-Thr-Lys-Leu- (2:400–414). In preferred embodiments, the polypeptide has an amino acid residue sequence represented by a formula selected from the group consisting of: Tyr-Gly-Ile-Tyr-Thr-Lys-Val-Ser-Arg-Tyr-Val-Asn-Trp-Ile-Lys (2:395–409), Tyr-Gly-Ile-Tyr-Thr-Lys-Val-Ser-Arg-Tyr-Val-Asn-Trp-Ile-Lys-Glu-Lys-Thr-Lys-Leu (2:395–414), Lys-Val-Ser-Arg-Tyr-Val-Asn-Trp-Ile-Lys (2:400–409) and Lys-Val-Ser-Arg-Tyr-Val-Asn-Trp-Ile-Lys-Glu-Lys-Thr-Lys-Leu (2:400–414).

Factor X

In another embodiment, the invention contemplates a serine protease binding domain sequence derived from Factor X, i.e., the polypeptide is a X polypeptide. Exemplary domains are identified in Tables 1 and 2. A X polypeptide inhibits the activity of its corresponding serine protease, Factor X, and has anticoagulant activity as described herein.

A preferred X polypeptide includes an amino acid residue sequence represented by the formula: -Lys-Gly-Arg-Gln-Ser-Thr-Arg-Leu-Lys-Met-Leu-Glu-Val-Pro-Tyr- (3:330–344).

In preferred embodiments, the polypeptide has an amino acid residue sequence represented by a formula selected from the group consisting of: Glu-Lys-Gly-Arg-Gln-Ser-Thr-Arg-Leu-Lys-Met-Leu-Glu-Val-Pro-Tyr (3:329–344), Lys-Gly-Arg-Gln-Ser-Thr-Arg-Leu-Lys-Met-Leu-Glu-Val-Pro-Tyr (3:330–344), and Lys-Gly-Arg-Gln-Ser-Thr-Arg-Leu-Lys-Met-Leu-Glu-Val-Pro-Tyr-Val-Asp-Arg-Asn-Ser-Cys (3:330–350).

Another related embodiment of the present invention contemplates a X polypeptide that includes an amino acid residue sequence represented by the formula: -Ala-Arg-Lys-Gly-Lys-Tyr-Gly-Ile-Tyr-Thr-Lys-Val-Thr-Ala-Phe- (3:404–418), or -Val-Thr-Ala-Phe-Leu-Lys-Trp-Ile-Asp-Arg-Ser-Met-Lys-Thr-Arg- (3:415–429). In preferred embodiments, the polypeptide has an amino acid residue sequence represented by a formula selected from the group consisting of: Ala-Arg-Lys-Gly-Lys-Tyr-Gly-Ile-Tyr-Thr-Lys-Val-Thr-Ala-Phe- (3:404–418) and Val-Thr-Ala-Phe-Leu-Lys-Trp-Ile-Asp-Arg-Ser-Met-Lys-Thr-Arg (3:415–429).

Prothrombin

In another embodiment, the invention contemplates a serine protease binding domain sequence derived from prothrombin, i.e., the polypeptide is a PT polypeptide. Exemplary domains are identified in Tables 1 and 2. A PT polypeptide inhibits the activity of its corresponding serine protease, prothrombin, and has anticoagulant activity as described herein.

A preferred PT polypeptide includes an amino acid residue sequence represented by the formula: -Asn-Leu-Lys-Glu-Thr-Trp-Thr-Ala-Asn-Val-Gly-Lys-Gly-Gln-Pro- (4:463–477), -Lys-Gly-Gln-Pro-Ser-Val-Leu-Gln-Val-Val-Asn-Leu-Pro-Ile- (4:474–487), or -Gln-Val-Val-Asn-Leu-Pro-Ile-Val-Glu-Arg-Pro-Val-Ser-Lys-Asp- (4:481–495).

In preferred embodiments, the polypeptide has an amino acid residue sequence represented by a formula selected from the group consisting of: Asn-Leu-Lys-Glu-Thr-Trp-Thr-Ala-Asn-Val-Gly-Lys-Gly-Gln-Pro (4:463–477), Gly-Lys-Gly-Gln-Pro-Ser-Val-Leu-Gln-Val-Val-Asn-Leu-Pro-Ile (4:473–487), Lys-Gly-Gln-Pro-Ser-Val-Leu-Gln-Val-Val-Asn-Leu-Pro-Ile (4:474–487), Lys-Gly-Gln-Pro-Ser-Val-Leu-Gln-Val-Val-Asn-Leu-Pro-Ile-Val-Glu-Arg-Pro-Val-Cys (4:474–493), or Gln-Val-Val-Asn-Leu-Pro-Ile-Val-Glu-Arg-Pro-Val-Ser-Lys-Asp (4:481–495).

Another related embodiment of the present invention contemplates a PT polypeptide that includes an amino acid residue sequence represented by the formula: -Tyr-Gly-Phe-Tyr-Thr-His-Val-Phe-Arg-Leu-Lys-Lys-Trp-Ile-Gln- (4:557–571).

In preferred embodiments, the polypeptide has an amino acid residue sequence represented by a formula selected from the group consisting of: Tyr-Gly-Phe-Tyr-Thr-His-Val-Phe-Arg-Leu-Lys-Lys-Trp-Ile-Gln (4:557–571).

Factor VII

In another embodiment, the invention contemplates a serine protease binding domain sequence derived from Factor VII, i.e., the polypeptide is a VII polypeptide. Exemplary domains are identified in Tables 1 and 2. A VII polypeptide inhibits the activity of its corresponding serine protease, Factor VII, and has anticoagulant activity as described herein.

A preferred VII polypeptide includes an amino acid residue sequence represented by the formula: -Arg-Gly-Ala-Thr-Ala-Leu-Glu-Leu-Met-Val-Leu-Asn-Val-Pro-Arg- (5:290–304), and more preferably includes the sequence -Arg-Gly-Ala-Thr-Ala-Leu-Glu-Leu-Met-Val-Leu-Asn-Val-Pro-Arg-Leu-Met-Thr-Gln-Asp-Cys- (5:290–310).

In preferred embodiments, the polypeptide has an amino acid residue sequence represented by a formula selected from the group consisting of: Asp-Arg-Gly-Ala-Thr-Ala-Leu-Glu-Leu-Met-Val-Leu-Asn-Val-Pro-Arg (5:289–304), Arg-Gly-Ala-Thr-Ala-Leu-Glu-Leu-Met-Val-Leu-Asn-Val-Pro-Arg (5:290–304), and Arg-Gly-Ala-Thr-Ala-Leu-Glu-Leu-Met-Val-Leu-Asn-Val-Pro-Arg-Leu-Met-Thr-Gln-Asp-Cys (5:290–310).

Another related embodiment of the present invention contemplates a VII polypeptide that includes an amino acid residue sequence represented by the formula: -Phe-Gly-Val-Tyr-Thr-Arg-Val-Ser-Gln-Tyr-Ile-Glu-Trp-Leu-Gln- (5:374–388). In preferred embodiments, the polypeptide has an amino acid residue sequence represented by a formula selected from the group consisting of: Phe-Gly-Val-Tyr-Thr-Arg-Val-Ser-Gln-Tyr-Ile-Glu-Trp-Leu-Gln (5:374–388).

Preferred anticoagulant polypeptides, their designations, and their amino acid residue positions are shown in Table 3.

TABLE 3

| SEQ ID NO | PROTEIN[1] | RESIDUE NUMBER[2] |
|---|---|---|
| (1) | PC | 142–155 |
| (1) | PC | 311–325 |
| (1) | PC | 311–331 |
| (2) | IX | 315–330 |
| (2) | IX | 316–336 |
| (2) | IX | 321–330 |
| (2) | IX | 321–335 |
| (2) | IX | 395–409 |
| (2) | IX | 400–409 |
| (2) | IX | 400–414 |
| (3) | X | 329–344 |
| (3) | X | 330–344 |
| (3) | X | 330–350 |
| (3) | X | 404–418 |
| (3) | X | 415–429 |
| (4) | PT | 463–477 |
| (4) | PT | 473–487 |
| (4) | PT | 474–487 |
| (4) | PT | 474–493 |
| (4) | PT | 481–495 |
| (4) | PT | 557–571 |
| (5) | VII | 289–304 |
| (5) | VII | 290–304 |
| (5) | VII | 290–310 |
| (5) | VII | 374–388 |

[1]–[3]The legends of Table 3 are as shown in Table 1.

The polypeptides described herein inhibit coagulation. Thus, the present invention contemplates a polypeptide as defined herein, or composition containing one or more of said polypeptides, wherein said polypeptide has an amino acid residue sequence that includes the sequence represented by a formula selected from the group consisting of: -Lys-Arg-Asn-Arg-Thr-Phe-Val-Leu-Asn-Phe-Ile-Lys-Ile-Pro-Val- (1:311–325), -Gly-Arg-Pro-Trp-Lys-Arg-Met-Glu-Lys-Lys-Arg-Ser-His-Leu- (1:142–155), -Lys-Gly-Arg-Ser-Ala-Leu-Val-Leu-Gln-Tyr-Leu-Arg-Val-Pro-Leu- (2:316–330), -Leu-Val-Leu-Gln-Tyr-Leu-Arg-Val-Pro-Leu- (2:321–330), -Tyr-Gly-Ile-Tyr-Thr-Lys-Val-Ser-Arg-Tyr-Val-Asn-Trp-Ile-Lys- (2:395–409), -Lys-Val-Ser-Arg-Tyr-Val-Asn-Trp-Ile-Lys- (2:400–409), -Lys-Val-Ser-Arg-Tyr-Val-Asn-Trp-Ile-Lys-Glu-Lys-Thr-Lys-Leu- (2:400–414), -Lys-Gly-Arg-Gln-Ser-Thr-Arg-Leu-Lys-Met-Leu-Glu-Val-Pro-Tyr- (3:330–344), -Ala-Arg-Lys-Gly-Lys-Tyr-Gly-Ile-Tyr-Thr-Lys-Val-Thr-Ala-Phe- (3:404–418), -Val-Thr-Ala-Phe-Leu-Lys-Trp-Ile-Asp-Arg-Ser-Met-Lys-Thr-Arg- (3:415–429), -Asn-Leu-Lys-Glu-Thr-Trp-Thr-Ala-Asn-Val-Gly-Lys-Gly-Gln-Pro- (4:463–477), -Lys-Gly-Gln-Pro-Ser-Val-Leu-Gln-Val-Val-Asn-Leu-Pro-Ile- (4:474–487), -Gln-Val-Val-Asn-Leu-Pro-Ile-Val-Glu-Arg-Pro-Val-Ser-Lys-Asp- (4:481–495), -Tyr-Gly-Phe-Tyr-Thr-His-Val-Phe-Arg-Leu-Lys-Lys-Trp-Ile-Gln- (4:557–571), -Arg-Gly-Ala-Thr-Ala-Leu-Glu-Leu-Met-Val-Leu-Asn-Val-Pro-Arg- (5:290–310), and -Phe-Gly-Val-Tyr-Thr-Arg-Val-Ser-Gln-Tyr-Ile-Glu-Trp-Leu-Gln- (5:374–388).

A polypeptide of the present invention has the capacity to inhibit the binding of the corresponding serine protease to its natural substrate as shown by the teachings herein. In addition, the present polypeptides also inhibit the activity of the corresponding serine protease by competitive inhibition. The polypeptides can inhibit serine protease activity both in vitro in standardized assay conditions and in vivo.

Methods to measure the inhibition of a serine protease are conveniently carried out in vitro in a standardized enzyme assay for the serine protease. Exemplary assays for several of the blood coagulation factors described herein are detailed in the Examples herein, and can be used to detect the presence of inhibition.

A polypeptide is inhibitory where there is a decrease in the enzyme activity of at least one percent of the total activity, preferably at least 10 percent, and more preferably at least 50 percent. The extent of inhibition measurable depends at least on the concentration of the inhibiting polypeptide and the enzyme assay conditions. Thus, the above inhibitory levels are preferably measured in a standardized assay, namely in the presence and absence of the polypeptide, with all other conditions being maintained the same. Preferably, the standardized assay conditions include at least an equimolar amount of polypeptide relative to corresponding serine protease, and the inhibition of proteolytic activity is at least one percent of control activity in the absence of polypeptide.

Insofar as polypeptide inhibition can be expressed in terms of the concentration of polypeptide required to produce a fifty percent reduction of measured activity for the corresponding serine protease when compared to the activity in the absence of polypeptide, referred to as an $IC_{50}$ dose, it is preferred that a subject polypeptide has an $IC_{50}$ of at least 500 micromolar (uM), preferably at least 100 uM, and more preferably at least 10 uM.

Preferably, a polypeptide of this invention is further characterized by its ability to immunologically mimic an epitope (antigenic determinant) expressed by the serine protease from which the polypeptide was derived. The protease from which a polypeptide of this invention is derived is also referred to as the corresponding protease.

As used herein, the phrase "immunologically mimic" in its various grammatical forms refers to the ability of a polypeptide of this invention to immunoreact with an antibody of the present invention that immunoreacts with a native epitope on the corresponding protease as defined herein.

It should be understood that a subject polypeptide need not be identical to the amino acid residue sequence of the corresponding protease, so long as it includes the required sequence and is able to inhibit the activity of the corresponding protease and act as an anticoagulant such as is described herein.

A subject polypeptide includes any analog, fragment or chemical derivative of a polypeptide whose amino acid residue sequence is shown herein so long as the polypeptide is capable of inhibiting coagulation. Therefore, a present polypeptide can be subject to various changes, substitutions, insertions, and deletions where such changes provide for certain advantages in its use. In this regard, a polypeptide of this invention corresponds to, rather than is identical to, the sequence of the corresponding protease where one or more changes are made and it retains the ability to inhibit coagulation in one or more of the assays as defined herein.

The term "analog" includes any polypeptide having an amino acid residue sequence substantially identical to a sequence specifically shown herein in which one or more residues have been conservatively substituted with a functionally similar residue and which displays the ability to inhibit coagulation as described herein. Examples of conservative substitutions include the substitution of one nonpolar (hydrophobic) residue such as isoleucine, valine, leucine or methionine for another, the substitution of one polar (hydrophilic) residue for another such as between arginine and lysine, between glutamine and asparagine, between glycine and serine, the substitution of one basic residue such as lysine, arginine or histidine for another, or the substitution of one acidic residue, such as aspartic acid or glutamic acid for another.

The phrase "conservative substitution" also includes the use of a chemically derivatized residue in place of a non-derivatized residue provided that such polypeptide displays the requisite inhibition activity.

"Chemical derivative" refers to a subject polypeptide having one or more residues chemically derivatized by reaction of a functional side group. Such derivatized molecules include for example, those molecules in which free amino groups have been derivatized to form amine hydrochlorides, p-toluene sulfonyl groups, carbobenzoxy groups, t-butyloxycarbonyl groups, chloroacetyl groups or formyl groups. Free carboxyl groups may be derivatized to form salts, methyl and ethyl esters or other types of esters or hydrazides. Free hydroxyl groups may be derivatized to form O-acyl or O-alkyl derivatives. The imidazole nitrogen of histidine may be derivatized to form N-im-benzylhistidine. Also included as chemical derivatives are those peptides which contain one or more naturally occurring amino acid derivatives of the twenty standard amino acids. For examples: 4-hydroxyproline may be substituted for proline; 5-hydroxylysine may be substituted for lysine; 3-methylhistidine may be substituted for histidine; homoserine may be substituted for serine; and ornithine may be substituted for lysine. Polypeptides of the present invention also include any polypeptide having one or more additions and/or deletions or residues relative to the sequence of a polypeptide whose sequence is shown herein, so long as the requisite activity is maintained.

A polypeptide is free of homoserine lactone when there is no detectable homoserine lactone present in the polypeptide when subjected to conventional amino acid analysis able to indicate the presence of homoserine lactone or other amino acids. Amino acid analysis methods suitable to detect homoserine lactone are generally well known in the art.

The term "fragment" refers to any subject polypeptide having an amino acid residue sequence shorter than that of a polypeptide whose amino acid residue sequence is shown herein.

When a polypeptide of the present invention has a sequence that is not identical to the sequence of the corresponding protease, it is typically because one or more conservative or non-conservative substitutions have been made, usually no more than about 30 number percent, and preferably no more than 10 number percent of the amino acid residues are substituted.

"Substantially homologous" means that a particular subject sequence or molecule, for example, a mutant sequence, varies from a reference sequence by one or more substitutions, deletions, or additions, the net effect of which does not result in an adverse functional dissimilarity between reference and subject sequences. For purposes of the present invention, amino acid sequences having greater than 90 percent similarity, equivalent biological activity, and equivalent expression characteristics are considered substantially homologous and are included within the scope of proteins defined by the terms "serine protease".

Amino acid sequences having greater than 40 percent similarity are considered substantially similar. For purposes of determining homology or similarity, truncation or internal deletions of the reference sequence should be disregarded, as should subsequent modifications of the molecule, e.g., glycosylation. Sequences having lesser degrees of homology and comparable bioactivity are considered equivalents.

Additional residues may also be added at either terminus of an anticoagulant polypeptide of this invention for the purpose of providing a "linker" by which the polypeptides of this invention can be conveniently affixed to a label or solid matrix, or carrier. Preferably, the linker residues do not form epitopes which are cross reactive with the corresponding protease, i.e., are not sufficiently similar in structure to the corresponding protease as to produce cross-reacting antibodies.

Labels, solid matrices and carriers that can be used with the polypeptides of this invention are described hereinbelow.

Amino acid residue linkers are usually at least one residue and can be 40 or more residues, more often 1 to 10 residues, but do not form epitopes cross-reactive with the corresponding protease. Typical amino acid residues used for linking are tyrosine, cysteine, lysine, glutamic and aspartic acid, or the like. In addition, a subject polypeptide can differ, unless otherwise specified, from the natural sequence of the corresponding protease by the sequence being modified by terminal-$NH_2$ acylation, e.g., acetylation, or thioglycolic acid amidation, by terminal-carboxylamidation, e.g., with ammonia, methylamine, and the like terminal modifications. Terminal modifications are useful, as is well known, to reduce susceptibility by proteinase digestion, and therefore serve to prolong half life of the polypeptides in solutions, particularly biological fluids where proteases may be present. In this regard, polypeptide cyclization is also a useful terminal modification.

When coupled to a carrier to form what is known in the art as a carrier-hapten conjugate, a polypeptide of the present invention is capable of inducing antibodies that immunoreact with the corresponding protease. In view of the well established principle of immunologic cross-reactivity, the present invention therefore contemplates antigenically related variants of the polypeptides shown in Tables 1, 2 and 3. An "antigenically related variant" is a subject polypeptide that is capable of inducing antibody molecules that immunoreact with a polypeptide from Tables 1, 2 and 3, and immunoreact with the corresponding protease.

Any peptide of the present invention may be used in the form of a pharmaceutically acceptable salt. Suitable acids which are capable of forming salts with the peptides of the present invention include inorganic acids such as hydrochloric acid, hydrobromic acid, perchloric acid, nitric acid, thiocyanic acid, sulfuric acid, phosphoric acetic acid, propionic acid, glycolic acid, lactic acid, pyruvic acid, oxalic acid, malonic acid, succinic acid, maleic acid, fumaric acid, anthranilic acid, cinnamic acid, naphthalene sulfonic acid, sulfanilic acid or the like.

Suitable bases capable of forming salts with the peptides of the present invention include inorganic bases such as sodium hydroxide, ammonium hydroxide, potassium hydroxide and the like; and organic bases such as mono-, di- and tri-alkyl and aryl amines (e.g. triethylamine, diisopropyl amine, methyl amine, dimethyl amine and the like) and optionally substituted ethanolamines (e.g. ethanolamine, diethanolamine and the like).

A polypeptide of the present invention also referred to herein as a subject polypeptide, can be synthesized by any of the techniques that are known to those skilled in the polypeptide art, including recombinant DNA techniques. Synthetic chemistry techniques, such as a solid-phase Merrifield-type synthesis, are preferred for reasons of purity, antigenic specificity, freedom from undesired side products, ease of production and the like. An excellent summary of the many techniques available can be found in J. M. Steward and J. D. Young, "Solid Phase Peptide Synthesis", W. H. Freeman Co., San Francisco, 1969; M. Bodanszky, et al., "Peptide Synthesis", John Wiley & Sons, Second Edition, 1976 and J. Meienhofer, "Hormonal Proteins and Peptides", Vol. 2, p. 46, Academic Press (New York), 1983 for solid phase peptide synthesis, and E. Schroder and K. Kubke, "The Peptides", Vol. 1, Academic Press (New York), 1965 for classical solution synthesis, each of which is incorporated herein by reference. Appropriate protective groups usable in such synthesis are described in the above texts and in J. F. W. McOmie, "Protective Groups in Organic Chemistry", Plenum Press, New York, 1973, which is incorporated herein by reference.

In general, the solid-phase synthesis methods contemplated comprise the sequential addition of one or more amino acid residues or suitably protected amino acid residues to a growing peptide chain. Normally, either the amino or carboxyl group of the first amino acid residue is protected by a suitable, selectively removable protecting group. A different, selectively removable protecting group is utilized for amino acids containing a reactive side group such as lysine.

Using a solid phase synthesis as exemplary, the protected or derivatized amino acid is attached to an inert solid support through its unprotected carboxyl or amino group. The protecting group of the amino or carboxyl group is then selectively removed and the next amino acid in the sequence having the complimentary (amino or carboxyl) group suitably protected is admixed and reacted under conditions suitable for forming the amide linkage with the residue already attached to the solid support. The protecting group of the amino or carboxyl group is then removed from this newly added amino acid residue, and the next amino acid (suitably protected) is then added, and so forth. After all the desired amino acids have been linked in the proper sequence, any remaining terminal and side group protecting groups (and solid support) are removed sequentially or concurrently, to afford the final polypeptide.

A polypeptide of this invention can be used, inter alia, in the diagnostic methods and systems of the present invention as a reagent in methods to detect the presence in a body sample of a serine protease. A polypeptide can also be used to prepare an inoculum as described herein for the preparation of antibodies that immunoreact with epitopes on a serine protease. In addition, a polypeptide can be used in vitro to inhibit the activity of the corresponding serine protease where proteolytic activity is not desired.

A polypeptide of this invention can also be used in the therapeutic methods of the present invention to inhibit the activity of the corresponding serine protease. Particularly preferred is the use of anticoagulant polypeptides as anticoagulants.

C. Antibodies and Monoclonal Antibodies

The term "antibody" in its various grammatical forms is used herein as a collective noun that refers to a population of immunoglobulin molecules and/or immunologically active portions of immunoglobulin molecules, i.e., molecules that contain an antibody combining site or paratope.

An "antibody combining site" is that structural portion of an antibody molecule comprised of heavy and light chain variable and hypervariable regions that specifically binds antigen.

The phrase "antibody molecule" in its various grammatical forms as used herein contemplates both an intact immunoglobulin molecule and an immunologically active portion of an immunoglobulin molecule.

Exemplary antibody molecules for use in the diagnostic methods and systems of the present invention are intact immunoglobulin molecules, substantially intact immunoglobulin molecules and those portions of an immunoglobulin molecule that contain the paratope, including those portions known in the art as Fab, Fab', F(ab')$_2$ and F(v).

Fab and F(ab')$_2$ portions of antibodies are prepared by the proteolytic reaction of papain and pepsin, respectively, on substantially intact antibodies by methods that are well known. See for example, U.S. Pat. No. 4,342,566 to Theofilopolous and Dixon. Fab' antibody portions are also well known and are produced from F(ab')$_2$ portions followed by reduction of the disulfide bonds linking the two heavy chain portions as with mercaptoethanol, and followed by alkylation of the resulting protein mercaptan with a reagent such as iodoacetamide. An antibody containing intact antibody molecules is preferred, and is utilized as illustrative herein.

An antibody of the present invention comprises antibody molecules that inhibit serine protease activity of the corresponding serine protease with which the antibody immunoreacts as described herein. Furthermore, where the antibody is derived from a blood coagulation family member serine protease as described herein, the antibody inhibits coagulation.

Antibody molecules of this invention are further characterized as being capable of immunoreacting with 1) an isolated serine protease, and 2) a polypeptide of the present invention derived from that serine protease, (i.e., the corresponding serine protease) and being substantially free of antibody molecules that immunoreact with a polypeptide derived from a region of the serine protease that is not within an exosite as defined herein.

Thus in one embodiment, the invention contemplates an antibody comprising antibody molecules that inhibit coagulation and that immunoreact with (a) protein C, and with (b) a polypeptide having an amino acid residue sequence represented by the formula selected from the group consisting of (1:311–325) and (1:142–155); but do not immunoreact with the polypeptide having an amino acid residue sequence represented by the formula (1:266–287).

Another embodiment contemplates an antibody comprising antibody molecules that inhibit coagulation and that immunoreact with (a) Factor IX, and with (b) a polypeptide having an amino acid residue sequence represented by the formula selected from the group consisting of (2:316–330), (2:321–330), (2:395–409), (2:400–409) and (2:400–414); but do not immunoreact with the polypeptide having an amino acid residue sequence represented by the formula (2:271–292).

The invention also contemplates an antibody comprising antibody molecules that inhibit coagulation and that immunoreact with (a) Factor X, and with (b) a polypeptide having an amino acid residue sequence represented by the formula selected from the group consisting of (3:330–344), (3:404:418) and (3:415–429); but do not immunoreact with the polypeptide having an amino acid residue sequence represented by the formula: (3:285–306).

Another embodiment contemplates an antibody comprising antibody molecules that inhibit coagulation and that immunoreact with (a) prothrombin, and with (b) a polypeptide having an amino acid residue sequence represented by the formula selected from the group consisting of (4:463–477), (4:474–487), (4:481–495) and (4:557–571); but do not immunoreact with the polypeptide having an amino acid residue sequence represented by the formula (4:429–450).

The invention also contemplates an antibody comprising antibody molecules that inhibit coagulation and that immunoreact with (a) Factor VII, and with (b) a polypeptide having an amino acid residue sequence represented by the formula selected from the group consisting of (5:289–304), (5:290–304), (5:290–310) and (5:374–388); but do not immunoreact with the polypeptide having an amino acid residue sequence represented by the formula: (5:245–266).

Antibody immunoreactivity with the above-specified polypeptides and serine protease antigens can be measured by a variety of immunological assays known in the art. Exemplary immunoreaction of an antibody with a polypeptide peptide is described in Example 2c3). Direct binding with isolated serine protease, for example with PC, APC or the recited PC polypeptides can be assayed at least by the methods described in Examples 2c3) and 3.

By "substantially free" means that the antibody molecules do not immunoreact with the stated antigen at levels within one order of magnitude, and preferably within two orders of magnitude, of the levels of positive immunoreacting species of antigen.

An antibody of the present invention is typically produced by immunizing a mammal with an inoculum containing a polypeptide of this invention and thereby induce in the mammal antibody molecules having immunospecificity for the recited polypeptide. The antibody molecules are then collected from the mammal and isolated to the extent desired by well known techniques such as, for example, by using DEAE Sephadex to obtain the IgG fraction. Exemplary antibody preparation methods are described herein at Example 2.

The preparation of antibodies against polypeptide is well known in the art. [See Staudt et al., *J. Exp. Med.*, 157:687–704 (1983)]. Briefly, to produce a peptide antibody composition of this invention, a laboratory mammal is inoculated with an immunologically effective amount of a recited polypeptide, typically as present in a vaccine of the present invention. The anti polypeptide antibody molecules thereby induced are then collected from the mammal and those immunospecific for both the corresponding serine protease and the immunizing polypeptide are isolated to the extent desired by well known techniques such as, for example, by immunoaffinity chromatography.

To enhance the specificity of the antibody, the antibodies may be purified by immunoaffinity chromatography using solid phase-affixed immunizing polypeptide. The antibody is contacted with the solid phase-affixed immunizing polypeptide for a period of time sufficient for the polypeptide to immunoreact with the antibody molecules to form a solid phase-affixed immunocomplex. The bound antibodies are separated from the complex by standard techniques.

The word "inoculum" in its various grammatical forms is used herein to describe a composition containing a polypeptide of this invention as an active ingredient used for the preparation of antibodies against the polypeptide and its corresponding serine protease. When a polypeptide is used in an inoculum to induce antibodies it is to be understood that the polypeptide can be used in various embodiments, e.g., alone or linked to a carrier as a conjugate, or as a polypeptide polymer. However, for ease of expression and in context of a polypeptide inoculum, the various embodiments of the polypeptides of this invention are collectively referred to herein by the term "polypeptide", and its various grammatical forms.

For a polypeptide that contains fewer than about 35 amino acid residues, it is preferable to use the peptide bound to a carrier for the purpose of inducing the production of antibodies.

One or more additional amino acid residues can be added to the amino- or carboxy-termini of the polypeptide to assist in binding the polypeptide to a carrier. Cysteine residues added at the amino- or carboxy-termini of the polypeptide have been found to be particularly useful for forming conjugates via disulfide bonds. However, other methods well known in the art for preparing conjugates can also be used. Exemplary additional linking procedures include the use of Michael addition reaction products, dialdehydes such as glutaraldehyde, Klipstein, et al., *J. Infect. Dis.*, 147:318–326 (1983) and the like, or the use of carbodiimide technology as in the use of a water-soluble carbodiimide to form amide links to the carrier. For a review of protein conjugation or coupling through activated functional groups, see Aurameas, et al., *Scand. J. Immunol.*, 1:7–23 (1978). Alternatively, the heterobifunctional cross-linker SPDP (N-succinimidyl-3-(2-pyridyldithio)proprionate) can be used to conjugate peptides, in which a carboxy-terminal cysteine has been introduced.

Useful carriers are well known in the art, and are generally proteins themselves. Exemplary of such carriers are keyhole limpet hemocyanin (KLH), edestin, thyroglobulin, albumins such as bovine serum albumin (BSA) or human serum albumin (HSA), red blood cells such as sheep erythrocytes (SRBC), tetanus toxoid, cholera toxoid as well as polyamino acids such as poly (D-lysine: D-glutamic acid), and the like.

The choice of carrier is more dependent upon the ultimate use of the inoculum and is based upon criteria not particularly involved in the present invention. For example, a carrier that does not generate an untoward reaction in the particular animal to be inoculated should be selected.

The present inoculum contains an effective, immunogenic amount of a polypeptide of this invention, typically as a conjugate linked to a carrier. The effective amount of polypeptide per unit dose sufficient to induce an immune response to the immunizing polypeptide depends, among other things, on the species of animal inoculated, the body weight of the animal and the chosen inoculation regimen as is well known in the art. Inocula typically contain polypeptide concentrations of about 10 micrograms to about 500 milligrams per inoculation (dose), preferably about 50 micrograms to about 50 milligrams per dose.

The term "unit dose" as it pertains to the inocula refers to physically discrete units suitable as unitary dosages for animals, each unit containing a predetermined quantity of active material calculated to produce the desired immunogenic effect in association with the required diluent; i.e., carrier, or vehicle. The specifications for the novel unit dose of an inoculum of this invention are dictated by and are directly dependent on (a) the unique characteristics of the active material and the particular immunologic effect to be achieved, and (b) the limitations inherent in the art of compounding such active material for immunologic use in animals, as disclosed in detail herein, these being features of the present invention.

Inocula are typically prepared from the dried solid polypeptide-conjugate by dispersing the polypeptide-conjugate in a physiologically tolerable (acceptable) diluent such as water, saline or phosphate-buffered saline to form an aqueous composition.

Inocula can also include an adjuvant as part of the diluent. Adjuvants such as complete Freund's adjuvant (CFA), incomplete Freund's adjuvant (IFA) and alum are materials well known in the art, and are available commercially from several sources.

The techniques of polypeptide conjugation or coupling through activated functional groups presently known in the art are particularly applicable. See, for example, Aurameas, et al., *Scand. J. Immunol.*, Vol. 8, Suppl. 7:7–23 (1978) and U.S. Pat. No. 4,493,795, U.S. Pat. No. 3,791,932 and U.S. Pat. No. 3,839,153. In addition, a site directed coupling reaction can be carried out so that any loss of activity due to polypeptide orientation after coupling can be minimized. See, for example, Rodwell et al., *Biotech.*, 3:889–894 (1985), and U.S. Pat. No. 4,671,958.

One or more additional amino acid residues may be added to the amino- or carboxy-termini of the polypeptide to assist in binding the polypeptide to form a conjugate. Cysteine residues, usually added at the carboxy-terminus of the polypeptide, have been found to be particularly useful for forming conjugates via disulfide bonds, but other methods well-known in the art for preparing conjugates may be used.

An antibody as described herein can be used, inter alia, in the diagnostic methods and systems of the present invention to detect the presence in a body sample of the corresponding serine protease. A particularly preferred diagnostic method is to monitor the fate of therapeutically administered polypeptide, using antibodies immunospecific for the polypeptide, as described herein.

An anti-PC antibody can also be used in vitro to inhibit the serine protease activity present in a composition containing the protease, for example, in procedures for purifying a blood product where the activity of the protease against the blood product is undesirable.

Anti-PC antibody of this invention can also be used in the therapeutic methods of the present invention to inhibit the corresponding serine protease. In a particularly preferred embodiment, the antibodies produced using a polypeptide derived from a blood coagulation serine protease are useful in methods for inhibiting coagulation.

A preferred antibody is a monoclonal antibody and is used herein as exemplary of an anti-polypeptide antibody of this invention.

The phrase "monoclonal antibody" in its various grammatical forms refers to a population of antibody molecules that contain only one species of antibody combining site capable of immunoreacting with a particular epitope. A monoclonal antibody thus typically displays a single binding affinity for any epitope with which it immunoreacts. A monoclonal antibody may therefore contain an antibody molecule having a plurality of antibody combining sites, each immunospecific for a different epitope, e.g., a bispecific monoclonal antibody.

A monoclonal antibody of this invention comprises antibody molecules that inhibit serine proteases as described herein. Where the monoclonal antibody has immunospecificity for a polypeptide derived from a blood coagulation serine protease, the antibody inhibits coagulation.

A monoclonal antibody of this invention is further characterized as being capable of immunoreacting with 1) isolated serine protease, and 2) a polypeptide of the present invention as described for the antibodies of this invention.

Thus the invention contemplates monoclonal antibodies immunospecific for and raised against a polypeptide of the present invention, and particularly a polypeptide derived from a blood coagulation serine protease as defined herein.

A monoclonal antibody is typically composed of antibodies produced by clones of a single cell called a hybridoma that secretes (produces) only one kind of antibody molecule. The hybridoma cell is formed by fusing an antibody-producing cell and a myeloma or other self-perpetuating cell line. The preparation of such antibodies was first described by Kohler and Milstein, *Nature* 256:495–497 (1975), which description is incorporated by reference. The hybridoma supernates so prepared can be screened for the presence of antibody molecules that immunoreact with the immunizing polypeptides or with the corresponding serine protease, or for inhibition of serine protease as described further herein.

Briefly, to form the hybridoma from which the monoclonal antibody composition is produced, a myeloma or other self-perpetuating cell line is fused with lymphocytes obtained from the spleen of a mammal hyperimmunized with an antigen, such as is present in a polypeptide of this invention. The polypeptide-induced hybridoma technology is described by Niman et al., *Proc. Natl. Acad. Sci. USA*, 80:4949–4953 (1983), which description is incorporated herein by reference.

It is preferred that the myeloma cell line used to prepare a hybridoma be from the same species as the lymphocytes. Typically, a mouse of the strain 129 GIX$^+$ is the preferred mammal. Suitable mouse myelomas for use in the present invention include the hypoxanthine-aminopterin-thymidine-sensitive (HAT) cell lines P3X63-Ag8.653, and Sp2/0-Ag14 that are available from the American Type Culture Collection, Rockville, Md., under the designations CRL 1580 and CRL 1581, respectively.

Splenocytes are typically fused with myeloma cells using polyethylene glycol (PEG) 1500. Fused hybrids are selected by their sensitivity to HAT. Hybridomas producing a monoclonal antibody of this invention are identified using the radioimmunoassay (RIA) and the enzyme linked immunosorbent assay (ELISA) described in Examples 4 and 2, respectively.

A monoclonal antibody of the present invention can also be produced by initiating a monoclonal hybridoma culture comprising a nutrient medium containing a hybridoma that secretes antibody molecules of the appropriate polypeptide specificity. The culture is maintained under conditions and for a time period sufficient for the hybridoma to secrete the antibody molecules into the medium. The antibody-containing medium is then collected. The antibody molecules can then be further isolated by well known techniques.

Media useful for the preparation of these compositions are both well known in the art and commercially available and include synthetic culture media, inbred mice and the like. An exemplary synthetic medium is Dulbecco's minimal essential medium (DMEM; Dulbecco et al., *Virol.* 8:396 (1959)) supplemented with 4.5 gm/l glucose, 20 mm glutamine, and 20% fetal calf serum. An exemplary inbred mouse strain is the Balb/c.

The monoclonal antibodies of this invention can be used in the same manner as disclosed herein for antibodies of the present invention.

For example, the monoclonal antibody can be used in the therapeutic, diagnostic or in vitro methods disclosed herein where inhibition of the corresponding serine protease is desired.

Other methods of producing a monoclonal antibody, a hybridoma cell, or a hybridoma cell culture are also well known. See, for example, the method of isolating monoclonal antibodies from an immunological repertoire as described by Sastry, et al., *Proc. Natl. Acad. Sci. USA*, 86:5728–5732 (1989); and Huse et al., *Science*, 246:1275–1281 (1989).

Also contemplated by this invention is the hybridoma cell, and cultures containing a hybridoma cell that produce a monoclonal antibody of this invention.

D. Diagnostic Systems

The present invention also describes a diagnostic system, preferably in kit form, for assaying for the presence of a serine protease or a polypeptide of this invention in a fluid sample suspected to contain the protein or polypeptide according to the diagnostic methods described herein. A diagnostic system includes, in an amount sufficient for at least one assay, a subject polypeptide and/or a subject antibody or monoclonal antibody of the present invention, as a separately packaged reagent.

In one embodiment, the diagnostic system is useful for assaying for the presence of a polypeptide or anti-polypeptide antibody in a body fluid sample such as for monitoring the fate of therapeutically administered polypeptide or anti-polypeptide antibody.

Instructions for use of the packaged reagent are also typically included.

As used herein, the term "package" refers to a solid matrix or material such as glass, plastic, paper, foil and the like capable of holding within fixed limits a polypeptide, polyclonal antibody or monoclonal antibody of the present invention. Thus, for example, a package can be a glass vial used to contain milligram quantities of a contemplated polypeptide or antibody or it can be a microtiter plate well to which microgram quantities of a contemplated polypeptide have been operatively affixed, i.e., linked so as to be capable of being immunologically bound by an antibody.

"Instructions for use" typically include a tangible expression describing the reagent concentration or at least one assay method parameter such as the relative amounts of reagent and sample to be admixed, maintenance time periods for reagent/sample admixtures, temperature, buffer conditions and the like.

In one embodiment, a diagnostic system for assaying for the presence of or to quantitate a serine protease present in a sample, such as blood, plasma or serum, comprises a package containing at least one antibody of this invention, which is immunoreactive with the serine protease. The system can additionally contain, typically in a separate package, a polypeptide of this invention having a sequence derived from the corresponding serine protease. Exemplary diagnostic systems utilizing an APC inhibitory polypeptide or antibody of this invention are described in Example 5.

A diagnostic system of the present invention can additionally include a label or indicating means capable of signaling the formation of an immunocomplex containing a polypeptide or antibody molecule of the present invention.

The word "complex" as used herein refers to the product of a specific binding reaction such as an antibody-antigen or receptor-ligand reaction. Exemplary complexes are immunoreaction products.

As used herein, the terms "label" and "indicating means" in their various grammatical forms refer to single atoms and molecules that are either directly or indirectly involved in the production of a detectable signal to indicate the presence of a complex. Any label or indicating means can be linked to or incorporated in an expressed protein, polypeptide, or antibody molecule that is part of an antibody or monoclonal antibody composition of the present invention, or used separately, and those atoms or molecules can be used alone or in conjunction with additional reagents. Such labels are themselves well-known in clinical diagnostic chemistry and constitute a part of this invention only insofar as they are utilized with otherwise novel proteins methods and/or systems.

The labeling means can be a fluorescent labeling agent that chemically binds to antibodies or antigens without denaturing them to form a fluorochrome (dye) that is a useful immunofluorescent tracer. Suitable fluorescent labeling agents are fluorochromes such as fluorescein isocyanate (FIC), fluorescein isothiocyanate (FITC), 5-dimethylamine-1-naphthalenesulfonyl chloride (DANSC), tetramethylrhodamine isothiocyanate (TRITC), lissamine, rhodamine 8200 sulphonyl chloride (R 8200 SC) and the like. A description of immunofluorescence analysis techniques is found in DeLuca, "Immunofluorescence Analysis", in *Antibody As a Tool*, Marchalonis, et al., eds., John Wiley & Sons, Ltd., pp. 189–231 (1982), which is incorporated herein by reference.

In preferred embodiments, the indicating group is an enzyme, such as horseradish peroxidase (HRP), glucose oxidase, or the like. In such cases where the principal indicating group is an enzyme such as HRP or glucose oxidase, additional reagents are required to visualize the fact that a receptor-ligand complex (immunoreactant) has formed. Such additional reagents for HRP include hydrogen peroxide and an oxidation dye precursor such as diaminobenzidine. An additional reagent useful with glucose oxidase is 2,2'-amino-di-(3-ethyl-benzthiazoline-G-sulfonic acid) (ABTS).

Radioactive elements are also useful labeling agents and are used illustratively herein. An exemplary radiolabeling agent is a radioactive element that produces gamma ray emissions. Elements which themselves emit gamma rays, such as $^{124}I$, $^{125}I$, $^{128}I$, $^{132}I$ and $^{51}Cr$ represent one class of gamma ray emission-producing radioactive element indicating groups. Particularly preferred is $^{125}I$. Another group of useful labeling means are those elements such as $^{11}C$, $^{18}F$, $^{15}O$ and $^{13}N$ which themselves emit positrons. The positrons so emitted produce gamma rays upon encounters with electrons present in the animal's body. Also useful is a beta emitter, such as $^{111}$indium or $^3H$.

The linking of labels, i.e., labeling of, polypeptides and proteins is well known in the art. For instance, antibody molecules produced by a hybridoma can be labeled by metabolic incorporation of radioisotope-containing amino acids provided as a component in the culture medium. See, for example, Galfre et al., *Meth. Enzymol.*, 73:3–46 (1981). The techniques of protein conjugation or coupling through activated functional groups are particularly applicable. See, for example, Aurameas, et al., *Scand. J. Immunol.*, Vol. 8 Suppl. 7:7–23 (1978), Rodwell et al., *Biotech.*, 3:889–894 (1984), and U.S. Pat. No. 4,493,795.

The diagnostic systems can also include, preferably as a separate package, a specific binding agent. A "specific binding agent" is a molecular entity capable of selectively binding a reagent species of the present invention or a complex containing such a species, but is not itself a polypeptide or antibody molecule composition of the present invention. Exemplary specific binding agents are second antibody molecules, complement proteins or fragments thereof, *S. aureus* protein A, and the like. Preferably the specific binding agent binds the reagent species when that species is present as part of a complex.

In preferred embodiments, the specific binding agent is labeled. However, when the diagnostic system includes a specific binding agent that is not labeled, the agent is typically used as an amplifying means or reagent. In these embodiments, the labeled specific binding agent is capable of specifically binding the amplifying means when the amplifying means is bound to a reagent species-containing complex.

The diagnostic kits of the present invention can be used in an "ELISA" format to detect the quantity of an APC inhibitor of this invention in a vascular fluid sample such as blood, serum, or plasma. "ELISA" refers to an enzyme-linked immunosorbent assay that employs an antibody or antigen bound to a solid phase and an enzyme-antigen or enzyme-antibody conjugate to detect and quantify the amount of an antigen present in a sample. A description of the ELISA technique is found in Chapter 22 of the 4th Edition of *Basic and Clinical Immunology* by D. P. Sites et al., published by Lange Medical Publications of Los Altos, Calif. in 1982 and in U.S. Pat. No. 3,654,090; U.S. Pat. No. 3,850,752; and U.S. Pat. No. 4,016,043, which are all incorporated herein by reference.

Thus, in some embodiments, a polypeptide or a monoclonal antibody of the present invention can be affixed to a solid matrix to form a solid support that comprises a package in the subject diagnostic systems.

A reagent is typically affixed to a solid matrix by adsorption from an aqueous medium although other modes of affixation applicable to proteins and polypeptides well known to those skilled in the art, can be used.

Useful solid matrices are also well known in the art. Such materials are water insoluble and include the cross-linked dextran available under the trademark SEPHADEX from Pharmacia Fine Chemicals (Piscataway, N.J.); agarose; beads of polystyrene beads about 1 micron to about 5 millimeters in diameter available from Abbott Laboratories of North Chicago, Ill.; polyvinyl chloride, polystyrene, cross-linked polyacrylamide, nitrocellulose- or nylon-based webs such as sheets, strips or paddles; or tubes, plates or the wells of a microtiter plate such as those made from polystyrene or polyvinylchloride.

The reagent species, labeled specific binding agent or amplifying reagent of any diagnostic system described herein can be provided in solution, as a liquid dispersion or as a substantially dry powder, e.g., in lyophilized form. Where the indicating means is an enzyme, the enzyme's substrate can also be provided in a separate package of a system. A solid support such as the before-described microtiter plate and one or more buffers can also be included as separately packaged elements in this diagnostic assay system.

The packaging materials discussed herein in relation to diagnostic systems are those customarily utilized in diagnostic systems.

The term "package" refers to a solid matrix or material such as glass, plastic (e.g., polyethylene, polypropylene and polycarbonate), paper, foil and the like capable of holding within fixed limits a diagnostic reagent such as a polypeptide, antibody or monoclonal antibody of the present invention. Thus, for example, a package can be a bottle, vial, plastic and plastic-foil laminated envelope or the like container used to contain a contemplated diagnostic reagent or it can be a microtiter plate well to which microgram quantities of a contemplated diagnostic reagent have been operatively affixed, i.e., linked so as to be capable of being immunologically bound by an antibody or polypeptide to be detected.

E. Assay Methods

The present invention contemplates various assay methods for determining the presence, and preferably amount, of an antigen such as a serine protease, a polypeptide or an antibody of the present invention in a fluid sample using a polypeptide, polyclonal antibody or monoclonal antibody of this invention as an immunochemical reagent to form an immunoreaction product whose amount relates, either directly or indirectly, to the amount of the antigen in the sample. This embodiment is particularly useful to monitor the fate of therapeutically administered polypeptides or antibodies as described in the therapeutic methods herein.

Those skilled in the art will understand that there are numerous well known clinical diagnostic chemistry procedures in which an immunochemical reagent of this invention can be used to form an immunoreaction product whose amount relates to the amount of an antigen to be measured that is present in a body sample. Thus, while exemplary assay methods are described herein, the invention is not so limited.

Various heterogenous and homogeneous protocols, either competitive or noncompetitive, can be employed in performing an assay method of this invention. Typically, the present assay method comprises the steps of:

(a) Forming an immunoreaction admixture by admixing a vascular fluid sample with an anti-polypeptide antibody of the present invention, preferably a monoclonal antibody, or a polypeptide of the present invention.

Insofar as immunoassay depends on the specific reactivity of antigen and antibody, the selection of polypeptide or antibody depends on the species of serine protease or protease-derived antibody of polypeptide to be detected. Thus, for example, if the assay is designed to detect Factor X, an antibody produced using a Factor X-derived polypeptide is admixed with the sample.

Similarly, where the fluid sample contains a polypeptide, an anti-polypeptide antibody immunospecific for the polypeptide is added to form the immunoreaction admixture. Where the fluid sample contains an anti-polypeptide antibody, a polypeptide of this invention used to produce the antibody, or immunoreactive with the antibody is added to form the immunoreaction admixture.

Preferably, the fluid sample is provided as a known amount of blood, or a blood derived product such as serum or plasma.

Preferably, the amount of antibody or polypeptide as immunochemical reagent that is admixed is known. Further preferred are embodiments where the antibody is labeled, i.e., operatively linked to an indicating means such as an enzyme, radionuclide and the like.

In preferred embodiments, the immunochemical reagent is present as part of a solid support, i.e., operatively linked to a solid matrix, so that the immunoreaction admixture formed has a solid and a liquid phase and the immunochemical reagent functions as a capture reagent. Further preferred are embodiments wherein the amount of polypeptide present in the immunoreaction admixture is an amount sufficient to form an excess of epitopes relative to the number of antibody combining sites present in the immunoreaction admixture capable of immunoreacting with those epitopes.

(b) The immunoreaction admixture is maintained under biological assay conditions for a predetermined time period such as about 10 minutes to about 16–20 hours at a temperature of about 4 degrees C. to about 45 degrees C. that, such time being sufficient for the APC inhibitor present in the sample to immunoreact with (immunologically bind) the immunochemical reagent to form an antigen-containing immunoreaction product (immunocomplex) containing the target antigen immunoreacted with the immunochemical reagent. In embodiments where the immunochemical reagent is in the solid phase, the immunocomplex formed is also present in the solid phase.

Biological assay conditions are those that maintain the biological activity of the immunochemical reagents of this invention and the antigen sought to be assayed. Those conditions include a temperature range of about 4 degrees C. to about 45 degrees C., a pH value range of about 5 to about 9 and an ionic strength varying from that of distilled water to that of about one molar sodium chloride. Methods for optimizing such conditions are well known in the art.

(c) The amount of antigen-containing immunoreaction product that formed in step (b) is determined, thereby determining the amount of preselected antigen present in the sample.

Determining the amount of the antigen-containing immunoreaction product, either directly or indirectly, can be accomplished by assay techniques well known in the art, and typically depend on the type of indicating means used.

In preferred competitive assay methods, the amount of product determined in step (c) is related to the amount of immunoreaction product similarly formed and determined using a control sample in place of the vascular fluid sample, wherein the control sample contains a known amount of a subject polypeptide or antibody from which a standard curve is determined.

Exemplary of the contemplated diagnostic assay, wherein a polypeptide immunoreactive with the antibody reagent is operatively linked to a solid matrix is the ELISA described in Example 2.

Also contemplated are immunological assays capable of detecting the presence of immunoreaction product formation without the use of a label. Such methods employ a "detection means", which means are themselves well-known in clinical diagnostic chemistry and constitute a part of this invention only insofar as they are utilized with otherwise novel polypeptides, methods and systems. Exemplary detection means include methods known as biosensors and include biosensing methods based on detecting changes in the reflectivity of a surface, changes in the absorption of an evanescent wave by optical fibers or changes in the propagation of surface acoustical waves.

Thus, in one embodiment, the invention contemplates a method for detecting the presence of a protein C antigen, such as protein C or a protein C-derived polypeptide of this invention in a fluid sample comprising the steps of:

(a) forming an immunoreaction admixture by admixing the fluid sample with an anti-protein C polypeptide antibody of this invention comprising antibody molecules that immunoreact with (i) protein C, and with (ii) a polypeptide having an amino acid residue sequence represented by the formula selected from the group consisting of (1:311–325) and (1:142–155); but do not immunoreact with the polypeptide having an amino acid residue sequence represented by the formula: (1:266–287);

(b) maintaining the immunoreaction admixture for a time period sufficient to form a protein C antigen-containing immunoreaction product; and (c) detecting the presence of immunoreaction product formed in step (b) and thereby the presence of protein C antigen in the fluid sample.

In one embodiment of the above assay for detecting a protein C antigen, the antibody immunoreacts with the polypeptide represented by the formula (1:311–325) and the protein C antigen is a polypeptide that includes an amino acid residue sequence selected from the group consisting of (1:311–325) and (1:311–331).

In another embodiment of the above assay for detecting a protein C antigen, the antibody immunoreacts with the polypeptide represented by the formula (1:142–155) and the protein C antigen is a polypeptide that includes an amino acid residue sequence represented by the formula (1:142–155).

A related assay for detecting the presence of a Factor IX antigen, such as Factor IX, IXa or a IX-derived polypeptide of this invention in a fluid sample comprises the steps of:

(a) forming an immunoreaction admixture by admixing the fluid sample with an anti-Factor IX polypeptide antibody of this invention comprising antibody molecules that immunoreact with (i) Factor IX, and with (ii) a polypeptide having an amino acid residue sequence represented by the formula selected from the group consisting of (2:316–330), (2:321–330), (2:395–409), (2:400–409) and (2:400–414); but do not immunoreact with the polypeptide having an amino acid residue sequence represented by the formula: (2:271–292);

(b) maintaining the immunoreaction admixture for a time period sufficient to form a Factor IX antigen-containing immunoreaction product; and (c) detecting the presence of immunoreaction product formed in step (b) and thereby the presence of Factor IX antigen in the fluid sample.

In one embodiment of the above assay for detecting a Factor IX antigen, the antibody immunoreacts with the polypeptide represented by the formula (2:321–330) and the Factor IX antigen is a polypeptide that includes an amino acid residue sequence selected from the group consisting of (2:316–330) and (2:321–330).

In another embodiment of the above assay for detecting a Factor IX antigen, the antibody immunoreacts with the polypeptide represented by the formula (2:395–409), (2:400–409) or (2:400–414) and the Factor IX antigen is a polypeptide that includes an amino acid residue sequence represented by the formula (2:395–409), (2:400–409) or (2:400–414), respectively.

In a related assay for detecting the presence of a Factor X antigen, such as Factor X, Xa or a IX-derived polypeptide of this invention in a fluid sample the invention method comprises the steps of:

(a) forming an immunoreaction admixture by admixing the fluid sample with an anti-Factor X polypeptide antibody of this invention comprising antibody molecules that immunoreact with (i) Factor X, and with (ii) a polypeptide having an amino acid residue sequence represented by the formula selected from the group consisting of (3:330–344), (3:404:418) and (3:415–429); but do not immunoreact with the polypeptide having an amino acid residue sequence represented by the formula: (3:285–306).

(b) maintaining the immunoreaction admixture for a time period sufficient to form a Factor X antigen-containing immunoreaction product; and (c) detecting the presence of immunoreaction product formed in step (b) and thereby the presence of Factor X antigen in the fluid sample.

In one embodiment of the above assay for detecting a Factor X antigen, the antibody immunoreacts with the polypeptide represented by the formula (3:330–344) and the Factor X antigen is a polypeptide that includes an amino acid residue sequence selected from the group consisting of (3:329–344), (3:330–334) and (3:330–350).

In another embodiment of the above assay for detecting a Factor X antigen, the antibody immunoreacts with the polypeptide represented by the formula (3:404:418) or (3:415–429) and the Factor X antigen is a polypeptide that includes an amino acid residue sequence represented by the formula (3:404:418) or (3:415–429), respectively.

In another related assay method for detecting the presence of a prothrombin antigen, such as prothrombin, thrombin or a prothrombin-derived polypeptide of this invention in a fluid sample the invention method comprises the steps of:
- (a) forming an immunoreaction admixture by admixing the fluid sample with an anti-prothrombin polypeptide antibody of this invention comprising antibody molecules that immunoreact with (i) prothrombin, and with (ii) a polypeptide having an amino acid residue sequence represented by the formula selected from the group consisting of (4:463–477), (4:474–487), (4:481–495) and (4:557–571); but do not immunoreact with the polypeptide having an amino acid residue sequence represented by the formula: (4:429–450)
- (b) maintaining the immunoreaction admixture for a time period sufficient to form a prothrombin antigen-containing immunoreaction product; and
- (c) detecting the presence of immunoreaction product formed in step (b) and thereby the presence of prothrombin antigen in the fluid sample.

In one embodiment of the above assay for detecting a prothrombin antigen, the antibody immunoreacts with the polypeptide represented by the formula (4:463–477), (4:474–487), (4:481–495) and (4:557–571) and the prothrombin antigen is a polypeptide that includes an amino acid residue sequence selected from the group consisting of (4:463–477), (4:474–487), (4:481–495) and (4:557–571), respectively.

An additional related assay method for detecting the presence of a Factor VII antigen, such as Factor VII, Factor VIIa or a Factor VII-derived polypeptide of this invention in a fluid sample the invention method comprises the steps of:
- (a) forming an immunoreaction admixture by admixing the fluid sample with an anti-Factor VII polypeptide antibody of this invention comprising antibody molecules that immunoreact with (i) Factor VII, and with (ii) a polypeptide having an amino acid residue sequence represented by the formula selected from the group consisting of (5:289–304), (5:290–304), (5:290–310) and (5:374–388); but do not immunoreact with the polypeptide having an amino acid residue sequence represented by the formula: (5:245–266)
- (b) maintaining the immunoreaction admixture for a time period sufficient to form a Factor VII antigen-containing immunoreaction product; and
- (c) detecting the presence of immunoreaction product formed in step (b) and thereby the presence of Factor VII antigen in the fluid sample.

In one embodiment of the above assay for detecting a Factor VII antigen, the antibody immunoreacts with the polypeptide represented by the formula (5:289–304), (5:290–304), (5:290–310) and (5:374–388) and the Factor VII antigen is a polypeptide that includes an amino acid residue sequence selected from the group consisting of (5:289–304), (5:290–304), (5:290–310) and (5:374–388), respectively.

The present invention also contemplates a diagnostic method for detecting the presence in a fluid sample of an antibody that immunoreacts with a blood coagulation serine protease comprising the steps of:
- (a) forming an immunoreaction admixture by admixing a fluid sample with a polypeptide of the present invention derived from one of the blood coagulation serine proteases;
- (b) maintaining said immunoreaction admixture for a time period sufficient to form an immunoreaction product containing said polypeptide; and
- (c) determining the presence of the immunoreaction product formed in step (b), and thereby the presence of said antibody.

The above diagnostic assay methods for detecting the presence, and preferably the amount of, the indicated antigens can readily be applied to the other serine proteases, and to the anti-polypeptide antibodies and polypeptides of the invention described elsewhere herein, and generally follow the protocols outlined above.

F. Therapeutic Compositions

The present invention contemplates therapeutic compositions useful for practicing the therapeutic methods described herein. Therapeutic compositions of the present invention contain a physiologically tolerable carrier together with an APC inhibitor, namely a polypeptide, an anti-polypeptide antibody or monoclonal antibody as described herein, dissolved or dispersed therein as an active ingredient. In a preferred embodiment, the therapeutic composition is not immunogenic when administered to a mammal or human patient for therapeutic purposes.

As used herein, the terms "pharmaceutically acceptable", "physiologically tolerable" and grammatical variations thereof, as they refer to compositions, carriers, diluents and reagents, are used interchangeably and represent that the materials are capable of administration to or upon a mammal without the production of undesirable physiological effects such as nausea, dizziness, gastric upset and the like.

The preparation of a pharmacological composition that contains active ingredients dissolved or dispersed therein is well understood in the art. Typically such compositions are prepared as injectables either as liquid solutions or suspensions, however, solid forms suitable for solution, or suspensions, in liquid prior to use can also be prepared. The preparation can also be emulsified.

The active ingredient can be mixed with excipients which are pharmaceutically acceptable and compatible with the active ingredient and in amounts suitable for use in the therapeutic methods described herein. Suitable excipients are, for example, water, saline, dextrose, glycerol, ethanol or the like and combinations thereof. In addition, if desired, the composition can contain minor amounts of auxiliary substances such as wetting or emulsifying agents, pH buffering agents and the like which enhance the effectiveness of the active ingredient.

The therapeutic composition of the present invention can include pharmaceutically acceptable salts of the components therein. Pharmaceutically acceptable salts include the acid addition salts (formed with the free amino groups of the polypeptide) that are formed with inorganic acids such as, for example, hydrochloric or phosphoric acids, or such organic acids as acetic, tartaric, mandelic and the like. Salts formed with the free carboxyl groups can also be derived from inorganic bases such as, for example, sodium, potassium, ammonium, calcium or ferric hydroxides, and such organic bases as isopropylamine, trimethylamine, 2-ethylamino ethanol, histidine, procaine and the like.

Physiologically tolerable carriers are well known in the art. Exemplary of liquid carriers are sterile aqueous solutions that contain no materials in addition to the active ingredients and water, or contain a buffer such as sodium phosphate at physiological pH value, physiological saline or both, such as phosphate-buffered saline. Still further, aqueous carriers can contain more than one buffer salt, as well as salts such as sodium and potassium chlorides, dextrose, polyethylene glycol and other solutes.

Liquid compositions can also contain liquid phases in addition to and to the exclusion of water. Exemplary of such additional liquid phases are glycerin, vegetable oils such as cottonseed oil, and water-oil emulsions.

A therapeutic composition contains an serine protease inhibiting amount of polypeptide or antibody inhibitor of the present invention, typically an amount of at least 0.1 weight percent of inhibitor per weight of total therapeutic composition. A weight percent is a ratio by weight of inhibitor to total composition. Thus, for example, 0.1 weight percent is 0.1 grams of inhibitor per 100 grams of total composition.

The selection of the polypeptide species or antibody species for use in a therapeutic composition will vary depending on the serine protease to be inhibited.

The polypeptides and antibodies described herein as being derived from the blood coagulation factors, namely Factor VIIa, Factor IXa, Factor Xa, Factor XIa, and thrombin are exemplary of the present invention, but the therapeutic compositions need not be so limited.

A therapeutic composition can contain one or more species of polypeptide derived as described herein from a single serine protease, or can contain a combination of polypeptides derived as described herein from different serine proteases, which peptides are defined herein.

Similarly, the composition can contain one or more species of anticoagulant antibodies as defined herein.

In one particularly preferred embodiment for inhibiting blood coagulation, a therapeutic composition is comprised of one or more polypeptides derived from the serine proteases Factor VIIa, Factor IXa, Factor Xa, Factor XIa, plasma kallikrein and thrombin as described herein.

G. Therapeutic Methods

It has been discovered that the polypeptides, antibodies, and monoclonal antibodies of the present invention (i.e., serine protease inhibitors) have the capacity to inhibit serine proteases.

In addition, due to the physiological role of the blood coagulation serine proteases in contributing to the coagulation of blood, inhibition of the blood coagulation factors in vitro or in vivo will inhibit the level of coagulation occurring in vitro or in vivo.

Thus, the present invention provides for a method for inhibiting coagulation of blood products in a patient comprising administering to the patient a therapeutically effective amount of a physiologically tolerable composition containing a coagulation inhibitor of this invention, namely a polypeptide, antibody, or monoclonal antibody of the present invention that is derived from a blood coagulation serine protease as described herein.

A therapeutically effective amount of a coagulation inhibitor is a predetermined amount calculated to achieve the desired effect, i.e., to inhibit the in vivo the serine proteases that participate in blood coagulation in said patient and thereby decrease the amount of ongoing or potential coagulation activity present in the patient.

A typical clinical setting for in vivo inhibition of coagulation is when a patient exhibits disseminated intravascular coagulation (DIC), septic shock, venous or arterial thrombosis and the like conditions requiring anticoagulant intervention.

A therapeutically effective amount of a polypeptide of this invention is typically an amount of polypeptide such that when administered in a physiologically tolerable composition is sufficient to achieve a plasma concentration of from about 0.1 micromolar (uM) to about 100 uM, and preferably from about 0.5 uM to about 10 uM.

A therapeutically effective amount of an antibody of this invention is typically an amount of antibody such that when administered in a physiologically tolerable composition is sufficient to achieve a plasma concentration of from about 0.1 microgram (ug) per milliliter (ml) to about 100 ug/ml, preferably from about 1 ug/ml to about 5 ug/ml, and usually about 5 ug/ml.

The level of inhibition of coagulation present in a patient indicative of the efficacy of inhibition therapy can be readily determined by routine clinical analysis. Exemplary assays to monitor the level of one or more of the factors that contribute to the coagulation process are described herein.

The therapeutic compositions containing a coagulation inhibitor of this invention are conventionally administered intravenously, as by injection of a unit dose, for example. The term "unit dose" when used in reference to a therapeutic composition of the present invention refers to physically discrete units suitable as unitary dosage for the subject, each unit containing a predetermined quantity of active material calculated to produce the desired therapeutic effect in association with the required diluent; i.e., carrier, or vehicle.

The compositions are administered in a manner compatible with the dosage formulation, and in a therapeutically effective amount. The quantity to be administered depends on the subject to be treated, capacity of the subject's system to utilize the active ingredient, and degree of therapeutic effect desired. Precise amounts of active ingredient required to be administered depend on the judgement of the practitioner and are peculiar to each individual. However, suitable dosage ranges for systemic application are disclosed herein and depend on the route of administration. Suitable regimes for initial administration and booster shots are also variable, but are typified by an initial administration followed by repeated doses at one or more hour intervals by a subsequent injection or other administration. Alternatively, continuous intravenous infusion sufficient to maintain concentrations in the blood in the ranges specified for in vivo therapies are contemplated.

As an aid to the administration of effective amounts of a polypeptide, antibody, or monoclonal antibody of this invention, a diagnostic method for detecting a anticoagulant polypeptide, antibody, or monoclonal antibody, respectively, in the subject's blood is useful to characterize the fate of the administered therapeutic composition. Suitable diagnostic methods are also described herein.

The invention also contemplates in vitro methods for inhibiting serine proteases in an aqueous composition such as a liquid protein admixture or a blood, plasma or serum sample.

In this embodiment the method comprises contacting the aqueous composition with a serine protease-inhibiting amount of a polypeptide or antibody of this invention.

In particular the invention contemplates a method for inhibiting the proteases of the coagulation cascade. In this embodiment the method comprises contacting the aqueous composition with a coagulation-inhibiting amount of a polypeptide or antibody of the present invention.

As used herein, the phrase "contacting" refers to a variety of means which results in allowing the inhibitor, namely the polypeptide, antibody, or monoclonal antibody of the present invention, to come into contact with the serine protease in the aqueous composition under physiological conditions. Such means include, but are not limited to admixture of the inhibitor with the composition to form a serine protease inhibition admixture comprising a liquid phase:liquid phase or solid matrix:liquid phase admixture, or by introduction of the inhibitor by injection, infusion, implantation and the like into a donor prior to harvesting the plasma containing the proteases to be inhibited.

The phrase "coagulation-inhibiting amount", refers to an amount of a polypeptide, antibody, or monoclonal antibody sufficient to measurably inhibit the activity present in the plasma or other source material containing the protease to be inhibited, preferably an amount of inhibition of at least about 10 percent, more preferably at least about 50 percent and most preferably at least about 100 percent of the detectable serine protease activity. A contemplated dosage amount is within the range of about $10^{-7}$ molar to $10^{-2}$ molar polypeptide, and about 10 to 1000 nanomolar antibody. The polypeptide, antibody or monoclonal antibody is typically administered as a pharmaceutical composition in the form of a solution or suspension. However, as is well known, a polypeptide, antibody, or monoclonal antibody either alone or in admixture, can also be formulated for therapeutic administration as a tablet, pill, capsule, aerosol, sustained release formulation or powder.

EXAMPLES

The following description provides details of the manner in which particular embodiments of the present invention may be made and used. This description, while exemplary of the present invention, is not to be construed as specifically limiting the invention. Variations and equivalents, now known or later developed, which would be within the understanding and technical competence of one skilled in this art are to be considered as falling within the scope of this invention.

1. Polypeptides

Overlapping synthetic protein C peptides from the heavy chain of protein C listed in Table 3 in the Detailed Description were produced by the simultaneous multiple peptide synthesis method using the solid-phase technique described by Houghten, *Proc. Natl. Acad. Sci. USA*, 82:5131–5135 (1985). All peptides were synthesized in the carboxy-terminal amide form. The synthesized peptides were then analyzed by reverse phase high performance liquid chromatography (HPLC) on a Vydac C-18 column (Alltech Associates, Inc., Illinois) with a 0–60% acetonitrile linear gradient in 0.1% trifluoroacetic acid. Peptides were then purified to homogeneity by preparative HPLC using optimal conditions suggested by the analytical chromatography. In order to prevent disulfide formation among peptides, in some peptides the originally occurring cysteine was substituted by a serine or a glycine amino acid residue as indicated in Table 3 shown in the Detailed Description. Amino acid compositions and concentrations of isolated peptides were determined by subjection to 24 hour hydrolysis in 6N HCl in evacuated tubes at 110 degrees Celsius (110° C.) and subsequent analysis on a Beckman Model 6300 High Performance Analyzer. Mass spectroscopic analyses of PC317-331 (SEQ ID NO 1) and 311-325 (SEQ ID NO 1) using the FIB positive ion mass spectra obtained on a VG-ZAB-VSE double focusing mass spectrometer equipped with a cesium ion gun yielded a single peak and the exact expected molecular weight of 1721 for the single protonated form of PC317-33) (SEQ ID NO 1) and 1845 for the single protonated form of PC311-325) (SEQ ID NO 1).

Purified peptides were separately resuspended in distilled water to form a dissolved peptide solution at a final concentration of 2.5 mM. Subsequently, one-tenth volume of 10-fold concentrated buffer containing 0.05M Tris hydroxymethyl aminomethanehydrochloride (Tris-HCl) at pH 7.4 (TBS-Az), 0.1M sodium chloride (NaCl) and 0.02% sodium azide ($NaN_3$) was added. The pH of the solution was checked, and if necessary, adjusted to pH 7.4 with titrated amounts of 1M Tris-base. For peptides that appeared to not be completely soluble at 2.5 mM in TBS-Az, the partially dissolved peptide suspensions were separately centrifuged at 13,000×g to pellet the insoluble material. The molar concentrations in the resultant individual supernatants were estimated from the absorbance at 280 nm and 257 nm, respectively, for peptide solutions containing aromatic amino acids using a molar extinction coefficient of 5,600 $M^{-1}cm^{-1}$ for tryptophan and 1,400 $M^{-1}cm^{-1}$ for tyrosine at 280 nm, using a molar extinction coefficient of 200 $M^{-1}cm^{-1}$ for phenylalanine at 257 nm. The concentration of PC311-325 was estimated using a molar extinction coefficient of 400 $M^{-1}$ $cm^{-1}$.

The sequence of the control peptide with a randomized sequence of residue 311–325 was obtained by randomly drawing 15 individual labeled folded pieces of paper, each paper representing one residue. The sequence of drawing each amino acid dictated the random order of amino acids. This peptide had the sequence, VKFTIRVFNPRNLKI (SEQ ID NO 8), and was designated as control peptide. Mass spectroscopic analyses of PC311-325 and the control peptide yielded in each case single peaks and the exact expected molecular weight of 1845 for the single protonated form of PC311-325 and the control peptide, respectively. Solutions of each peptide were prepared and the concentrations were determined using a molar extinction coefficient of 400 $m^{-1}cm^{-1}$ for PC311-325 as well as for the control peptide with the randomized sequence.

Following purification to homogeneity by reverse phase-HPLC, PC142-155 did not have the exact expected mass judged by mass-spectroscopy. For this reason, PC142-155 was synthesized with an additional carboxy-terminal cysteine in able to purify this peptide to homogeneity obtaining the correct mass. Unless otherwise specified, only this peptide with an additionally introduced carboxy-terminal cysteine is designated as PC142-155. The sequence of the scrambled peptide with a randomized sequence of residue 142–155 in PC was obtained by randomly drawing 14 individual labeled folded pieces of paper, each paper representing one residue. The resultant scrambled peptide had the sequence, MHKLREGKWRPKSR (SEQ ID NO 9), and was designated as scrambled peptide. Mass spectroscopic analyses of PC142-155 and the scrambled peptide yielded in each case the exact expected molecular weight of 1911 for the single protonated form of PC142-155 and 1809 for the scrambled peptide. Solutions of each peptide were prepared and the concentrations were determined using a molar extinction coefficient of 5,600 $M^{-1}cm^{-1}$ for PC142-155 as well as for the scrambled peptide. Peptides without aromatic amino acids and poor solubility in aqueous solutions were not evaluated in this invention.

2. Preparation of Polyclonal Antisera to Synthetic Polypeptides a. Preparation of Immunogen For preparation of a peptide immunogen, the synthetic PC317-331 (SEQ ID NO 1) was prepared as described in Example 1 but was modified with a carboxy-terminal cysteine. The synthesized PC317-331 was coupled to keyhole-limpet-hemocyanin (KLH) (Sigma, St. Louis, Mo.) using the heterobifunctional crosslinking agent, N-succinimidyl-3-(2-pyridyldithio)propionate (SPDP) (Pierce Biochemicals, Rockford, Ill.). For the coupling procedure, 80 microliters (µl) of 10 milligrams/milliliter (mg/ml) SPDP dissolved in dimethylformamide was admixed dropwise to 400 µl 15 mg/ml KLH in 0.1M phosphate containing 0.1M NaCl at pH 8.5 under continuous stirring conditions for 30 minutes at 22° C. in order to form SPDP-activated KLH. The resultant SPDP-activated KLH was then extensively dialyzed at 4° C. against a buffered solution of 0.1M phosphate containing 0.1M NaCl at pH 7.4 in order to remove uncoupled SPDP. Six mg of prepared PC317-331 having a C-terminal cysteine was first dissolved in 2 ml of 0.1M phosphate and 0.1M NaCl at pH 7.4 and then admixed with SPDP-activated KLH prepared above under continuous stirring conditions. The degree of coupling of PC317-331 with KLH was monitored by the pyridine-2-thione release at 343 nm ($\epsilon$: $8.08 \times 10^3 \, M^{-1} \, cm^{-1}$) in a spectrophotometer.

PC142-155 was also prepared as an immunogen as described for PC317-331 to form PC142-155-KLH. This preparation was used to immunize rabbits as described in b. below.

b. Immunization and Collection of Polyclonal Antisera

The PC316-331-KLH and PC142-155-KLH immunogens prepared in Example 2a were separately emulsified using Adjuvant Complete Freund (DIFCO Laboratories, Detroit, Mich.) for the first injection and Adjuvant Incomplete Freund (DIFCO) for all subsequent injections according to the manufacturer's instructions, and the PC317-331-KLH and PC142-155-KLH antigens were separately incorporated into the emulsion at a concentration of 2 mg/ml. One-half ml of each prepared emulsion was injected subcutaneously into each of two New Zealand white rabbits after pre-immune serum samples were collected. The rabbits were injected three times at weekly intervals following the injection protocol as detailed. Two weeks after the last injection, blood samples were collected to check antibody titer against the specific PC317-331 or PC142-155 used as an immunogen by the ELISA assay described below. The collected blood samples were stored at 4° C. for 12 hours, after which the samples were centrifuged at 3000×g for 20 minutes. The resultant supernatant containing anti-peptide antibodies was collected and stored at −20° C.

The remaining peptides listed in Table 3 are also separately prepared as immunogens by conjugation with KLH as described in Example 2a. Immunization of separate rabbits for the production of antisera against each of the peptides listed above is performed as described herein. The resultant antisera are then screened by ELISA as described for anti-PC317-331 antisera in Example 2c.

c. ELISA to Screen Antisera Immunoreactivity

The peptide antibody titers and immunospecificity in sera collected from rabbits in Example 2b were determined in an enzyme-linked-immunosorbent-assay (ELISA) as described below. The antigens used in the ELISA included the immunizing peptides, PC317-331 and PC142-155, human protein C (PC) and activated Protein C (APC). The preparations of the latter two antigens are described below.

1) preparation of Human PC

Human PC used in the ELISA assay was purified from plasma factor IX concentrate by affinity chromatography on a calcium-dependent, polyclonal, immunoaffinity-purified sheep anti-PC antibody column. The antibody affinity column was prepared by first obtaining the IgG fraction of polyclonal sheep anti-human-PC antibody. The polyclonal sheep anti-human PC antibody was obtained by subcutaneously immunizing sheep with purified human protein C in the presence of calcium following boosting procedures as described in Example 2b. Plasma from immunized sheep was obtained by plasmapheresis of citrate-anticoagulated blood. Purification of the IgG fraction from the sheep plasma was achieved by ammonium-sulfate precipitation (50%) followed by purification of IgG on an ion-exchange DEAE Sephadex column (Pharmacia, Piscataway, N.J.). The resultant IgG fraction of polyclonal sheep anti-human PC antibody was further purified by column chromatography on a PC-Sepharose column.

For preparing the PC-Sepharose column, human PC was first purified from plasma factor IX concentrate using immunoaffinity chromatography as follows. Anti-human PC light-chain monoclonal antibodies, designated C3, as described by Heeb et al., Thrombosis Res., 52:33–43 (1988), were coupled to cyanogenbromide (CNBr)-activated Sepharose 4B (Pharmacia) at a concentration of 3 mg protein to 1 ml gel in coupling buffer (0.5M NaCl and 0.05M borate at pH 8.5) overnight at 4° C. to form a C3 antibody-Sepharose suspension. The suspension was packed into a column and washed with coupling buffer to remove unbound antibody according to manufacturer's instructions. Factor IX concentrate which was obtained from Dr. Hans Peter Schwarz, Immuno AG, Vienna, Austria, consisted of the following components in one gram (g) of bulk powder: protein-740 mg/g; sodium-citrate-47 mg/g; NaCl-77 mg/g; Factor II-1540 units/g; Factor IX-927 units/g; and Factor X-1119 units/g. The Factor IX was admixed with a buffer solution containing 0.1M NaCl, 2 mM ethylene diamine tetraacetic acid (EDTA), 2 mM benzamidine, 0.02% $NAN_3$, 0.02% Tween-20 and 0.02M Tris-HCl at pH 7.4.

The buffered Factor IX concentrate was then passed over the prepared C3-Sepharose antibody column to immobilize human PC on the antibody column and separate PC from non-PC contaminants. The antibody column containing immobilized PC was subsequently washed to further remove unbound proteins. Immobilized PC was then eluted from the column with 3M sodium thiocyanate (NaSCN) in 1.0M NaCl, 4 mM benzamidine, 2 mM EDTA, 0.02% $NAN_3$, 0.05% Tween-20 and 0.05M Tris-HCl at pH 7.0. The eluted and purified PC was determined to be greater than 95% pure when analyzed using sodium dodecyl sulfate-polyacrylamide gel electrophoresis (SDS-PAGE).

The purified human PC was then coupled to Sepharose 4B as described above to form an antigen column for purifying the IgG fraction of polyclonal sheep anti-human PC antibody described above. The sheep anti-human-PC antibody in TBS buffer at pH 7.4 containing 5 mM calcium chloride ($CaCl_2$) was admixed to the human PC-Sepharose column for immobilization of anti-PC specific antibodies. The calcium-dependent anti-PC antibodies immobilized on the PC-Sepharose column were then eluted with TBS containing 20 mM EDTA. The eluted anti-PC antibodies were dialyzed against a solution of 0.05M borate and 0.5M NaCl at pH 8.5. Twenty mg of dialyzed immunoaffinity-purified calcium-dependent sheep anti-human-PC IgG were then coupled to CNBr-activated Sepharose 4B as described above to form a human-PC antibody-Sepharose affinity column for purifying human PC for use in this invention. Protein C appeared as a single band with an apparent molecular weight of 62,000 daltons under non-reducing conditions. However, in the presence of a reducing agent, protein C formed two bands with mobilities representing 41,000 and 21,000 daltons. Human protein C, thus, consists of two polypeptide chains linked by a disulfide bond.

Human PC was then immunoaffinity-purified as previously described from plasma factor IX concentrate in TBS containing 5 mM $CaCl_2$ by immobilization on the calcium-dependent sheep anti-human PC-Sepharose column prepared above. The column containing immobilized PC was extensively washed with ten column volumes of a wash buffer at pH 7.4 consisting of 0.05M Tris-HCl, 1M NaCl, 5 mM $CaCl_2$, 0.02% $NaN_3$ and 0.02% Tween 20 to remove contaminating unbound proteins. Immobilized human PC was subsequently eluted with a buffer containing 0.05M Tris-HCl, 1M NaCl and 20 mM EDTA at pH 7.4. The purification of human PC from plasma factor IX concentrate was repeated several times yielding approximately 3.6 mg PC each time without significant loss of capacity of the anti-PC column. The separate elutions of purified human PC were pooled and subsequently dialyzed against five liters with four changes of TBS as described above to remove excess salts. The resultant purified human PC in its inactive or zymogen form was then used in ELISA as described below.

2) Preparation of Activated PC

The activated form of PC (APC) was prepared by treating the inactive zymogen PC prepared above with soluble alpha-thrombin-Sepharose beads. Thrombin was purchased from Enzyme Research Laboratories (South Bend, Ind.) and prepared from homogeneous human prothrombin by activation with Factor Xa, Factor Va and phospholipid. Human thrombin was homogeneous as judged by 10% SDS-PAGE. The purified thrombin was coupled to CNBr-activated Sepharose as described above. To monitor the activation of protein C, the amidolytic activity was determined in an assay using the chromogenic substrate, S-2238 (H-D-Phenylalanyl-L-pipecolyl-L-arginine-p-nitroanilide dihydrochloride, Kabi-Vitrum, Franklin, Ohio). In the assay, 60 µl of the sample was admixed to 600 µl of 0.8 mM amidolytic substrate in a buffer consisting of 0.05M Tris-HCl and 0.10M NaCl at pH 8.0. The rate of absorbance change at a wavelength of 405 nm/minute was determined. The resultant APC product was determined to be greater than 95% pure when analyzed by SDS-PAGE as described above.

3) Preparation of Antigen-Coated ELISA Plates and Detection of Immunoreactive Products To determine the immunospecificity of the rabbit antisera obtained in Example 2b, ELISA assays were performed. Briefly, depending on which sera was being screened, either PC317-331 or PC142-155 50 µl of 50 µM prepared in Example 1 was admixed into the wells of microtiter plates. Also used as ELISA substrates was 10 µg/ml of PC or APC prepared in Example 2c in a buffer consisting of 0.05M sodium carbonate ($Na_2CO_3$) and 0.02% $NaN_3$ at pH 9.0. The plates were maintained at 37° C. for one hour to permit the antigens to become operatively affixed to the well walls. After washing the antigen-coated wells with TBS, the wells were blocked with 250 µl/well of 10% bovine serum albumin (BSA) (Sigma) in TBS for one hour at 22° C. The blocking solution was then removed and the wells were subsequently washed five times with 250 µl/well of maintenance buffer (0.05M Tris-HCl, 0.1M NaCl, 0.02% $NAN_3$, 1 mg/ml BSA, 5 mM $CaC_2$, 0.01% Tween 20 at pH 7.4).

Fifty µl of rabbit non-immune or specific antiserum serially diluted in maintenance buffer was then admixed to the washed wells and maintained for one hour at 37° C. to allow formation of solid liquid phase immunoreaction products. The wells were then washed three times with maintenance buffer followed by admixture of 50 µl of 2.0 µg/ml of secondary antibody (polyclonal biotinylated goat-anti-rabbit-IgG) (Pierce Biochemicals) diluted in maintenance buffer to each well for the detection of immunoreactant products. The plates were maintained for 1 hour at 37° C. after which time the secondary antibody solution was removed. After washing the wells as described above, 50 µl of 2.0 µg/ml streptavidin-alkaline-phosphatase (Pierce Biochemicals) in maintenance buffer was admixed into each well and maintained for 30 minutes at 37° C.

Detection of specific immunoreaction products was obtained by admixture of 150 µl/well of 5 mg/ml p-nitrophenylphosphate (PNPP) (Pierce Biochemicals) in 0.1M diethanolamine and 0.02% $NaN_3$ at pH 9.6 followed by measurement of the change in absorbance at 405 nm over 20 minutes using the EL312 Microplate Bio-Kinetics Reader and the KinetiCalc Software Program (Biotek Instruments, Inc., Vt.). Non-specific binding was considered as the measured absorbance in 10% BSA blocked wells which served as negative controls without the preceding coating of a specific protein or peptide. Under the described conditions, non-specific binding never exceeded more than 5% of the specific binding. Rabbit antisera which exhibited significant immunoreactivity as compared to the pre-immune serum toward PC317-331 or PC142-155, PC and APC was selected for further purification as described in Example 3.

Rabbit antisera which are obtained in Example 2b against all the remaining peptides listed in Table 1 are screened for immunoreactivity to the respective peptide immunogens and PC or APC as described above. Rabbit antisera which exhibit significant immunoreactivity as compared to the pre-immune sera toward the peptide immunogen and PC and APC are further purified and analyzed as described in Example 3.

3. Purification of Anti-PC Antibodies, Anti-PC317-331 and Anti-PC142-155

Purification of the IgG fraction from rabbit antisera, which exhibited significant reactivity towards PC317-331 or PC142-155, was achieved by ammonium-sulfate precipitation (0–45%), followed by purification of IgG on an ion-exchange Mono Q column (Pharmacia) connected to a fast protein liquid chromatography (FPLC) system (Pharmacia). Immunoaffinity purification of the pooled immunoreactive IgG-fraction was performed by passing the IgG over a 3-ml column of protein C prepared in Example 2a (3.4 mg of immunoaffinity-purified PC/ml gel) coupled to Sepharose 4B (Pharmacia) as described in Example 2a. After thorough washing of the column with 5 column volumes of 0.05M Tris-HCl and 1M NaCl at pH 7.4 to remove unbound antibodies, the bound IgG was eluted with two column volumes of 0.1M glycine-HCl at pH 2.5. The eluted protein was monitored by absorbance at 280 nm and the IgG concentrations determined from the extinction coefficient of 13.5. The eluted IgG was immediately dialyzed against TBS-Az, concentrated against 50% sucrose and once more extensively dialyzed against TBS-Az. Analysis by 4–15% SDS-PAGE of reduced and non-reduced samples revealed greater than 95% pure IgG. The resultant immunoaffinity-purified anti-PC peptide antibodies are designated anti-PC317-331 and anti-PC142-155 for use in this invention.

a. Specificity and Affinity Analysis of Anti-PC317-331

The specificity of immunoaffinity purified anti-PC317-331 antibody towards PC317-331 and PC was evaluated by measuring the binding in solid-phase ELISA of the antibody to the immobilized peptide PC317-331, listed in Table 1, and to PC, factor IX, factor X and prothrombin. For the ELISA assay, 50 µM of PC317-331 and 10 µg/ml of each protein were admixed into separate wells of microtiter plates as described in Example 2c. After blocking the peptide- or protein-coated wells as described in Example 2c, 50 µl of 0.25 µg/ml immunoaffinity purified anti-PC317-331 antibody in maintenance buffer were admixed into PC and peptide-coated wells and 25 µg/ml antibody were admixed into the factor IX-, factor X- and prothrombin-coated wells. The plates were maintained for one hour at 37° C. to form an immunoreaction product. The detection and measurement of specific immunoreaction products was accomplished by admixture of biotinylated secondary antibody (goat anti-rabbit IgG) followed by streptavidin-alkaline-phosphatase and PNPP as described previously for the ELISA in Example 2c.

The results of the ELISA are shown in Table 4 below. The data represent the mean values of duplicate measurements. Negative controls revealed less than 5% non-specific binding. The anti-PC317-331 antibody specifically recognized immobilized peptide PC317-331 but did not bind significantly to factor IX, factor X and prothrombin. Significant immunoreactivity was observed between PC and anti-PC317-331 antibody.

TABLE 4

| Immobilized Protein Or Peptide | Anti-PC317-331 Antibody Added (μg/ml) | Anti-PC317-331 Bound Absorbance At $OD_{405}$ |
| --- | --- | --- |
| Protein C | 0.25 | 0.240 |
| PC317-331 | 0.25 | 0.422 |
| Factor IX | 25.0 | 0.026 |
| Factor X | 25.3 | 0.016 |
| Prothrombin | 25.0 | 0.016 |

The affinity of immunoaffinity purified anti-PC317-331 antibody towards APC was determined by Scatchard-analysis. Fifty μl of anti-PC317-331 antibody diluted to a concentration of 10 μg/ml in 0.05M $Na_2CO_3$ and 0.02% $NaN_3$ at pH 9.0 were admixed to wells of a microtiter plate and maintained for one hour at 37° C. to form antibody-coated wells. Following the removal of the antibody solution at the end of the maintenance period, 250 μl of 10% BSA in TBS-Az at pH 7.4 were admixed into each well for one hour at 22° C. to block unoccupied sites on the wells. For wells which were used as negative controls, the antibody coating step was omitted prior to the blocking step. The antibody-coated and blocked wells were then washed three times with maintenance buffer prepared as described in Example 2c. Fifty μl of APC prepared as described in Example 2a diluted in maintenance buffer to concentrations ranging from 0 to 5.0 μg/ml were admixed into the washed wells and maintained for one hour at 37° C. to form an immunoreaction product. The wells were subsequently washed five times with maintenance buffer. APC which bound to anti-PC317-331 antibody was detected by the admixture of 100 μl of 0.8 mM of the chromogenic substrate, S-2366, (L-pyroglutamyl-L-prolyl-L-arginine-p-nitroanilide hydrochloride; Kabi-Vitrum) diluted in TBS-Az and 0.1% BSA at pH 8.0. The APC-amidolytic activity was monitored by the change in absorbance at 405 nm using the EL312 Microplate Reader. The amount of bound APC to immobilized anti-PC317-331 antibody was calculated from a standard curve based on the amidolytic activity of known amounts of APC in fluid-phase.

The results of this assay showed that the affinity purified antibody was capable of binding native APC when the antibody was immobilized in the wells of the microtiter plate. Scatchard-analysis of the measured change in absorbance, using known amounts of APC in fluid-phase as standards, revealed at least two populations of antibodies with apparent dissociation constants ($K_d$) of 0.8 and 9 nanomolar (nM). The plotted data represent the mean values of duplicate measurements.

Polyclonal antibodies raised against the peptide, PC317-331, were immunoaffinity purified on a PC-Sepharose column suggesting that at least parts of the region represented by this peptide in PC are exposed and available for interaction with antibodies at the solvent accessible surface of PC. The immunoaffinity purified anti-PC317-331 antibody recognized the corresponding peptide and PC as well as APC. Scatchard analysis revealed at least two different populations of antibodies with apparent dissociation constants ($K_d$) of 0.8 nM and 9 nM, respectively. Anti-PC317-331 antibody appears to be at least 1000 fold more specific for PC compared to Factor IX, X and prothrombin although the sequence of residues 317-331 in PC shows some degree of homology to these proteins (Table 1).

b. Specificity and Affinity Analysis of Anti-142-155

The specificity of anti-PC142-155 antibody, prepared in Example 2 and in Example 3, towards synthetic peptides, APC or PC was evaluated by measuring the binding of the antibody to immobilized peptides and the proteins, PC, APC, factor IX, factor X and prothrombin in ELISA assays as described in Example 2c.

Studies were made to investigate whether the anti-PC142-155 antibody was specific for PC and APC compared to other vitamin K dependent serine proteases. The binding of anti-PC142-155 antibody to immobilized PC, factor IX, factor X and prothrombin was measured using solid phase ELISA technology, as described in Examples 2c and 3a. Anti-PC142-155 antibody was separately admixed in microtiter plate wells coated with PC142-155, PC, factor IX, factor X and prothrombin. The amount of antibody detected bound to the wells containing PC or PC142-155 was at least 26-fold higher than to the wells coated with factor IX, factor X or prothrombin (Table 5) even though the latter wells contained 100-fold higher antibody concentrations. Positive controls for the wells with immobilized factor IX, X or prothrombin with the appropriate respective specific antisera confirmed that these proteins were bound to the plate. This shows that anti-PC142-155 was at least 2000-fold more specific for PC compared to the other vitamin K dependent factors tested.

TABLE 5

| Immobilized Protein or Peptide | Anti-(142-155) Antibody Added (μg/ml) | Anti-(142-155) Bound Absorbance $OD_{405}$ |
| --- | --- | --- |
| Protein C | 0.5 | 0.341 |
| PC142-155 | 0.5 | 0.426 |
| Factor IX | 50.0 | 0.007 |
| Factor X | 50.0 | 0.013 |
| Prothrombin | 50.0 | 0.009 |

The immunoaffinity purified polyclonal anti-peptide antibody, anti-PC142-155, was also shown to bind to immobilized PC and APC in a saturable manner with the same apparent affinity for immobilized PC or APC in assays performed as described in Example 2c. Moreover, the antibody was capable of binding native APC ranging from 0 to 1 μg/ml in concentration, when the antibody was immobilized in the wells of microtiter plates, in assays performed as described in Example 3a above. Binding of anti-PC142-155 was maximal and saturated at an APC concentration of 1 μg/ml.

Thus, polyclonal antibodies raised against the PC142-155 that were immunoaffinity purified on a PC-Sepharose column show that at least parts of the region represented by this peptide in PC are exposed and available for interaction with antibodies at the solvent accessible surface of PC. The immunoaffinity purified anti-PC142-155 antibody recognizes the corresponding peptide and PC as well as APC and appears to be at least 2000-fold more specific for PC compared to factor IX, X and prothrombin as shown in Table 5).

4. Preparation of Monoclonal Antibodies a. Anti-peptide

The polypeptide designated PC317-331 is prepared as an immunogen according to Example 2a. Balb/c ByJ mice (Scripps Clinic and Research Foundation Vivarium, La Jolla, Calif.) are immunized intraperitoneally (i.p.) with 50 μg of prepared PC317-331-KLH immunogen in complete Freund's adjuvant (CFA) followed by a second and third immunization using the same PC317-331-KLH immunogen, each about three weeks apart, in incomplete Freund's adjuvant (IFA). The mice receive a boost of 50 μg of the prepared peptide intravenously (i.v.) in normal saline 4 days prior to fusion and a second similar perfusion boost one day later.

The animals so treated are sacrificed and the spleen of each mouse was harvested. A spleen cell suspension is then prepared. Spleen cells are then extracted from the spleen cell suspension by centrifugation for about 10 minutes at 1000 r.p.m., at 23° C. Following removal of the resultant supernatant, the cell pellet is resuspended in 5 ml cold ammonium chloride ($NH_4Cl$) lysing buffer, and is maintained for about 10 minutes.

Ten ml of Dulbecco's Modified Eagle Medium (DMEM) (GIBCO) and HEPES [4-(2-hydroxyethyl)-1-piperidineethanesulfonic acid] buffer are admixed to the lysed cell suspension to form an admixture, and that admixture is centrifuged for about 10 minutes at 1000 r.p.m. at 23° C.

After the resultant supernatant is decanted, the pellet is resuspended in 15 ml of DMEM and HEPES and is centrifuged for about 10 minutes at 1000 r.p.m. at 23° C. The above procedure is repeated.

The pellet is then resuspended in 5 ml DMEM and HEPES. An aliquot of the spleen cell suspension is then removed for counting. Fusions are accomplished in the following manner using the non-secreting mouse myeloma cell line P3X63Ag 8.653.1, a subclone of line P3x63Ag 8.653 (ATCC 1580). With a myeloma to spleen cell ratio of about 1 to 10 or about 1 to 5, a sufficient quantity of myeloma cells are centrifuged into a pellet, washed twice in 15 ml DMEM and HEPES, and then centrifuged for 10 minutes at 1000 r.p.m. at 23° C.

Spleen cells and myeloma cells are combined in round bottom 15 ml tubes. The cell mixture is centrifuged for 10 minutes at 1000 r.p.m. at 23° C. and the supernatant is removed by aspiration. Thereafter, 200 μl of 50 percent (weight per volume) aqueous polyethylene glycol 4000 molecular weight (PEG); (ATCC Baltimore, Md.) at about 37° C. are admixed with the pellet using a 1 ml pipette with vigorous stirring to disrupt the pellet. The cells are then gently mixed for between 15 and 30 seconds. The resultant cell mixture is centrifuged 4 minutes at 700 r.p.m.

At about 8 minutes after the time of adding the PEG, 5 ml of DMEM plus HEPES buffer are admixed slowly to the pellet, without disturbing the cells. After 1 minute, the resulting admixture is broken up with a 1 ml pipette and is maintained for an additional 4 minutes. This admixture is centrifuged for 7 minutes at 1000 r.p.m. The resultant supernatant is decanted, 5 ml of HT (hypoxanthine/thymidine) medium are slowly admixed to the pellet, and the admixture is maintained undisturbed for 5 minutes. The pellet is then broken into large chunks and the final cell suspension is placed into T75 flasks (2.5 ml per flask) into which 7.5 ml HT medium have been placed previously. The resulting cell suspension is maintained at 37° C. to grow the fused cells. Forty-eight hours after fusion, 10 ml of HAT (hypoxanthine/aminopterin/thymidine) medium are admixed to the flasks.

Three days after fusion, viable cells are plated out in 96-well tissue culture plates at about $2 \times 10^4$ viable cells per well (768 total wells) in HAT buffer medium as described in Kennett et al., Curr. Top. Microbiol. Immunol., 81:77 (1978). The cells are fed seven days after fusion with HAT medium and at approximately 4–5 day intervals thereafter as needed with HT medium. Growth is followed microscopically and culture supernatants are collected about two weeks later. The culture supernatants are subsequently assayed for the presence of PC317-331 specific antibody by solid-phase ELISA as described in Example 2c or by solid-phase radioimmunoassay (RIA) described below.

For screening by RIA, 50 μl of PBS containing 5 μg/ml of the prepared PC317-331-KLH immunogen is admixed into the wells of microtiter plates. The plates are maintained overnight (about 16 hours) at 4° C. to permit the PC317-331-KLH immunogen to adhere to well walls. After washing the wells four times with SPRIA buffer (2.68 mM potassium chloride (KCl), 1.47 mM potassium phosphate ($KH_2PO_4$), 137 mM NaCl, 8.03 mM sodium phosphate ($Na_2HPO_4$), 0.05% Tween-20, 0.1 KIU/ml Traysol, 0.1% BSA, 0.015% $NAN_3$), 200 μl of SPRIA buffer containing 3% normal goat serum and 3% BSA are admixed to each well to block excess protein binding sites. The plates are maintained for 30 minutes at 20° C., the wells emptied by shaking, and subsequently blotted dry to form a solid-support, i.e., a solid matrix to which PC317-331-KLH immunogen is operatively affixed.

To each well is then admixed 50 μl of hybridoma tissue culture supernatant to form a solid-liquid phase immunoreaction admixture. The admixture is maintained for 2 hours at 37° C. to permit formation of solid-phase immunoreaction products. After washing the wells as previously described, 50 μl of $^{125}$I-labeled goat anti-mouse IgG at 0.25 μg protein per ml are admixed to each well to form a labeling reaction admixture. That admixture is maintained for 1 hour at 37° C. to permit formation of $^{125}$I-labeled solid-phase immunoreaction products. After washing the wells as previously described, the amount of $^{125}$I-labeled product bound to each well is determined by gamma detection.

Hybridomas are selected from hybridoma cultures that secrete anti-PC317-331 antibodies into their culture media, and further characterized as described herein.

Monoclonal antibodies are also raised against the remaining peptide immunogen listed in Table 3 coupled to KLH as described above for PC317-331. The produced monoclonal antibodies are purified as described below.

b. Purification of Monoclonal Antibody

Ascites fluids are obtained from separate sets of 10-week old Balb/c mice, which are primed with 0.3 ml of mineral oil and injected intraperitoneally with $5 \times 10^6$ hybridoma cells prepared above. The average time for development of ascites is 9 days. Following clarification by centrifugation at 15,000×g for 15 minutes at 23° C., ascites fluids produced by hybridomas are pooled and stored frozen at −20° C.

Purified monoclonal antibodies directed against PC317-331-KLH from the hybridomas are prepared by fast protein liquid chromatography (FPLC) using a Pharmacia Mono Q HR5/5 anion exchange column (Pharmacia) using a 0–0.5M NaCl gradient in 10 mM Tris-HCl at pH 8.0 following directions supplied with the column. Purified Mabs were concentrated using an Amicon stirred ultrafiltration cell (Danvets, Mass.; PM 30 membrane) to a concentration of 1 mg/ml, dialyzed into PBS (phosphate-buffered saline at pH 7.2) and stored at −70° C.

Hybridomas secreting anti-PC317-331 antibodies as described in Example 4A are injected into 10-week old Balb/c mice as described above to obtain ascites fluid. Purified anti-PC317-331 monoclonal antibodies are prepared by FPLC and are concentrated in an Amicon stirred ultrafiltration cell and stored as described.

5. Inhibition of APC a. Inhibition of APC by Synthetic Peptides Derived from PC

The overlapping PC peptides derived from both the heavy and light chains of the zymogen PC listed in Table 3 were screened for their ability to inhibit APC anticoagulant activity in five different assays as described below. The peptides evaluated in the assays are listed in Table 3 according to the corresponding region in the PC heavy chain and by their SEQ ID NO. Hereinafter, the peptides will be referred to by the corresponding region in PC, e.g., PC311-325 or PC142-155. The assays were used to determine the region in APC essential for the protein's anticoagulant activity and for the recognition of the macromolecular substrates, activated Factors V (Va) and VIII (VIIIa).

1) Activated Partial Thromboplastin Time (APTT) Coagulation Assay

The effect of the synthetic peptides on APC anticoagulant activity were determined using the APTT assay in the presence of either normal citrate anticoagulated plasma (NHP) or protein S depleted plasma (PSDP). The assays were performed essentially as described. See Marlar et al., *Blood*, 59:1067–1072 (1082); Suzuki et al., *J. Biol. Chem.*, 258:163–168 (1983); Gruber et al., *Blood*, 73:639–642 (1989); Ohlin et al., *Biochem.*, 29:644–651 (1990). NHP was purchased from George King Bio-Medical, Inc. (Overland Park, Ka.). PSDP was prepared from a normal human citrate-anticoagulated plasma pool from ten healthy donors. Protein S was immunodepleted from the NHP by immunoaffinity chromatography of NHP over an anti-protein S antibody column to form PSDP. The anti-protein S antibody column was prepared by coupling 100 mg of a monoclonal, high-affinity, calcium-independent anti-PS antibody, designated S7, to 30 ml of CNBr-activated Sepharose 4B (Pharmacia) as described in Example 2c1). Residual total protein S content in the resultant PSDP was less than 0.1% protein S as determined by quantitative immunoblotting, by solid-phase ELISA for total protein S and by electroimmunoassay.

For the APTT assay, APC was prepared as described in Example 2c2). The specific anticoagulant activity of APC was determined to be 250 Units/mg. The concentration of the APC used in the assay was initially optimized with respect to the sensitivity of the assay towards APC-induced prolongation of clotting time compared to clotting time without APC.

Once the optimal concentration of APC was determined, peptides from the heavy and light chains of PC and control scrambled peptides listed below in Example 5a2) in Tables 6 and 7 were then separately admixed for a final concentration of 500 μM with 10 nM APC in 100 μl of TBS-BSA at pH 7.4 to form peptide-APC admixtures. Peptides were prepared as described in Example 1. The resulting admixtures were maintained for ten minutes at 37° C. Separate aliquots of peptides maintained under the same conditions in the absence of APC served as controls for the inhibitory effect of synthetic peptides on APC anticoagulant activity.

After the maintenance period, 100 μl of NHP and 100 μl APTT-reagent Thrombosil (Ortho Diagnostics, Raritan, N.J.) were admixed into each peptide admixture and maintained for 200 seconds at 37° C. to form a pre-coagulation admixture. In some experiments, PSDP was used in the place of NHP to determine the effect of Protein S on the assay system. Coagulation was then initiated by the admixture of 100 μl of 30 mM CaCl$_2$ in TBS prewarmed to 37° C. to each of the pre-coagulation admixtures. The time for clot formation was measured by an Electra 700 Automatic Coagulation Timer (Medical Laboratory Automation, Inc., Mount Vernon, N.Y.). Each peptide's effect was determined in duplicate.

The results of these experiments are shown below in Example 5a2) with the results of the Xa-1 stage coagulation assay. The results of assays with heavy chain and light chain peptides are respectively shown in Tables 6 and 7. APC anticoagulant activity standard curves were generated for each experimental series wherein a straight line resulted when APC-induced prolongation of clotting time was plotted against APC-concentration on a double-logarithmic plot. The standard curves were constant with a deviation of 6% over the course of the experiment. The mean values from the APTT assay and the Xa-1 stage assay described in Example 5a2) are presented therein with peptides used at their respective final concentrations. For peptides at a concentration of 500 μM that inhibited at least 50% of APC anticoagulant activity, analysis of dose-response was subsequently conducted.

2) Xa-1-Stage Coagulation Assay

For testing the inhibition of the synthetic peptides on APC activity described above, Xa-1-stage coagulation assays were also performed as described. See Seegers et al., *Thrombosis Res.*, 13:233–243 (1978); Marlar et al., supra; and Walker et al., *J. Biol. Chem.*, 265:1484–1489 (1990). PC heavy chain-derived peptides listed below in Table 6 and PC light chain-derived peptides listed below in Table 7. were prepared as described above and separately admixed for a final concentration of 2 mM with 120 nM APC in 100 μl of TBS-BSA at pH 7.4 to form separate peptide-APC admixtures. The resulting admixtures were maintained for ten minutes at 37° C. Separate aliquots of peptides maintained under the same conditions in the absence of APC served as controls for the inhibitory effect of synthetic peptides on APC anticoagulant activity. After the maintenance period, 100 μl of NHP and 100 μl of 200 μg/ml of rabbit brain cephalin (Sigma) were admixed into each peptide admixture and maintained for 200 seconds at 37° C. to form precoagulation admixtures. In some experiments, Factor VIII deficient plasma (George King Bio-Medical, Inc.) was used in the place of NHP to determine the effect of Factor VIII on the assay system. Coagulation was then initiated by the admixture of 100 μl of 0.62 nM human activated Factor X (Xa) (Enzyme Research Laboratories, Southbend, Ind.) in TBS-BSA containing 30 mM CaCl$_2$ prewarmed to 37° C. to each of the pre-coagulation admixtures.

The time for clot formation was measured by an Electra 700 Automatic Coagulation Timer (Medical Laboratory Automation, Inc., Mount Vernon, N.Y.). Each peptide's effect was determined in duplicate. The results of the inhibition of APC anticoagulant activity by synthetic peptides as measured in Xa-1-stage coagulation assays are presented in Tables 6 and 7 below with the APTT assay results and are presented as the mean values obtained with APTT assays. Data for results with PC heavy chain-derived peptides are shown in Table 6 and data for results with PC light chain-derived peptides are shown in Table 7.

(a) Inhibition of APC Anticoagulant Activity by PC Heavy Chain-derived Peptides

The results of inhibition of APC anticoagulant activity by PC heavy chain-derived peptides in APTT and Xa-1 stage coagulation assays are shown in Table 6. The assays were performed in the presence of NHP. The mean values for both assays are given for peptides, PC311-325 and PC317-331. The peptide (SEQ ID NO 8) having a scrambled sequence of the amino acid residues in PC311-325 was used a control.

TABLE 6

| Peptide | SEQ ID NO | $IC_{30}$* µM | $IC_{90}$** µM |
|---|---|---|---|
| PC311-325 | 1 | 13 | 50 |
| PC317-331 | 1 | 500 | 500 |
| Control Peptide (at 500 µM) | 8 | no effect (± 10%) | no effect (± 10%) |

*$IC_{30}$ is defined as the concentration of peptide that inhibits 50% of APC anticoagulant activity;
**$IC_{90}$ is defined as the concentration of peptide that inhibits 90% of APC anticoagulant activity.

Since the synthetic PC317-331 inhibited APC anticoagulant activity in APTT and Xa-1-stage coagulation assays with 50% inhibition at 500 µM peptide as shown in Table 6, the PC311-325 heavy chain-derived peptide was synthesized to determine whether it was an effective APC anticoagulant. PC311-325 peptide inhibited APC anticoagulant activity in APTT and Xa-1-stage assays in NHP and PSDP with 50% inhibition at 7 to 20 µM and 90% inhibition at approximately 50 µM. The control peptide with a randomized sequence of the 311-325 residues had no significant effect on APC anticoagulant activity when tested at various concentrations up to 500 µM peptide.

The assays were also performed using PSDP instead of NHP where the effect of the presence of protein S could be evaluated. Since the observed dose response of PC311-325 was identical in APTT assays in either NHP or PSDP, the inhibitory effect of PC311-325, thus, is not dependent on the presence of protein S. Therefore, the interaction between APC and protein S is not disturbed by PC311-325.

(b) Inhibition of APC Anticoagulant Activity by PC Light Chain-derived Peptides

The results of inhibition of APC anticoagulant activity by PC light chain-derived peptides in a Xa-1 stage coagulation assay are shown in Table 7. The assay was performed in the presence of NHP. Peptides used in the assay were prepared as described in Example 1 and are listed in Table 7 by their corresponding residue positions in native PC protein (SEQ ID NO 1). For all peptides except PC142-155 used in the Xa-1 stage assays listed in Table 7, cysteine residues in the native PC amino acid residue sequence were substituted by either serine or glycine in the synthesized peptide. This was done to prevent multiple disulfide formation and subsequent potential polymerization among peptides with multiple cysteines. The peptides were used at a final concentration of 500 µM. The data is presented as percent inhibition of APC anticoagulant activity calculated from an APC standard curve at a final peptide concentration of 500 µM.

TABLE 7

| Peptide | Inhibition of APC (%) |
|---|---|
| PC36-50 | 0 |
| PC43-57 | 0 |
| PC48-62 | 0 |
| PC65-79 | 0 |

TABLE 7-continued

| Peptide | Inhibition of APC (%) |
|---|---|
| PC81-95 | 40 |
| PC110-124 | 0 |
| PC121-135 | 0 |
| PC125-139 | 30 |
| PC134-148 | 66 |
| PC142-155 | 80 |

0 is defined as no observable effect + 10%

The effect of ten synthetic PC peptides (15-mers) derived from the light chain of PC screened for their ability to inhibit APC anticoagulant activity in Xa-1-stage coagulation assays in NHP at a final peptide concentration of 500 µM are shown above in Table 7. Six of ten peptides had no effect on APC anticoagulant activity at all (Table 7). For the most potent peptide from the initial screening, PC142-155 a dose-response study was made. PC142-155 inhibited APC anticoagulant activity in a Xa-1-stage coagulation assay in protein S-depleted plasma with 50% inhibition at 5 µM peptide. A similar dose-response of PC142-155 on APC anticoagulant activity was obtained in Xa-1-stage coagulation assay in NHP with 50% inhibition at 25 µM. PC134-148 that shares parts of its sequence with PC142-155 inhibited 50% of APC anticoagulant activity in a Xa-1-stage assay in NHP at 250 µM peptide. The scrambled peptide with a randomized sequence of the 142-155 residues showed very little if any significant inhibition of APC anticoagulant activity.

Thus, the inhibitory effect of PC142-155 is specific since the scrambled peptide with a randomized sequence of residues 142-155 only slightly affected APC anticoagulant activity and six of ten peptides from the initial screening had no effect at all. PC142-155 inhibited APC anticoagulant activity in NHP as well as PSDP suggesting that the inhibitory effect of this peptide is not dependent on the presence of protein S.

3) Amidolytic Activity of APC Assay

The effects of PC-derived inhibitory synthetic peptides on the amidolytic activity of APC were evaluated to determine if the peptides inhibited APC anticoagulant activity by blocking a region in or close to the active site of the enzyme involved in cleavage of a small substrate such as S-2366 (Kabi-Vitrum) or involved in the site of interaction with the recombinant mutant $(Arg^{358})\alpha_1$-antitrypsin ($\alpha_1$-AT) (Transgene, Strasbourg, France), the latter of which is described in Example 5a4) below. The assay was performed as described by Marlar et al., supra; and Suzuki et al., supra.

The amidolytic activity of APC toward the peptide substrate S-2366 was measured in the presence of various PC synthetic peptides derived from both the heavy and light chain, prepared in Example 1. For the assay, 100 µl of 10 nM APC, prepared in Example 2c2), were admixed with separate aliquots of 250 µM of PC311-325 and 500 µM Df PC142-155 prepared in TBS-BSA at pH 7.4 containing 0.02% $NaN_3$ and 2 mM $CaCl_2$ to form APC-peptide admixtures. After maintenance of the admixtures for 30 minutes at 37° C., 50 µl of 2.4 mM S-2366 in the same buffer were admixed to initiate the amidolytic reaction. The hydrolysis of the substrate was monitored by the change in absorbance at 405 nm at 37° C. over time using an EL312 Microplate Bio-Kinetics Reader (BIO-TEK Instruments, Inc. Vt.). All data are mean values of duplicate measurements.

In contrast to the inhibitory effects of synthetic peptides on APC anticoagulant activity, peptides, PC311-325 from the heavy chain and PC142-155 from the light chain, did not significantly alter APC amidolytic activity towards the chromogenic substrate, S-2366 as shown in Table 8 below. These results indicate that these peptides do not exert inhibitory effects of APC anticoagulant activity by blocking a region in or close to the active site of the enzyme involved in cleavage of a small substrate.

TABLE 8

APC Amidolytic Activity in the Presence of Peptides, PC, 311–325 and PC142–155 Towards S-2366

| Reagent Admixed | Change in $A_{405}$/5 minutes |
|---|---|
| None | 0.374 |
| PC311–325 | 0.342 |
| PC142–155 | 0.344 |
| Scrambled peptide (SEQ ID NO 9) | 0.364 |

Thus, in contrast to these observations of APC inhibition in the coagulation assays up to 250 μM of PC311-325 or 500 μM of PC142-155 maintained with APC for 30 min at 37° C. prior to the addition of the chromogenic substrate, had no significant effect on APC amidolytic activity towards the chromogenic substrate S-2366.

These data indicate that neither PC311-325 nor PC142-155 affected the reactivity of the active site residues and did not exert their inhibition of APC anticoagulant activity by blocking primary substrate binding sites close to the active site serine that are involved in cleavage of a small tripeptide substrate like S-2366 or in recognition of the recombinant 55,000 Mr $\alpha_1$-AT as will be shown below in Example 5a4).

4) Inhibition of APC by Recombinant Mutant $\alpha_1$-Antitrypsin Assay

Since the number of amino acid residues involved in the neutralization of APC by macromolecular plasma protease inhibitors is likely to be higher than the number of residues of APC involved in the cleavage of a small chromogenic substrate such as S-2366, the effect of PC311-325 and PC142-155 on the time course of inhibition of APC by a larger pseudo-substrate, recombinant mutant $(Arg^{358})$-$\alpha_1$-antitrypsin ($\alpha_1$-AT) was evaluated. The substitution of $Met^{358}$ by Arg in the reactive center of recombinant $\alpha_1$-AT has been shown to result in an increase of over 4400-fold in the association rate for APC. Heeb et al., *J. Biol. Chem.* 265:2365–2369 (1990).

Kinetic studies of inhibition of APC were performed with the higher affinity mutant $\alpha_1$-AT pseudo-substrate. For the assay, 60 μl of 36 nM APC and/or 60 μl of 200 nM recombinant $(Arg^{358})$-$\alpha_1$-AT prepared in TBS-BSA at pH 7.4 containing 0.02% NaN$_3$ and 2 mM CaCl$_2$ were separately admixed with 500 μM PC311-325 or 1 mM PC142-155 and maintained for 30 minutes at 37° C. to form APC-peptide and/or $\alpha_1$-AT-peptide admixtures for each peptide tested, respectively. Thereafter, the peptide-treated APC and $\alpha_1$-AT admixtures were combined to form a reaction admixture. At selected time points, 8 μl aliquots from the reaction admixture were removed and admixed with 300 μl 10.8 mM S-2366 in TBS-BSA at pH 8.0 containing 0.02% NaN$_3$ to initiate the hydrolysis of S-2366 by APC. The change in absorbance was measured over time as described in the amidolytic assay. Controls without the inhibitor $\alpha_1$-AT in the absence or presence of peptides were included in the assay.

APC activity in the controls performed above was constant with a deviation of 5% over the course of the experiment. PC311-325, in addition to PC142-155, at final concentrations of 250 μM and 500 μM, respectively, did not have any significant effect on the time course of inhibition of APC at a final concentration of 18 nM by recombinant $(Arg^{358})\alpha_1$-AT. In addition, APC activity in the presence of either peptide but in the absence of $\alpha_1$-AT was not inhibited over the assayed time course of 10 minutes. The calculated half-life of 2 minutes for APC under the assay conditions with final concentrations of 18 nM APC and 100 nM $\alpha_1$-AT agreed with the recently reported half-life of APC. Heeb et al., supra. These results, which are consistent with the amidolytic assay results described above, provide additional support that both of the APC inhibitory peptides, PC311-325 of the heavy chain and PC142-155 of the light chain, do not act by blocking a region in or close to the active site of the enzyme or other important sites involved in interactions with the recombinant mutant $\alpha_1$-AT.

5) Inactivation Assay of Factor Va by APC

Since the peptides, PC311-325 and PC142-155 were shown to be potent inhibitors of APC anticoagulant activity in coagulation assays described in Examples 5a1) and 5a2), the peptides were also evaluated for their ability to inhibit the APC-catalyzed inactivation of Factor Va in the presence of phospholipid vesicles in a purified system using APC. The assay consisted of two parts wherein the APC catalyzed inactivation of Factor Va in the absence or presence of the separate peptides was tested in the first part followed by the indirect determination of remaining Factor Va activity in a prothrombinase assay in the second part.

Inactivation of Factor Va by APC:

The APC catalyzed inactivation of Factor Va assays were performed in 96-well flat bottom ELISA plates (Stockwell Scientific, Walnut, Calif.). The reactions were performed either in the presence or absence of phospholipid vesicles to determine if either PC311-325 or PC142-155 inhibited APC anticoagulant activity by inhibiting the binding of APC or its substrate to phospholipids or if it was independent of phospholipid surfaces. This determination was relevant in light of reports that the assembly of APC with its substrates Va and VIIIa on the phospholipid surface appeared to be mediated mainly by the Gla-domain of APC in the presence of calcium which was crucial for exerting significant anticoagulant activity. [Sugo et al., *J. Biol. Chem.*, 260:10453–10457 (1985); Krishnaswamy et al., *J. Biol. Chem.*, 261:9684–9693 (1986); Solymoss et al., *J. Biol. Chem.*, 263:14884–14890 (1988)].

For the preparation of phospholipid residues for use in the assay bovine brain phosphatidylserine in chloroform (CCl$_4$) /methanol (CH$_3$OH) and soybean phosphatidylcholine (Type III-S, CCl$_4$ solution) were purchased from Sigma and were reported to be at least 98% homogeneous (supplier's estimates). To prepare vesicles, phosphatidylserine was admixed with phosphatidylcholine (20% phosphatidylserine/80% phosphatidylcholine; M/M) and the organic solvent evaporated under a stream of nitrogen. The resultant phospholipid admixture was resuspended in 0.05M TBS-Az at pH 7.4 as a 1.25 mM solution by vortexing. Single bilayer vesicles were obtained during sonication by direct probe (Heat-Systems-Ultrasonics, Inc., W-220F Sonicator) for 6×30 second bursts at 30 W in 2 minute intervals at 4° C.

The reaction buffer consisted of 0.05M Tris-HCl, at pH 7.4 containing 0.1M NaCl, 0.02% NAN$_3$, 0.5% BSA and 2.5 mM CaCl$_2$. Reactions were performed in reaction buffer in the absence or presence of 50 μM phospholipid vesicles (20% phosphatidylserine/80% phosphatidylcholine; M/M)

either at 22° C. (in the presence of phospholipids) or at 37° C. (in the absence of phospholipids). In the presence of phospholipids, the final APC concentration was ≦0.25 nM with 10.0 nM Va and in the absence of phospholipids the final APC concentration was 5.0 nM APC with 40.0 nM Va. Before admixing APC to the solution containing Factor Va, a 5 μl aliquot was removed and admixed to 95 μl of 1.5 μg/ml (at APC up to 0.25 nM) or 20 μg/ml (at 5.0 nM APC) immunoaffinity-purified monoclonal antibody C3 in TBS-BSA. The monoclonal antibody C3 which specifically recognizes the light-chain of PC as well as APC was prepared as in Example 2. Factor Va (a gift from Drs. Tans and Rosing, Univ. of Limburg, the Netherlands) was first admixed with or without PC311-325 or PC142-155 and maintained for 20 minutes either at 22° C. or at 37° C. prior to admixture with APC. After admixture of an equal volume of APC with the pretreated-Va-containing solution, 10 μl aliquots were removed at appropriate short time intervals (30 seconds up to 2.5 minutes) and the reaction was then quenched by the addition to 90 μl of immunoaffinity-purified C3 antibody. Controls confirmed that the APC inactivation of Va was completely quenched by this procedure, that Factor Va remained stable over the course of the experiment and that neither the C3 antibody nor the peptides PC311-325 or PC142-155, had any effect on the subsequent measurement of residual Factor Va activity in the prothrombinase by itself.

After sample collection, an aliquot of this solution was assayed for Va activity as described below. Since in the presence of phospholipids the APC-catalyzed inactivation obeys second order kinetics, the first-order rate-constants ($k_1$-values) were calculated from the slopes of the plots of the logarithm of residual Va activity over time before 40% of Va was consumed. These initial slopes were found to be linear. In the range from 0.0 up to 0.25 nM APC with 10.0 nM Va, the observed $k_1$-value was linearly dependent on the APC concentration. The measured APC activity in percent, in the presence of PC311-325 or PC142-155, was determined by referring the observed $k_1$-values to the APC standard curve of $k_1$-values at known APC concentrations. The inactivation of Factor Va by APC in the absence of phospholipids was linear over time until 40-50% of Factor Va had been consumed.

Factor Va-Prothrombinase Assay:

Factor Va was determined via its cofactor activity in the activation of prothrombin by Factor Xa. Amounts of Factor Xa (Enzyme Research Lab.), phospholipid vesicles and prothrombin (purified as described by Stenflo, *J. Biol. Chem.*, 25:355-363, (1976) from a barium citrate plasma precipitate purified by DEAE-sephadex chromatography) present in the assay were such that the rate of prothrombin activation was linearly dependent on factor Va and constant over the time course of the experiment. The molar concentration of Factor Xa was determined by active site titration as described by Chase et al., *Biochem. Biophys. Res. Commun.*, 29:508-514 (1967). The molecular weights and extinction coefficients ($E_{280}$ nm/mg/ml) used in the calculation of protein concentrations were as follows: prothrombin, 72,000 and 1.44; APC, 62,000 and 1.45; and Factor X, 65,300 and 1.16.

In a typical experiment, Factor Va was assayed as follows. An aliquot of the solution containing Va was admixed to a solution containing prothrombin, phospholipids and calcium in individual wells of a 96-well microtiter plate. Prothrombin activation was initiated with the mixture of Factor Xa to the Va-containing wells to form a reaction admixture. Final concentrations of reagents in the reaction mixture were the following: 1.2 μM prothrombin, 1 nM Xa, 0-0.4 nM Va, 50 μM phospholipid-vesicles (phosphatidylserine 20%/phosphatidylcholine 80%; M/M), in 0.05M Tris-HCl at pH 7.4 containing 0.1M NaCl, 0.5% BSA and 2.0 mM $CaCl_2$. The reaction was maintained at 22° C. At one minute time intervals from initiation of the reaction, 20 μl aliquots of the reaction admixture were withdrawn and admixed to wells of an ELISA plate containing 80 μl TBS-BSA and 10 mM EDTA at pH 8.0 resulting in the quenching of the prothrombinase reaction. After sample collection, 50 μl of 2.0 mM S-2238 in TBS-BSA and 10 mM EDTA at pH 8.0 was admixed to the quenched reaction admixture and the amidolytic activity of the generated thrombin towards the chromogenic substrate S-2238 was then monitored by measuring the absorbance at 405 nm over time using EL312 Kinetics Reader and the Kineticalc Software Program (Biotek). The amount of thrombin formed over time was linearly dependent on Factor Va (up to 0.4 nM Va). From a standard curve with known amounts of Factor Va the amount of Factor Va present in the reaction mixture was calculated.

For the heavy chain-derived PC peptide, PC311-325, a dose-dependent inhibition of the APC-catalyzed inactivation of Factor Va with half-maximal inhibition at 6 μM was observed. Moreover, PC311-325 inhibited the APC-catalyzed inactivation of Factor Va in the absence of phospholipids. Using 5 nM APC and 40 nM Va, the rate of Factor Va inactivation (% $V_r$/min) was measured to be 4.0% $V_r$/min in the absence of peptide and 0.5% $V_r$/min in the presence of 50 μM PC311-325 corresponding to 87% inhibition of APC activity in this assay.

Thus, the observation that PC311-325 inhibited APC-catalyzed inactivation of purified Factor Va in the presence as well as in the absence of phospholipids with a similar dose response as in the coagulation system excludes the possibility that PC311-325 inhibits binding of APC or its substrate Factor Va to phospholipids.

For the light chain-derived PC peptide, PC142-155, a dose-dependent inhibition of the APC-catalyzed inactivation of Factor Va with half-maximal inhibition at 50 μM was observed. Moreover, PC142-155 inhibited the APC-catalyzed inactivation of Factor Va in the absence of phospholipids. Using 5 nM APC and 40 nM Va, the rate of Factor Va inactivation (% $V_r$/min) was measured to be −4.1% $V_r$/min in the absence of peptide and −0.5% $V_r$/min in the presence of 500 μM PC142-155 corresponding to 87% inhibition of APC activity in this assay.

Thus, the observation that PC142-155, as with PC311-325, inhibited APC-catalyzed inactivation of purified Factor Va in the presence as well as in the absence of phospholipids with a similar dose response as in the coagulation system excludes the possibility that PC142-155 inhibits binding of APC or its substrate Factor Va to phospholipids.

These results indicate that residues 311-325 and residues 142-155 represent exosites on APC essential for its anticoagulant activity and for the recognition of its macromolecular substrate Factor Va, and possibly Factor VIIIa. The proposed exosite is not involved in substrate recognition immediately near the active site or in APC interactions with protein S.

6) Factor Xa Amidolytic Activity Assay

To determine the effect of the APC-inhibiting peptides, PC311-325 and PC142-155, on the amidolytic activity of Factor Xa, amidolytic assays as described for APC in Example 5a3 were performed using 0.15 nM Factor Xa in the presence of increasing amounts of peptide. Peptide PC311-325 ranged in concentration from 0 to 100 μM whereas peptide PC142-155 ranged in concentration from 0 to 50 μM.

For the assay, 100 µl of 0.15 nM factor Xa, prepared in Example 5a5) were admixed with separate aliquots of either peptide prepared in TBS-BSA at pH 7.4 containing 0.02% NaN$_3$ and 2 mM CaCl$_2$ to form APC-peptide admixtures. After maintenance of the admixtures for 30 minutes at 37° C., 50 µl of 2.4 mM S-2222 in the same buffer were admixed to initiate the amidolytic reaction. The hydrolysis of the substrate was measured as described before.

Figure 2:
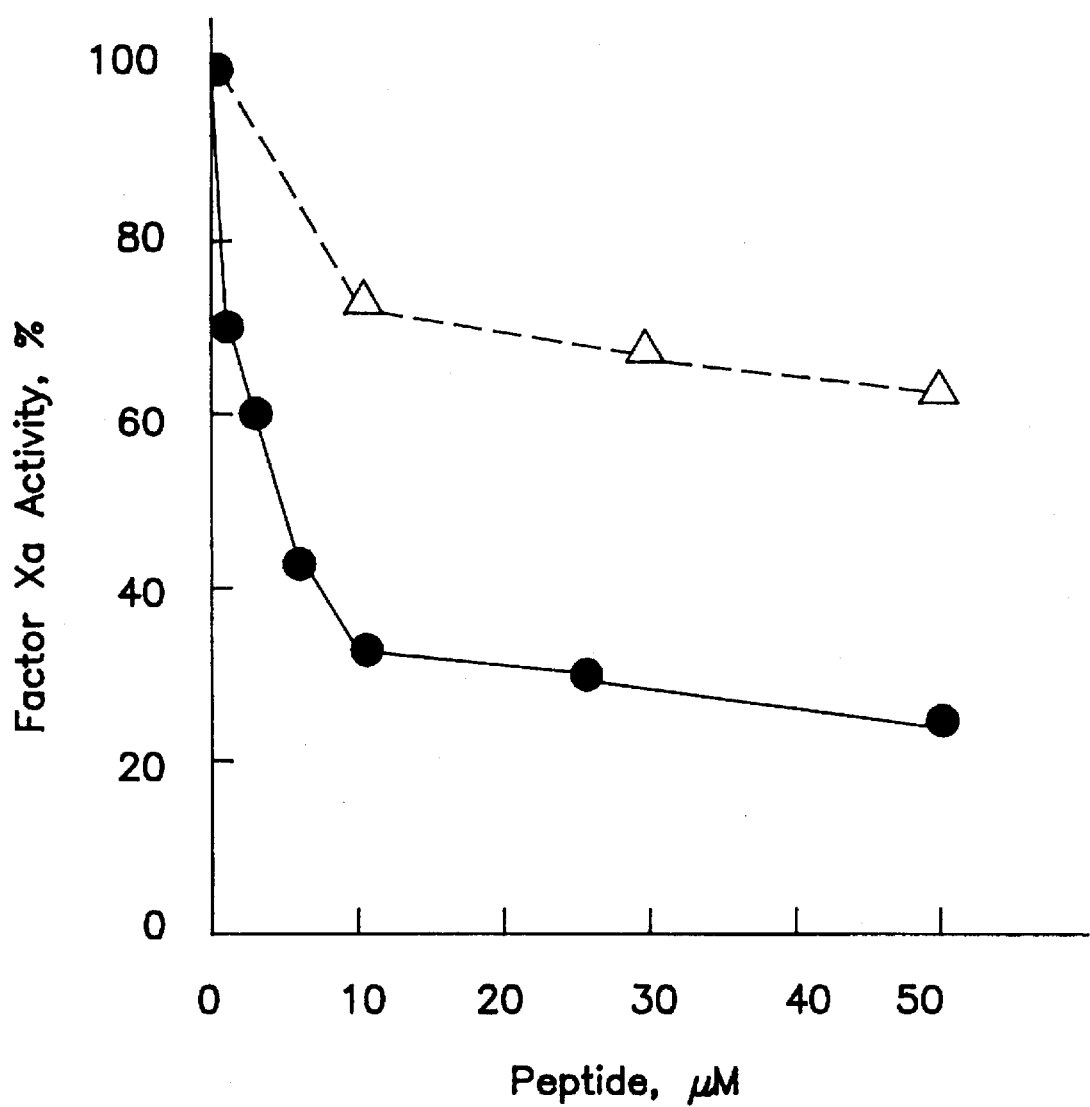
FIG. 2 illustrates factor Xa clotting activity in the presence of PC142-155. The assay was performed as described in Example 5a6). Solid circles with solid lines depict factor Xa activity of 0.15 nM factor Xa in NHP in the presence of PC142-155 and solid triangles with dashed lines depict factor Xa activity in the presence of the scrambled peptide.

The results of these assays were shown in FIGS. 1 and 2. In FIG. 1, PC311-325 inhibited Factor Xa clotting activity in NHP with 50% inhibited at 7 µM peptide whereas the control peptide with the randomized sequence only slightly affected Factor Xa activity with 30% inhibition at 100 µM peptide. Thus, in the absence of exogenously added APC, peptide PC311-325 was itself anticoagulant. The same result was observed with PC142-155 where Factor Xa clotting activity in NHP was decreased to 50% with 10 µM of admixed PC142-155 as shown in FIG. 2. The scrambled control peptide only slightly interfered with Factor Xa activity with 37% inhibition at 50 µM peptide.

Both peptides, PC311-325 and PC142-155, in the absence of exogenously admixed APC were effective at inhibiting coagulation mediated by Factor Xa.

7) Prothrombinase Assay

In order to test whether PC311-325 or PC142-155 interfered with the interaction of Factor Xa or prothrombin with the cofactor Factor Va, studies using purified proteins were done in prothrombinase assays.

Prothrombinase assays were performed as described in Example 5a5) for the Factor Va assay using a final concentration of 0.4 nM Factor Va. In the absence of Factor Va or phospholipid vesicles, the time intervals for quenching the prothrombinase by adding aliquots of the prothrombinase admixture to a solution containing 10 mM EDTA were five minutes instead of one minute as for the presence of Factor Va and phospholipid vesicles. Synthetic peptides were pre-maintained with Factor Va for 20 minutes at 22° C. or, in the case of assays lacking Factor Va, with prothrombin in the presence of phospholipid vesicles for 20 minutes at 22° C. Prothrombinase activity, expressed as the amount of generated thrombin per unit of time, was based on thrombin amidolytic activity towards the chromogenic substrate S-2238.

Figure 3:
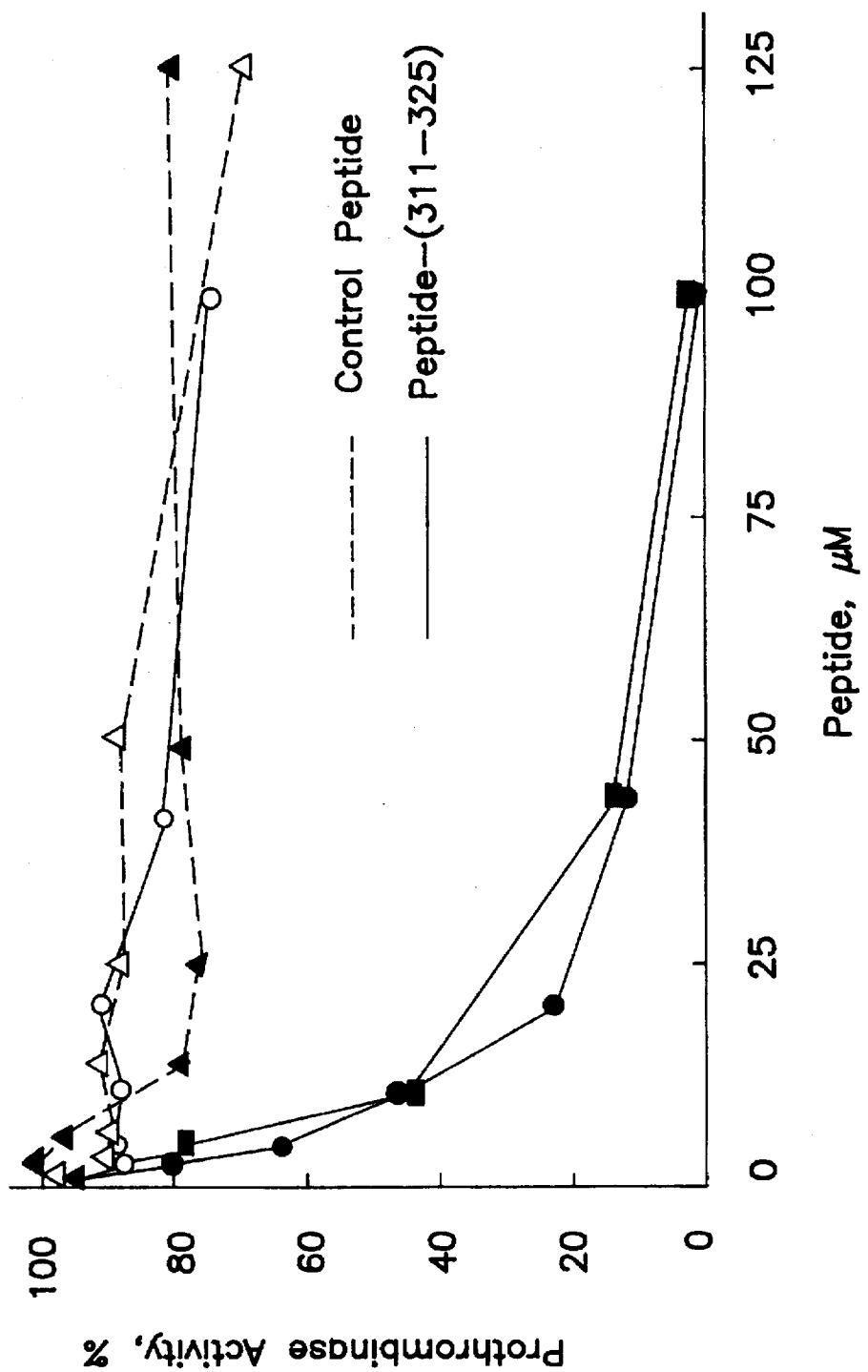
FIG. 3 illustrates prothrombinase activity in the presence of PC311-325. The assay was performed using 1 nM factor Xa, 0.4 nM factor Va, 1.2 µM prothrombin and 2.5 nM factor Xa in the absence of factor Va in TBS-BSA, 2.5 mM $CaCl_2$, pH 7.4. Unless otherwise specified all prothrombinase assays were carried out in the presence of 50 µM phospholipid vesicles. In all cases solid symbols indicate prothrombinase activity in the presence of factor Va whereas open symbols indicate prothrombinase activity in the absence of factor Va. Solid circles with solid lines indicate prothrombinase activity (with factor Va) in the presence of PC311-325, solid squares with solid lines indicate prothrombinase activity (with factor Va) in the presence of PC311-325 but in the absence of phospholipid vesicles and solid triangles with dashed lines indicate prothrombinase activity (with factor Va) in the presence of the control peptide. Open circles with solid lines denote prothrombinase activity (without factor Va) in the presence of PC311-325 and open triangles with dashed lines denote prothrombinase activity (without factor Va) in the presence of the control peptide.
Figure 4:
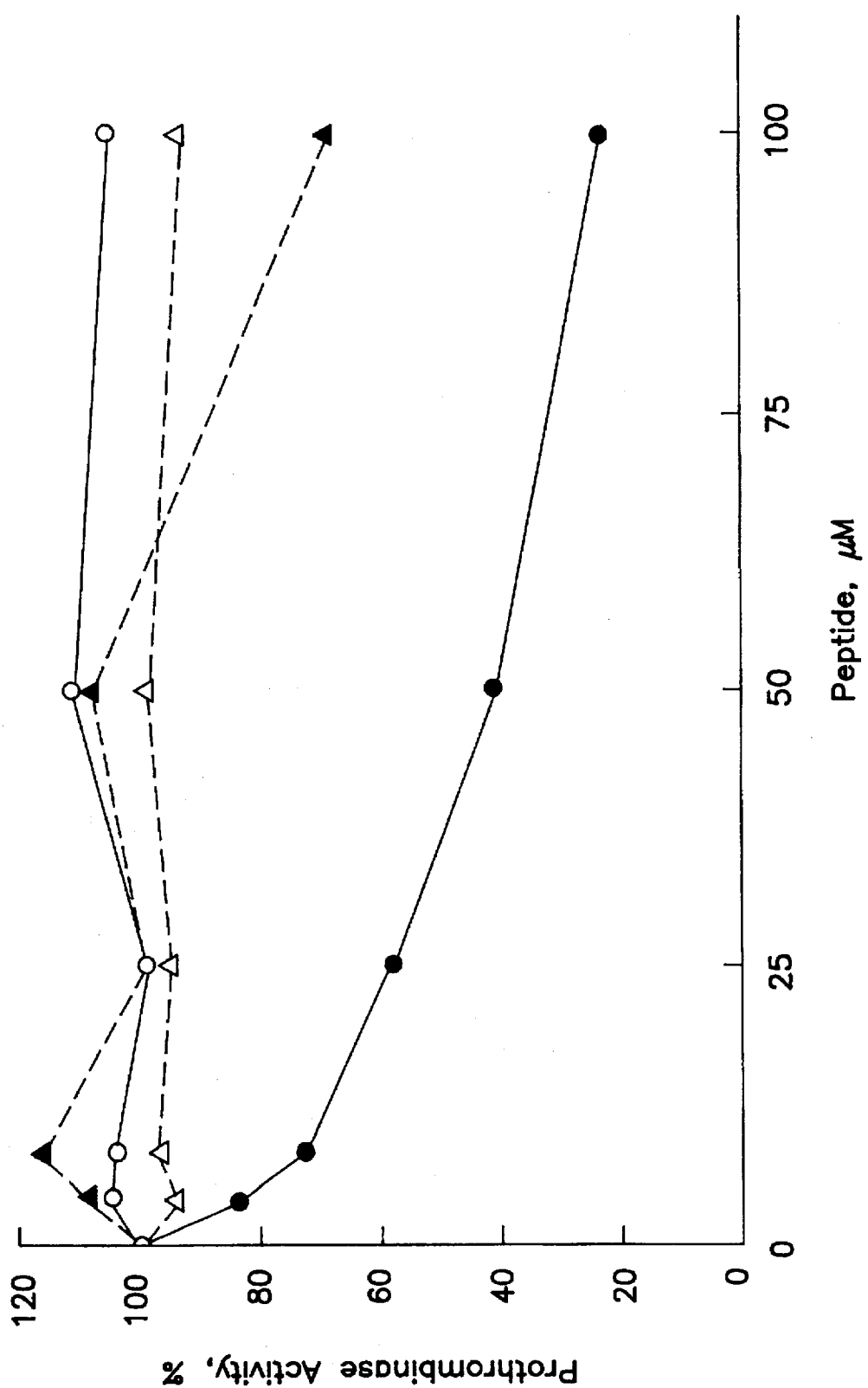
FIG. 4 illustrates prothrombinase activity in the presence of PC142-155. The assay was performed using 1 nM factor Xa, 0.4 nM factor Va, 1.2 µM prothrombin and 2.5 nM factor Xa in the absence of factor Va in TSB-BSA, 2.5 mM $CaCl_2$, 50 µM phospholipid vesicles, pH 7.4. In all cases solid symbols indicate prothrombinase activity in the absence of factor Va. Solid circles with solid lines indicate prothrombinase activity (with factor Va) in the presence of PC142-155 and solid triangles with dashed lines indicate prothrombinase activity (with factor Va) in the presence of the scrambled peptide. Open circles with solid lines denote prothrombinase activity (without factor Va) in the presence of PC142-155 and open triangles with dashed lines denote prothrombinase activity (without factor Va) in the presence of the scrambled peptide.

PC311-325 potently inhibited the generation of thrombin in the prothrombinase assay in the presence of Factor Va (in the absence or presence of phospholipid vesicles) with 50% inhibition of prothrombinase activity at 8 µM peptide as shown in FIG. 3. However, in the absence of Factor Va even at concentrations up to 200 µM of PC311-325, very little if any significant inhibition of prothrombinase activity occurred. This degree of inhibition of prothrombinase activity was also observed for the control peptide in the absence as well as in the presence of Factor Va. PC142-155 inhibited the generation of thrombin in the prothrombinase assay in the presence of Factor Va with 50% inhibition of prothrombinase activity at 40 µM peptide. However, in the absence of Factor Va even at concentrations up to 250 µM of PC142-155, no significant effect on prothrombinase activity occurred. A small amount of inhibition of prothrombinase activity was also observed for the scrambled peptide with a random sequence in the presence of Factor Va but not in the absence of Factor Va.

The unexpected findings were that both PC311-325 and PC142-155 potently inhibited Factor Xa clotting activity either in clotting assays in plasma with 50% inhibition at 7 µM PC311-325 and at 5 mM PC142-155 or in prothrombinase assays with 50% inhibition at 8 µM PC311-325 and at 40 mM PC142-155. No significant inhibition of prothrombinase activity occurred in the absence of Factor Va. Thus, the presence of Factor Va is a requirement for the inhibitory effect of the peptide. PC311-325, however, had no significant effect on Factor Xa or thrombin amidolytic activity towards chromogenic substrates and no effect on the clotting of purified fibrinogen by thrombin. PC311-325 inhibited prothrombinase activity in the absence or presence of phospholipids. These observations exclude the possibilities that the peptide has anticoagulant properties because it inhibits the binding of the components of the prothrombinase complex to the phospholipid vesicles, because it binds to the active site of Factor Xa or thrombin, or because it interferes with thrombin interaction with fibrinogen or fibrin polymerization. These data in combination with the inhibitory effect of PC311-325 on APC inactivation of Factor Va suggest that the sequence of residues 311–325 in APC provides a Factor Va binding site and that the PC311-325 binds Factor Va thereby interfering with both inactivation of Factor Va and expression of Factor Xa activity in the prothrombinase complex.

For PC142-155, no significant inhibition of prothrombinase activity occurred in the absence of Factor Va. Thus, the presence of Factor Va is a requirement for the inhibitory effect of the peptide. The scrambled peptide with a randomized sequence of PC142-155, although less potent than PC142-155, significantly inhibited Factor Xa clotting activity and prothrombinase activity in the presence of Factor Va but not in the absence of Factor Va with 40% inhibition at 50 µM and 100 µM peptide, respectively.

PC142-155 as well as the scrambled peptide had no significant effect on Factor Xa or thrombin amidolytic activity towards chromogenic substrates and no effect on the clotting of purified fibrinogen by thrombin. These observations exclude the possibilities that the peptides have anticoagulant properties because it binds to the active site of Factor Xa or thrombin, or because it interferes with thrombin interaction with fibrinogen or fibrin polymerization. These data in combination with the inhibitory effect of PC142-155 on APC inactivation of Factor Va suggest that the sequence of residues 142–155 in APC provides a Factor Va binding site and that the PC142-155 binds Factor Va thereby interfering with both inactivation of Factor Va and expression of Factor Xa activity in the prothrombinase complex.

b. Inhibition of APC by Anti-PC317-331 and PC142-155 Antibodies

The immunoaffinity-purified polyclonal anti-PC317-331 and PC142-155 antibodies prepared in Examples 2 and 3 were screened for their ability to inhibit APC anticoagulant activity in four different assays as described above in which synthetic PC-derived peptides were evaluated. The assays were used to verify the implications from the data obtained by PC311-325 and PC142-155 that this region in APC is essential for the protein's anticoagulant activity and for the recognition of the macromolecular substrates, activated Factors V (Va) and VIII (VIIIa).

1) Activated Partial Thromboplastin Time (APTT) Coagulation Assay

The effect of the immunoaffinity-purified polyclonal anti-PC317-331 and PC142-155 antibodies on APC anticoagulant activity was determined using the APTT assay as described in Example 5a1).

For the APTT assay, APC was prepared as described in Example 2c2). The specific anticoagulant activity of APC was determined to be 250 Units/mg. The concentration of the APC used in the assay was initially optimized with respect to the sensitivity of the assay towards APC-induced prolongation of clotting time compared to clotting time without APC.

Once the optimal concentration of APC was determined, anti-PC317-331 was separately admixed ranging in concentration from 0 to 40 µg/ml with APC in 200 µl of TBS-BSA and 15 mM $CaCl_2$ at pH 7.4 to form an anti-PC317-331-APC immunoreaction admixture pre-maintenance solution. For APTT assays in the presence of NHP, APC was used at a concentration of 2.5 nM. For APTT assays in the presence of PSDP, APC was used at a concentration of 5 nM. The resulting admixtures were maintained for 30 minutes at 37° C. to allow formation of an immunoreaction product. Separate aliquots of APC maintained under the same conditions in the absence of anti-PC317-331 antibody but in the presence of non-immune rabbit IgG served as controls for the inhibitory effect of anti-peptide antibodies on APC anticoagulant activity. Concurrently, 100 µl of NHP and 100 µl APTT-reagent Thrombosil (Ortho Diagnostics) were admixed together and maintained for 200 seconds at 37° C. to form a plasma-reagent admixture. In some experiments, PSDP was used in the place of NHP to determine the effect of Protein S on the assay system. Coagulation was then initiated by the admixture of 200 µl of the pre-maintenance solution containing TBS-BSA and 15 mM $CaCl_2$ with or without the APC which was either exposed to anti-PC317-331 antibody or not. The time for clot formation was measured as described in Example 5a1). The anti-PC317-331 antibody effect was determined in duplicate. The results of the APTT assays are discussed below with the results from similar analyses using the Xa-1-stage coagulation assay.

APTT assays in the presence of anti-PC142-155 were performed as described above for anti-PC317-331. The results of these experiments are discussed below with those obtained from similar analyses using the Xa-1-stage coagulation assay.

2) Xa-1-Stage Coagulation Assay

For testing the inhibition of the anti-PC317-331 antibody on APC activity described above, Xa-1-stage coagulation assays were also performed as described in Example 5a2). Anti-PC317-331 antibody was prepared as described above and separately admixed with 60 nM APC in 200 µl of 0.31 nM human Factor Xa prepared as described in Examples 5a2) and 5a5) in TBS-BSA and 15 mM $CaCl_2$ at pH 7.4 to form an anti-PC317-331 antibody-APC pre-maintained immunoreaction admixture. The resulting admixtures were maintained for 30 minutes at 37° C. to allow formation of an immunoreaction product. Separate aliquots of APC maintained under the same conditions in the absence of anti-PC317-331 antibody but in the presence of non-immune rabbit IgG served as controls for the inhibitory effect of anti-PC317-331 antibody on APC anticoagulant activity. Concurrently, 100 µl of NHP and 100 µl of 200 µg/ml of rabbit brain cephalin (Sigma) were admixed and maintained for 200 seconds at 37° C. to form a plasma-phospholipid admixture. In some experiments, Factor VIII deficient plasma (George King Bio-Medical, Inc.) was used in the place of NHP to determine the effect of Factor VIII on the assay system. Coagulation was then initiated by the admixture of 200 µl of the pre-maintained mixture containing 0.31 nM human Factor Xa prepared as described in Examples 5a2) and 5a5) in TBS-BSA containing 15 mM $CaCl_2$ with or without 60 nM of APC which was either exposed to anti-PC317-331 antibody or not.

The time for clot formation was measured as described in Example 5a2). The effects of anti-PC317-331 antibody were determined in duplicate. The results of the inhibition of APC anticoagulant activity by anti-PC317-331 as measured in APTT and Xa-1-stage coagulation assays revealed that anti-PC317-331 inhibited APC anticoagulant activity in both assays in NHP as well as in PSDP. The dose-response of anti-PC317-331 antibody inhibition of APC anticoagulant activity in NHP was similar to that observed in PSDP and in Factor VIII deficient plasma with a 50% inhibition occurring at 50 to 100 nM of anti-PC317-331 antibody. The same dose-response curve was observed in a Xa-1-stage assay using PSDP. The anti-PC317-331 antibody had no effect on coagulation assays performed in the absence of added APC. Non-immune polyclonal rabbit IgG, that failed to recognize PC or APC as determined by ELISA, did not inhibit APC anticoagulant activity. These results are similar to those obtained with coagulation assays performed in the presence of inhibitory synthetic peptides (refer to Examples 5a1) and 5a2)).

Thus, the anti-PC317-331 antibody is highly specific for the peptide against which it was raised as described in Example 2c but is also highly specific for APC and PC as well as indicated by the inhibitory effects of APC anticoagulant activity and indicated by the fact that the anti-PC317-331 antibody had no effect on APTT and Xa-1-stage coagulation assays in the absence of APC. The fact that the dose-response curve for inhibiting APC anticoagulant activity in NHP was almost identical to that observed in PSDP indicates that the antibody does not interfere with the interaction of APC with its cofactor protein S. Thus, residues 317-331 of APC are not involved with interactions with protein S.

The anti-PC142-155 antibody was used in Xa-1-stage coagulation assays as described above for anti-PC317-331 to determine if the anti-peptide antibody inhibited APC anticoagulant activity. The anti-PC142-155 antibody inhibited APC anticoagulant activity in APTT assays in NHP as well as in PSDP at 2.5 nM and 5.0 nM APC, respectively, with 50% inhibition at 33 nM antibody. A similar dose-response of anti-PC142-155 antibody on APC anticoagulant activity was obtained in a Xa-1-stage assay in Factor VIII-deficient plasma with 50% inhibition of APC activity at 187 nM antibody using a final concentration of 30 nM APC. The anti-peptide antibody had no effect on APTT or Xa-1-stage coagulation assays performed in the absence of added APC. Control non-immune polyclonal rabbit IgG, that failed to recognize APC or PC as judged by ELISA assays, had no significant effect on APC anticoagulant activity.

Thus, similar to PC142-155, the anti-PC142-155 antibody inhibited APC anticoagulant activity in APTT and Xa-1-stage assays in NHP and PSDP with 50% inhibition at 33 nM antibody in APTT assays. The inhibition of APC by anti-PC142-155 antibody was specific since non-immune rabbit-IgG showed no effect on APC anticoagulant activity and the anti-(142–155) antibody has no effect on the coagulation assays in the absence of APC. The fact that the dose response for anti-PC142-155 antibody for inhibition of APC in NHP is similar to that observed in PSDP indicates that binding of the antibody to its epitope on APC does not interfere with the interaction of APC with its cofactor, protein S. Thus, based on these data together with the data obtained using the peptide PC142-155, residues 142–155 are determined to be essential for activity and that these residues are not involved in APC interactions with protein S.

3) Amidolytic Activity of APC Assay

The effect of anti-PC317-331 antibody on the amidolytic activity of APC was evaluated to determine if the antibody inhibited APC anticoagulant activity by blocking a region in or close to the active site of the enzyme involved in cleavage of a small substrate such as S-2366 (Kabi-Vitrum) or involved in the site of interaction with the recombinant mutant (Arg$^{358}$)α$_1$-AT, the latter of which is described in Example 564) below.

The amidolytic activity of APC toward the peptide substrate S-2366 was measured in the presence of anti-PC317-331 antibody. For the assay, 100 µl of 15 nM APC, prepared in Example 2c2), were admixed with separate aliquots of anti-PC317-331 antibody ranging in concentration from 0.0 to 500 nM prepared in TBS-BSA at pH 7.4 containing 0.02% NaN$_3$ and 2 mM CaCl$_2$ to form APC-anti-PC317-331 antibody immunoreaction admixtures. After maintenance of the admixtures for 30 minutes at 37° C. to allow formation of immunoreaction products, 50 µl of 2.4 mM S-2366 in the same buffer was admixed to initiate the amidolytic reaction. The hydrolysis of the substrate was monitored by the change in absorbance at 405 nm over time using an EL312 Microplate Bio-Kinetics Reader (BIO-TEK Instruments, Inc. Vt.).

In contrast to the inhibitory effect of anti-PC317-331 antibody on APC anticoagulant activity, 0.0 to 500 nM anti-PC317-331 antibody admixed with 15 nM APC for 30 minutes at 37° C. had no influence on APC amidolytic activity using the chromogenic substrate S-2366 and gave a value in the same range as those obtained using peptides, as shown in Table 7. These results indicate that anti-PC317-331 antibody, like peptides PC311-325 and PC314-331, does not exert inhibitory effects of APC anticoagulant activity by blocking a region in or close to the active site of the enzyme involved in cleavage of a small substrate.

Similar analyses were performed with anti-PC142-155 as described above for anti-PC317-331. As with anti-PC317-331 as well as peptide PC142-155, anti-PC142-155 had no effect on APC amidolytic activity. The results were similar to those shown for peptides in Table 7. Thus, anti-PC142-155 antibody also does not exhibit inhibiting effects on APC activity by blocking a region close to the active site of the enzyme involved in the cleavage of a small substrate.

4) Inhibition of APC by Recombinant Mutant α$_1$-Anti-Trypsin Assay

Since the number of amino acid residues involved in neutralization of APC by macromolecular plasma protease inhibitors is likely to be higher than the number of residues of APC involved in the cleavage of a small chromogenic substrate such as S-2366, the effect of anti-PC317-331 antibody on the time course of inhibition of APC by a larger pseudo-substrate, such as recombinant mutant (Arg$^{358}$)-α$_1$-AT was evaluated. Kinetic studies of inhibition of APC were performed with the high affinity mutant α$_1$-AT pseudo-substrate. For the assay, 60 µl of 36 nM APC was admixed with 580 nM anti-PC317-331 antibody to form an APC-antibody immunoreaction admixture which was maintained for 30 minutes at 37° C. to allow formation of immunoreaction product in TBS-BSA at pH 8.0 containing 0.02% NaN$_3$ and 2 mM CaCl$_2$. After the maintenance period, the APC-antibody immunoreaction product was then admixed with 60 µl of 200 nM recombinant (Arg$^{358}$)-α$_1$-AT prepared as described in Example 5a4). At selected time points, 8 µl aliquots from the reaction admixture were removed and admixed with 300 µl 10.8 mM S-2366 in TBS-BSA at pH 7.4 containing 0.02% NaN$_3$ to initiate the hydrolysis of S-2366 by APC. The change in absorbance was measured over time as described in the amidolytic assay. Controls without the inhibitor α$_1$-AT in the absence or presence of antibody were included in the assay.

APC activity in the controls performed above was constant with a deviation of 5% over the course of the experiment. Anti-PC317-331 antibody at a final concentration of 290 nM did not have any significant effect on the time course of inhibition of 18 nM APC by 100 nM recombinant (Arg$^{358}$)α$_1$-AT. In addition, APC activity in the presence of either anti-PC317-331 antibody but in the absence of α$_1$-AT was not inhibited over the assayed time course of 10 minutes. These results, which are consistent with the results obtained with synthetic peptides and with the amidolytic assay results described above provide additional support that the antibody directed against the peptide corresponding to the 317-331 amino acid residue sequence on the heavy chain of APC does not act by blocking a region in or close to the active site of the enzyme or other important regions involved in interactions with the recombinant mutant α$_1$-AT. Similar analyses with anti-PC142-155 were performed as described above with the exception that the antibody was used at a final concentration of 450 nM. The same results were achieved thus confirming that amino acid residues 142-155 of APC light chain do not act by blocking a region in close to the active site of the APC enzyme.

6. Identification of Two Exosites on APC

The region comprising residues 390-404 was previously shown to represent an exosite for the binding of APC to its macromolecular substrates, Factor Va and possibly VIIIa. Two additional exosites have been found as herein described as comprising residues 311-325 and 142-155 of the heavy and light chain of APC. Thus, it seems that APC has at least three spatially distinct exosites for recognition of Factor Va, the region of residues 390-404, 311-325 and 142-155, and that the interactions of APC with its substrate Factor Va are remarkably extensive. The above mentioned three peptides inhibit both APC anticoagulant activity and APC inactivation of Factor Va. However, PC311-325 as well as PC142-155 have additionally anticoagulant properties due to inhibition of prothrombinase activity, a property that PC390-404 lacks. The three peptides most likely exert their inhibitory effect on APC activity by binding to Factor Va. The sites on Factor Va to which PC142-155 and PC311-325 bind must be topologically distinct on Factor Va since both PC311-325 and PC142-155 inhibit the expression of Factor Va-dependent prothrombinase activity. Factor Xa protects Factor Va from inactivation by APC suggesting that both enzymes might share certain binding sites on Factor Va. In this case, both PC311-325 and PC142-155 presumably bind to such a hypothesized common binding site in Factor Va thereby blocking both binding of APC and binding of Factor Xa. Albeit less likely, it is also possible that both PC311-325 and PC142-155 block binding of prothrombin to Factor Va in the prothrombinase complex or that it induces a conformational change in Factor Va thus rendering it much less active as cofactor.

The data showing that the anti-PC317-331 antibody inhibits APC anticoagulant activity is consistent with the existence and importance of the suggested exosite involving residues 311-325. However, it is possible that the epitope(s) of the antibody are located in the carboxyterminal part of residues 317-331 that does not overlap with residues 311-325, i.e., in 326-331. Thus, the antibody could bind to an exosite different from that which is competitively inhibited by PC311-325. Nevertheless, if this is the case, both exosites seem to be involved in APC interactions with the macromolecular substrates, Factors Va and VIIIa. The heavy chain of APC is homologous to other serine proteases and this class of enzymes has a common three dimensional structure and this allows some inferences about structure-function relationships of APC using models based on structurally conserved regions of homologous enzymes. However, any inferences where the hypothetical exosite(s) might be located based on the x-ray crystallographic structure of chymotrypsin or trypsin are limited because human PC has an insertion of four amino acids preceding residue 307 in human PC.

Although the sequence of residues 311–325 in human PC is highly conserved compared to the bovine sequence (Table II), bovine PC does not have this insertion. This insertion could potentially have a significant influence on the structure of the region comprising residues 311–325. Nevertheless, the hypothesized exosite is likely located where the homologous residues 134–148 of trypsin are found in the three-dimensional x-ray crystallographic model of trypsin. Residues 134–143 in trypsin, homologous to residues 311–320 in PC, form an exposed loop on the surface of the catalytic domain whereas residues 144–148, homologous to 321–325 in PC, are rather buried in the structure. Thus, based on the trypsin model, this latter sequence is unlikely to be involved in APC interactions with substrates whereas residues 311–320 of PC are probably surface exposed and available for substrate recognition.

The data showing that the anti-PC142-155 antibody inhibits APC anticoagulant activity is consistent with the existence and importance of the suggested exosite involving residues 142–155.

7. Identification of Anticoagulant Polypeptides Derived From Blood Coagulation Serine Proteases A variety of polypeptides were synthesized having the amino acid residue sequences shown in Table 3, which sequences were derived from Factor IX, Factor X and prothrombin. These polypeptides were then tested for their ability to inhibit coagulation as measured by several different assays described below that include a Factor Xa-1 assay, a Factor IXa-1 assay, a prothrombinase assay and a tenase assay.

a. Factor Xa-1 Stage Clotting Assay

The Factor Xa-1 Stage assay was conducted as described in Example 5a6). In that assay, the $IC_{50}$ for peptides PT557-571, PT463-478, PT473-487, PT481-495, X404-418, X415-429 and X329-344 were 50, >500, 25, >500, 50, 115, and 500, respectively. These data indicate that the above polypeptides inhibit coagulation. In addition, the fact that the PT peptides also inhibited indicates that there is sufficient homology between the exosite peptides from PT to interact with Factor Xa and inhibit Xa activity.

b. Factor IXa-1 Stage Clotting Assay

The Factor IXa-1 Stage assay was conducted essentially as the Factor Xa-1 Stage clotting assay above, except that Factor Xa was omitted, and Factor IXa was added in its place. In that assay, the $IC_{50}$ for peptides X404-418, X415-429, IX395-409, IX400-414, IX315-330, and IX321-335 were 50, 0, 25, 50, 30 and 30. These data indicate that the above polypeptides inhibit coagulation. In addition, the fact that the X peptides also inhibited indicates that there is sufficient homology between the exosite peptides from X to interact with Factor IXa and inhibit IXa activity.

c. Prothrombinase Assay

The prothrombinase assay was conducted as described in Example 5a5). The assay was conducted in the presence of Factor Va including the following reagents: 1 nM Xa, 0.4 nM Va, 1.2 uM prothrombin; and was conducted in the absence of Factor Va including the following reagents: 2.5 nM Xa, 1.2 uM prothrombin.

Using peptides X404-418 or PT473-487, there was no appreciable inhibition of prothrombinase activity when tested in the absence of Factor Va, but in the presence, the $IC_{50}$ for X404-418 was about 75 uM, and for PT473-487 was about 10 uM. Using peptides PT557-571 or X415-429, there was inhibition in the presence or absence of Factor Va, with the $IC_{50}$ for X415-429 at about 500 uM both + or − Factor Va, and for PT557-571 at about 40 uM (+Va) and 80 uM (−Va). These data indicate at least that both the PT peptides and the X peptides tested exhibited significant anticoagulant activity.

d. Factor Xa General Assay "Tenase" in the Presence of Factor VIIIa

The tenase assay was conducted both in the presence and absence of Factor VIIIa. The procedure for the tenase assay varied depending on this variable and is described hereafter.

Peptides prepared in Example 1 were dissolved in water and then ½ into 50 mM Barbital, 200 mM NaCl, 0.2% NAN3, 2.5 mg/ml Ovalbumin (5 times recrystallized, salt free, from American Biorganics Inc., New York, pH=7.5). Phospholipid vesicles were prepared as previously described in Example 5a5) into 25 mM Barbital 100 mM NaCl, 0.1% NaN3 pH 7.5 (BBS). Before using them, they were made 250 μM into BBs +1.25 mg/ml Ovalbumin (BBS+OV) containing $CaCl_2$ for a final concentration of 25 mM and they were preincubated for 10 minutes at 37° C. These vesicles were allowed to cool to room temperature before being added to the reaction mixture.

Monoclate P (Armour Pharmaceutical, Chicago) 114 U VIII:C/ml frozen in water was thawed at 37° C. and immediately diluted to 6 U/ml into BBS+OV (22° C.). A 0.35 nM thrombin-containing solution (Enzyme Research Labs., Southbend, Ind.) was prepared by admixing 1/100 volume of stock solution containing 35 nM in BBS+OV, and maintained for 3 minutes at 22° C. Thrombin activity was stopped by adding 1/100 volume of a 50 μM stock solution in 1 mM HCl of Phe-Pro-Arg-Chloromethyl ketone (PPACK, Bachem Feinchmikallen AG, Bubendorf, Switzerland). Controls that had PPACK added before Thrombin showed less than 10% Xa generation. Controls where no Monoclate P was added showed no amidolytic activity towards the chromogenic substrate S-2765 (Kabi, Stockholm, Sweden). The thrombin treated Monoclate P was used immediately in the Xa generation assay.

For the assay, 30 μl of peptide dilutions or BBS+OV as 0 μM peptide control were admixed with 30 μl of thrombin-treated Monoclate P and maintained 10 minutes at 22° C. Then 30 μl of $CaCl_2$-phospholipid vesicles prepared as described above were added, followed immediately by 30 μl of 3.5 nM factor IXaβ (Enzyme Research Labs) in BBS+OV. The reaction was started by adding 30 μl of 250 nM factor X (Enzyme Research Labs) in BBS+OV. All reagents were at 22° C.

Aliquots of 20 μl were drawn at time 0, 1, 2, 3, 4 and 5 minutes of maintenance at 22° C. and diluted to 160 μl of 50 mM TrisHCl, 100 mM NaCl, 5 mM EDTA and 0.1 mg/ml Ovalbumin pH=8.0. Once all aliquots were drawn, 20 μl 2.0 mM S-2765 were added and the increase of A 405 at 22° C. was recorded in a model EL 312 Microplate Biokinetics Reader (BIO-TEK Instruments Inc., Vermont).

The increase of A 405 showed a linear dose-response curve at final concentrations between 0 and 0.7 nM factor IXaβ and between 0 and 1.2 U/ml thrombin treated Monoclate P, and showed saturation at concentrations of factor X above 40 nM. No amidolytic activity was observed when factor X was omitted from the reaction mixture.

Factor Xa Generation in the Absence of Factor VIII

Phospholipid vesicles prepared as described above were admixed with BBS+OV containing $CaCl_2$ to obtain final concentrations of 312.5 µM vesicles and 20 mM $CaCl_2$, and were premaintained for 10 minutes at 37° C. Before admixing, all the reagents were maintained for 5 minutes in a 37° C. waterbath.

For the assay, 100 µl of the phospholipid $CaCl_2$ mix were admixed with 100 µl of peptide dilutions in BBS+OV or BBS+OV (as 0 µM peptide control) and 25 µl of 100 nM factor IXaβ in BBS+OV. The reaction was started immediately by adding 25 µl of 10 µM factor X in BBS+OV. All experiments were done at 37° C.

Aliquots of 40 µl were drawn at time 0, 5, 10, 15, 20 and 25 minutes of incubation at 37° C. and diluted to 140 µl 50 mM TrisHCl, 100 mM NaCl, 10 mM EDTA, and 1.25 mg/ml Ovalbumin pH=8.0. Once all aliquots were drawn, 20 µl 20.0 mM S-2765 were added and the increase of A 405 at 22° C. was recorded in a model EL 312 Microplate Biokinetics Reader.

The results of the tenase assay indicate that peptides IX315-330 and IX395-409 exhibited strong inhibition of tenase in the presence of Factor VIIIa, at about an $IC_{50}$ of 2 uM and 6 uM, respectively, and an $IC_{50}$ of about 40–60 uM each in the absence of VIIIa. Similarly, peptides IX321-335 and IX400-414 exhibited inhibition of tenase in the presence of Factor VIIIa, at about an $IC_{50}$ of 100–140 uM each, and an minimal inhibition in the absence of VIIIa. Peptides X404-418 and X415-429 inhibited tenase in the presence of VIIIa with an $IC_{50}$ of about 150 and 45 uM, respectively. These data show that the peptides tested inhibit tenase activity, and therefor inhibit coagulation at micromolar concentrations.

The foregoing specification, including the specific embodiments and examples, is intended to be illustrative of the present invention and is not to be taken as limiting. Numerous other variations and modifications can be effected without departing from the true spirit and scope of the present invention.

What is claimed is:

1. A polypeptide having an amino acid residue sequence that consists of an amino acid residue sequence shown at the residue positions indicated in parenthesis selected from the group consisting of: (SEQ ID NO 1:142–155), (SEQ ID NO 1:311–325), (SEQ ID NO 1:311–331), (SEQ ID NO 2:315–330), (SEQ ID NO 2:316–330), (SEQ ID NO 2:316–336), (SEQ ID NO 2:321–330), (SEQ ID NO 2:321–335), (SEQ ID NO 2:395–409), (SEQ ID NO 2:395–414), (SEQ ID NO 2:400–409), (SEQ ID NO 2:400–414), (SEQ ID NO 3:329–344), (SEQ ID NO 3:330–344), (SEQ ID NO 3:330–350), (SEQ ID NO 3:404–418), (SEQ ID NO 3:409–423), (SEQ ID NO 3:415–429), (SEQ ID NO 4:463–477), (SEQ ID NO 4:463–478), (SEQ ID NO 4:473–487), (SEQ ID NO 4:474–487), (SEQ ID NO 4:474–493), (SEQ ID NO 4:481–495), (SEQ ID NO 4:557–571), (SEQ ID NO 5:289–304), (SEQ ID NO 5:290–304), (SEQ ID NO 5:290–310) and (SEQ ID NO 5:374–388), wherein each polypeptide sequence is taken from a serine protease sequence, and wherein said polypeptide in vitro inhibits 50 percent ($IC_{50}$) of the activity of said serine protease at a concentration of at least 500 micromolar.

2. A composition comprising a coagulation-inhibiting amount of a polypeptide according to claim 1.

3. The composition of claim 2 wherein said coagulation-inhibiting amount is at least 0.1 weight percent polypeptide per weight of total composition.

4. The composition of claim 2 wherein said polypeptide is dispersed in a pharmaceutically acceptable excipient.

* * * * *

SEQUENCE LISTING ( 1 ) GENERAL INFORMATION:

( i i i ) NUMBER OF SEQUENCES: 10

( 2 ) INFORMATION FOR SEQ ID NO:1:

( i ) SEQUENCE CHARACTERISTICS:
( A ) LENGTH: 419 amino acids
( B ) TYPE: amino acid
( D ) TOPOLOGY: linear ( i i ) MOLECULE TYPE: protein ( i i i ) HYPOTHETICAL: NO ( i v ) ANTI-SENSE: NO ( i x ) FEATURE:
( A ) NAME/KEY: Region
( B ) LOCATION: 1..157
( D ) OTHER INFORMATION: /note= "Protein C Light Chain"

( i x ) FEATURE:
( A ) NAME/KEY: Region
( B ) LOCATION: 158..169
( D ) OTHER INFORMATION: /note= "Protein C Activation Peptide"

( i x ) FEATURE:
( A ) NAME/KEY: Region
( B ) LOCATION: 170..419
( D ) OTHER INFORMATION: /note= "Protein C Heavy Chain"

( x i ) SEQUENCE DESCRIPTION: SEQ ID NO:1:

| Ala | Asn | Ser | Phe | Leu | Glu | Glu | Leu | Arg | His | Ser | Ser | Leu | Glu | Arg | Glu |
|---|---|---|---|---|---|---|---|---|---|---|---|---|---|---|---|
| 1 | | | | 5 | | | | | 10 | | | | | 15 | |
| Cys | Ile | Glu | Glu | Ile | Cys | Asp | Phe | Glu | Glu | Ala | Lys | Glu | Ile | Phe | Gln |
| | | | 20 | | | | | 25 | | | | | 30 | | |
| Asn | Val | Asp | Asp | Thr | Leu | Ala | Phe | Trp | Ser | Lys | His | Val | Asp | Gly | Asp |
| | | 35 | | | | | 40 | | | | | 45 | | | |
| Gln | Cys | Leu | Val | Leu | Pro | Leu | Glu | His | Pro | Cys | Ala | Ser | Leu | Cys | Cys |
| | 50 | | | | | 55 | | | | | 60 | | | | |
| Gly | His | Gly | Thr | Cys | Ile | Asp | Gly | Ile | Gly | Ser | Phe | Ser | Cys | Asp | Cys |
| 65 | | | | | 70 | | | | | 75 | | | | | 80 |

```
Arg  Ser  Gly  Trp  Glu  Gly  Arg  Phe  Cys  Gln  Arg  Glu  Val  Ser  Phe  Leu
               85                      90                      95

Asn  Cys  Ser  Leu  Asp  Asn  Gly  Gly  Cys  Thr  His  Tyr  Cys  Leu  Glu  Glu
              100                     105                    110

Val  Gly  Trp  Arg  Arg  Cys  Ser  Cys  Ala  Pro  Gly  Tyr  Lys  Leu  Gly  Asp
              115                     120                    125

Asp  Leu  Leu  Gln  Cys  His  Pro  Ala  Val  Lys  Phe  Pro  Cys  Gly  Arg  Pro
         130                     135                    140

Trp  Lys  Arg  Met  Glu  Lys  Arg  Ser  His  Leu  Lys  Arg  Asp  Thr  Glu
145                      150                     155                          160

Asp  Gln  Glu  Asp  Gln  Val  Asp  Pro  Arg  Leu  Ile  Asp  Gly  Lys  Met  Thr
              165                     170                    175

Arg  Arg  Gly  Asp  Ser  Pro  Trp  Gln  Val  Val  Leu  Leu  Asp  Ser  Lys  Lys
              180                     185                    190

Lys  Leu  Ala  Cys  Gly  Ala  Val  Leu  Ile  His  Pro  Ser  Trp  Val  Leu  Thr
         195                     200                    205

Ala  Ala  His  Cys  Met  Asp  Glu  Ser  Lys  Lys  Leu  Leu  Val  Arg  Leu  Gly
     210                     215                    220

Glu  Tyr  Asp  Leu  Arg  Arg  Trp  Glu  Lys  Trp  Glu  Leu  Asp  Leu  Asp  Ile
225                      230                     235                          240

Lys  Glu  Val  Phe  Val  His  Pro  Asn  Tyr  Ser  Lys  Ser  Thr  Thr  Asp  Asn
              245                     250                    255

Asp  Ile  Ala  Leu  Leu  His  Leu  Ala  Gln  Pro  Ala  Thr  Leu  Ser  Gln  Thr
              260                     265                    270

Ile  Val  Pro  Ile  Cys  Leu  Pro  Asp  Ser  Gly  Leu  Ala  Glu  Arg  Glu  Leu
              275                     280                    285

Asn  Gln  Ala  Gly  Gln  Glu  Thr  Leu  Val  Thr  Gly  Trp  Gly  Tyr  His  Ser
290                      295                     300

Ser  Arg  Glu  Lys  Glu  Ala  Lys  Arg  Asn  Arg  Thr  Phe  Val  Leu  Asn  Phe
305                      310                     315                          320

Ile  Lys  Ile  Pro  Val  Val  Pro  His  Asn  Glu  Cys  Ser  Glu  Val  Met  Ser
              325                     330                    335

Asn  Met  Val  Ser  Glu  Asn  Met  Leu  Cys  Ala  Gly  Ile  Leu  Gly  Asp  Arg
              340                     345                    350

Gln  Asp  Ala  Cys  Glu  Gly  Asp  Ser  Gly  Gly  Pro  Met  Val  Ala  Ser  Phe
         355                     360                    365

His  Gly  Thr  Trp  Phe  Leu  Val  Gly  Leu  Val  Ser  Trp  Gly  Glu  Gly  Cys
         370                     375                    380

Gly  Leu  Leu  His  Asn  Tyr  Gly  Val  Tyr  Thr  Lys  Val  Ser  Arg  Tyr  Leu
385                      390                     395                          400

Asp  Trp  Ile  His  Gly  His  Ile  Arg  Asp  Lys  Glu  Ala  Pro  Gln  Lys  Ser
              405                     410                    415

Trp  Ala  Pro
```

( 2 ) INFORMATION FOR SEQ ID NO:2:

( i ) SEQUENCE CHARACTERISTICS:
        ( A ) LENGTH: 415 amino acids
        ( B ) TYPE: amino acid
        ( D ) TOPOLOGY: linear ( i i ) MOLECULE TYPE: protein ( i i i ) HYPOTHETICAL: NO ( i v ) ANTI-SENSE: NO ( i x ) FEATURE:
    ( A ) NAME/KEY: Region
    ( B ) LOCATION: 1..145
    ( D ) OTHER INFORMATION: /note= "Factor IX Light Chain"

( i x ) FEATURE:
    ( A ) NAME/KEY: Region
    ( B ) LOCATION: 146..180
    ( D ) OTHER INFORMATION: /note= "Factor IX Activation
        Peptide"

( i x ) FEATURE:
    ( A ) NAME/KEY: Region
    ( B ) LOCATION: 181..415
    ( D ) OTHER INFORMATION: /note= "Factor IX Heavy Chain"

( x i ) SEQUENCE DESCRIPTION: SEQ ID NO:2:

| Tyr | Asn | Ser | Gly | Lys | Leu | Glu | Glu | Phe | Val | Gln | Gly | Asn | Leu | Glu | Arg |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Glu | Cys | Met | Glu | Glu | Lys | Cys | Ser | Phe | Glu | Glu | Pro | Arg | Glu | Val | Phe |
|     |     |     | 20  |     |     |     |     | 25  |     |     |     |     | 30  |     |     |

| Glu | Asn | Thr | Glu | Lys | Thr | Thr | Glu | Phe | Trp | Lys | Gln | Tyr | Val | Asp | Gly |
|     |     | 35  |     |     |     |     | 40  |     |     |     |     | 45  |     |     |     |

| Asp | Gln | Cys | Glu | Ser | Asn | Pro | Cys | Leu | Asn | Gly | Gly | Ser | Cys | Lys | Asp |
|     | 50  |     |     |     |     | 55  |     |     |     |     | 60  |     |     |     |     |

| Asp | Ile | Asn | Ser | Tyr | Glu | Cys | Trp | Cys | Pro | Phe | Gly | Phe | Glu | Gly | Lys |
| 65  |     |     |     |     | 70  |     |     |     |     | 75  |     |     |     |     | 80  |

| Asn | Cys | Glu | Leu | Asp | Val | Thr | Cys | Asn | Ile | Lys | Asn | Gly | Arg | Cys | Glu |
|     |     |     |     | 85  |     |     |     |     | 90  |     |     |     |     | 95  |     |

| Gln | Phe | Cys | Lys | Asn | Ser | Ala | Asp | Asn | Lys | Val | Val | Cys | Ser | Cys | Thr |
|     |     |     | 100 |     |     |     |     | 105 |     |     |     |     | 110 |     |     |

| Glu | Gly | Tyr | Arg | Leu | Ala | Glu | Asn | Gln | Lys | Ser | Cys | Glu | Pro | Ala | Val |
|     |     |     | 115 |     |     |     |     | 120 |     |     |     |     | 125 |     |     |

| Pro | Phe | Pro | Cys | Gly | Arg | Val | Ser | Val | Ser | Gln | Thr | Ser | Lys | Leu | Thr |
|     |     | 130 |     |     |     |     | 135 |     |     |     |     | 140 |     |     |     |

| Arg | Ala | Glu | Ala | Val | Phe | Pro | Asp | Val | Asp | Tyr | Val | Asn | Pro | Thr | Glu |
| 145 |     |     |     |     | 150 |     |     |     |     | 155 |     |     |     |     | 160 |

| Ala | Glu | Thr | Ile | Leu | Asp | Asn | Ile | Thr | Gln | Gly | Thr | Gln | Ser | Phe | Asn |
|     |     |     |     | 165 |     |     |     |     | 170 |     |     |     |     | 175 |     |

| Asp | Phe | Thr | Arg | Val | Val | Gly | Gly | Glu | Asp | Ala | Lys | Pro | Gly | Gln | Phe |
|     |     |     | 180 |     |     |     |     | 185 |     |     |     |     | 190 |     |     |

| Pro | Trp | Gln | Val | Val | Leu | Asn | Gly | Lys | Val | Asp | Ala | Phe | Cys | Gly | Gly |
|     |     | 195 |     |     |     |     | 200 |     |     |     |     | 205 |     |     |     |

| Ser | Ile | Val | Asn | Glu | Lys | Trp | Ile | Val | Thr | Ala | Ala | His | Cys | Val | Glu |
|     | 210 |     |     |     |     | 215 |     |     |     |     | 220 |     |     |     |     |

| Thr | Gly | Val | Lys | Ile | Thr | Val | Val | Ala | Gly | Glu | His | Asn | Ile | Glu | Glu |
| 225 |     |     |     |     | 230 |     |     |     |     | 235 |     |     |     |     | 240 |

| Thr | Glu | His | Thr | Glu | Gln | Lys | Arg | Asn | Val | Ile | Arg | Ile | Ile | Pro | His |
|     |     |     |     | 245 |     |     |     |     | 250 |     |     |     |     | 255 |     |

| His | Asn | Tyr | Asn | Ala | Ala | Ile | Asn | Lys | Tyr | Asn | His | Asp | Ile | Ala | Leu |
|     |     |     |     | 260 |     |     |     |     | 265 |     |     |     |     | 270 |     |

| Leu | Glu | Leu | Asp | Glu | Pro | Leu | Val | Leu | Asn | Ser | Tyr | Val | Thr | Pro | Ile |
|     |     |     | 275 |     |     |     |     | 280 |     |     |     |     | 285 |     |     |

| Cys | Ile | Ala | Asp | Lys | Glu | Tyr | Thr | Asn | Ile | Phe | Leu | Lys | Phe | Gly | Ser |
|     |     | 290 |     |     |     |     | 295 |     |     |     |     | 300 |     |     |     |

| Gly | Tyr | Val | Ser | Gly | Trp | Ala | Arg | Val | Phe | His | Lys | Gly | Arg | Ser | Ala |
| 305 |     |     |     |     | 310 |     |     |     |     | 315 |     |     |     |     | 320 |

| Leu | Val | Leu | Gln | Tyr | Leu | Arg | Val | Pro | Leu | Val | Asp | Arg | Ala | Thr | Cys |
|     |     |     |     | 325 |     |     |     |     | 330 |     |     |     |     | 335 |     |

```
Leu  Arg  Ser  Thr  Lys  Phe  Thr  Ile  Tyr  Asn  Asn  Met  Phe  Cys  Ala  Gly
               340                 345                          350

Phe  His  Glu  Gly  Gly  Arg  Asp  Ser  Cys  Gln  Gly  Asp  Ser  Gly  Gly  Pro
          355                      360                      365

His  Val  Thr  Glu  Val  Glu  Gly  Thr  Ser  Phe  Leu  Thr  Gly  Ile  Ile  Ser
     370                 375                      380

Trp  Gly  Glu  Glu  Cys  Ala  Met  Lys  Gly  Lys  Tyr  Gly  Ile  Tyr  Thr  Lys
385                      390                 395                           400

Val  Ser  Arg  Tyr  Val  Asn  Trp  Ile  Lys  Glu  Lys  Thr  Lys  Leu  Thr
                    405                      410                      415
```

(2) INFORMATION FOR SEQ ID NO:3:

(i) SEQUENCE CHARACTERISTICS:
    (A) LENGTH: 448 amino acids
    (B) TYPE: amino acid
    (D) TOPOLOGY: linear (ii) MOLECULE TYPE: protein (iii) HYPOTHETICAL: NO (iv) ANTI-SENSE: NO (ix) FEATURE:
    (A) NAME/KEY: Region
    (B) LOCATION: 1..139
    (D) OTHER INFORMATION: /note= "Factor X Light Chain"

(ix) FEATURE:
    (A) NAME/KEY: Region
    (B) LOCATION: 140..142
    (D) OTHER INFORMATION: /note= "Factor X Connecting
         Tripeptide"

(ix) FEATURE:
    (A) NAME/KEY: Region
    (B) LOCATION: 143..448
    (D) OTHER INFORMATION: /note= "Factor X Heavy Chain"

(xi) SEQUENCE DESCRIPTION: SEQ ID NO:3:

```
Ala  Asn  Ser  Phe  Leu  Glu  Glu  Met  Lys  Lys  Gly  His  Leu  Glu  Arg  Glu
1                   5                     10                          15

Cys  Met  Glu  Glu  Thr  Cys  Ser  Tyr  Glu  Glu  Ala  Arg  Glu  Val  Phe  Glu
               20                      25                      30

Asp  Ser  Asp  Lys  Thr  Asn  Glu  Phe  Trp  Asn  Lys  Tyr  Lys  Asp  Gly  Asp
          35                      40                      45

Gln  Cys  Glu  Thr  Ser  Pro  Cys  Gln  Asn  Gln  Gly  Lys  Cys  Lys  Asx  Gly
     50                      55                      60

Leu  Gly  Glu  Tyr  Thr  Cys  Thr  Cys  Leu  Glu  Gly  Phe  Glu  Gly  Lys  Asn
65                       70                      75                           80

Cys  Glu  Leu  Phe  Thr  Arg  Lys  Leu  Cys  Ser  Leu  Asp  Asn  Gly  Asp  Cys
               85                      90                           95

Asp  Gln  Phe  Cys  His  Glu  Glu  Gln  Asn  Ser  Val  Val  Cys  Ser  Cys  Ala
               100                     105                     110

Arg  Gly  Tyr  Thr  Leu  Ala  Asp  Asn  Gly  Lys  Ala  Cys  Ile  Pro  Thr  Gly
               115                     120                     125

Pro  Tyr  Pro  Cys  Gly  Lys  Gln  Thr  Leu  Glu  Arg  Arg  Lys  Arg  Ser  Val
     130                     135                     140

Ala  Gln  Ala  Thr  Ser  Ser  Ser  Gly  Glu  Ala  Pro  Asp  Ser  Ile  Thr  Trp
145                      150                     155                          160

Lys  Pro  Tyr  Asp  Ala  Ala  Asp  Leu  Asp  Pro  Thr  Glu  Asn  Pro  Phe  Asp
                    165                     170                     175
```

```
Leu Leu Asp Phe Asn Gln Thr Gln Pro Glu Arg Gly Asp Asn Asn Leu
        180                 185                 190

Thr Arg Ile Val Gly Gly Gln Glu Cys Lys Asp Gly Glu Cys Pro Trp
        195                 200                 205

Gln Ala Leu Leu Ile Asn Glu Glu Asn Glu Gly Phe Cys Gly Gly Thr
        210                 215                 220

Ile Leu Ser Glu Phe Tyr Ile Leu Thr Ala Ala His Cys Leu Tyr Gln
225                     230                 235                 240

Ala Lys Arg Phe Lys Val Arg Val Gly Asp Arg Asn Thr Glu Gln Glu
                245                 250                 255

Glu Gly Gly Glu Ala Val His Glu Val Glu Val Val Ile Lys His Asn
            260                 265                 270

Arg Phe Thr Lys Glu Thr Tyr Asp Phe Asp Ile Ala Val Leu Arg Leu
        275                 280                 285

Lys Thr Pro Ile Thr Phe Arg Met Asn Val Ala Pro Ala Cys Leu Pro
        290                 295                 300

Glu Arg Asp Trp Ala Glu Ser Thr Leu Met Thr Gln Lys Thr Gly Ile
305                     310                 315                 320

Val Ser Gly Phe Gly Arg Thr His Glu Lys Gly Arg Gln Ser Thr Arg
                325                 330                 335

Leu Lys Met Leu Glu Val Pro Tyr Val Asp Arg Asn Ser Cys Lys Leu
            340                 345                 350

Ser Ser Ser Phe Ile Ile Thr Gln Asn Met Phe Cys Ala Gly Tyr Asp
        355                 360                 365

Thr Lys Gln Glu Asp Ala Cys Gln Gly Asp Ser Gly Gly Pro His Val
        370                 375                 380

Thr Arg Phe Lys Asp Thr Tyr Phe Val Thr Gly Ile Val Ser Trp Gly
385                     390                 395                 400

Glu Gly Cys Ala Arg Lys Gly Lys Tyr Gly Ile Tyr Thr Lys Val Thr
                405                 410                 415

Ala Phe Leu Lys Trp Ile Asp Arg Ser Met Lys Thr Arg Gly Leu Pro
            420                 425                 430

Lys Ala Lys Ser His Ala Pro Glu Val Ile Thr Ser Ser Pro Leu Lys
        435                 440                 445
```

(2) INFORMATION FOR SEQ ID NO:4:

(i) SEQUENCE CHARACTERISTICS:
        (A) LENGTH: 579 amino acids
        (B) TYPE: amino acid
        (D) TOPOLOGY: linear (ii) MOLECULE TYPE: protein (iii) HYPOTHETICAL: NO (iv) ANTI-SENSE: NO (ix) FEATURE:
        (A) NAME/KEY: Region
        (B) LOCATION: 1..320
        (D) OTHER INFORMATION: /note= "Prothrombin Light Chain"

(ix) FEATURE:
        (A) NAME/KEY: Region
        (B) LOCATION: 321..579
        (D) OTHER INFORMATION: /note= "Prothrombin Heavy Chain"

(xi) SEQUENCE DESCRIPTION: SEQ ID NO:4:

```
Ala Asn Thr Phe Leu Glu Glu Val Arg Lys Gly Asn Leu Glu Arg Glu
1                   5                   10                  15
```

| | | | | | | | | | | | | | | |
|---|---|---|---|---|---|---|---|---|---|---|---|---|---|---|
|Cys|Val|Glu|Glu 20|Thr|Cys|Ser|Tyr|Glu 25|Glu|Ala|Phe|Glu|Ala 30|Leu|Glu|
|Ser|Ser|Thr 35|Ala|Thr|Asp|Val|Phe 40|Trp|Ala|Lys|Tyr|Thr 45|Ala|Cys|Glu|
|Thr|Ala 50|Arg|Thr|Pro|Arg|Asp 55|Lys|Leu|Ala|Ala|Cys 60|Leu|Glu|Gly|Asn|
|Cys 65|Ala|Glu|Gly|Leu|Gly 70|Thr|Asn|Tyr|Arg|Gly 75|His|Val|Asn|Ile|Thr 80|
|Arg|Ser|Gly|Ile|Glu 85|Cys|Gln|Leu|Trp|Arg 90|Ser|Arg|Tyr|Pro|His|Lys 95|
|Pro|Glu|Ile|Asn 100|Ser|Thr|Thr|His|Pro 105|Gly|Ala|Asp|Leu|Gln 110|Glu|Asn|
|Phe|Cys|Arg 115|Asn|Pro|Asp|Ser|Ser 120|Asn|Thr|Gly|Pro|Trp 125|Cys|Tyr|Thr|
|Thr|Asp 130|Pro|Thr|Val|Arg|Arg 135|Gln|Glu|Cys|Ser|Ile 140|Pro|Val|Cys|Gly|
|Gln 145|Asp|Gln|Val|Thr|Val 150|Ala|Met|Thr|Pro|Arg 155|Ser|Glu|Gly|Ser|Ser 160|
|Val|Asn|Leu|Ser|Pro 165|Pro|Leu|Glu|Gln|Cys 170|Val|Pro|Asp|Arg|Gly 175|Gln|
|Gln|Tyr|Gln|Gly 180|Arg|Leu|Ala|Val|Thr 185|Thr|His|Gly|Leu|Pro 190|Cys|Leu|
|Ala|Trp|Ala 195|Ser|Ala|Gln|Ala|Lys 200|Ala|Leu|Ser|Lys|His 205|Gln|Asp|Phe|
|Asn|Ser 210|Ala|Val|Gln|Leu|Val 215|Glu|Asn|Phe|Cys|Arg 220|Asn|Pro|Asp|Gly|
|Asp 225|Glu|Glu|Gly|Val|Trp 230|Cys|Tyr|Val|Ala|Gly 235|Lys|Pro|Gly|Asp|Phe 240|
|Gly|Tyr|Cys|Asp|Leu 245|Asn|Tyr|Cys|Glu|Glu 250|Ala|Val|Glu|Glu|Glu 255|Thr|
|Gly|Asp|Gly|Leu 260|Asp|Glu|Asp|Ser|Asp 265|Arg|Ala|Ile|Glu|Gly 270|Arg|Thr|
|Ala|Thr|Ser 275|Glu|Tyr|Gln|Thr|Phe 280|Phe|Asn|Pro|Arg|Thr 285|Phe|Gly|Ser|
|Gly|Glu 290|Ala|Asp|Cys|Gly|Leu 295|Arg|Pro|Leu|Phe|Glu 300|Lys|Lys|Ser|Leu|
|Glu 305|Asp|Lys|Thr|Glu|Arg 310|Glu|Leu|Leu|Glu|Ser 315|Tyr|Ile|Asp|Gly|Arg 320|
|Ile|Val|Glu|Gly|Ser 325|Asp|Ala|Glu|Ile|Gly 330|Met|Ser|Pro|Trp|Gln 335|Val|
|Met|Leu|Phe|Arg 340|Lys|Ser|Pro|Gln|Glu 345|Leu|Leu|Cys|Gly|Ala 350|Ser|Leu|
|Ile|Ser|Asp 355|Arg|Trp|Val|Leu|Thr 360|Ala|Ala|His|Cys|Leu 365|Leu|Tyr|Pro|
|Pro|Trp 370|Asp|Lys|Asn|Phe|Thr 375|Glu|Asn|Asp|Leu|Leu 380|Val|Arg|Ile|Gly|
|Lys 385|His|Ser|Arg|Thr|Arg 390|Tyr|Glu|Arg|Asn|Ile 395|Glu|Lys|Ile|Ser|Met 400|
|Leu|Glu|Lys|Ile|Tyr 405|Ile|His|Pro|Arg|Tyr 410|Asn|Trp|Arg|Glu|Asn 415|Leu|
|Asp|Arg|Asp|Ile 420|Ala|Leu|Met|Lys|Leu 425|Lys|Lys|Pro|Val|Ala 430|Phe|Ser|
|Asp|Tyr|Ile|His|Pro|Val|Cys|Leu|Pro|Asp|Arg|Glu|Thr|Ala|Ala|Ser|

-continued

```
                435                        440                        445
    Leu  Leu  Gln  Ala  Gly  Tyr  Lys  Gly  Arg  Val  Thr  Gly  Trp  Gly  Asn  Leu
         450                      455                      460
    Lys  Glu  Thr  Trp  Thr  Ala  Asn  Val  Gly  Lys  Gly  Gln  Pro  Ser  Val  Leu
    465                      470                      475                      480
    Gln  Val  Val  Asn  Leu  Pro  Ile  Val  Glu  Arg  Pro  Val  Cys  Lys  Asp  Ser
                        485                      490                      495
    Thr  Arg  Ile  Arg  Ile  Thr  Asp  Asn  Met  Phe  Cys  Ala  Gly  Tyr  Lys  Pro
                   500                      505                      510
    Asp  Glu  Gly  Lys  Arg  Gly  Asp  Ala  Cys  Glu  Gly  Asp  Ser  Gly  Gly  Pro
                   515                      520                      525
    Phe  Val  Met  Lys  Ser  Pro  Phe  Asn  Asn  Arg  Trp  Tyr  Gln  Met  Gly  Ile
         530                      535                      540
    Val  Ser  Trp  Gly  Glu  Gly  Cys  Asp  Arg  Asp  Gly  Lys  Tyr  Gly  Phe  Tyr
    545                      550                      555                      560
    Thr  His  Val  Phe  Arg  Leu  Lys  Lys  Trp  Ile  Gln  Lys  Val  Ile  Asp  Gln
                        565                      570                      575
    Phe  Gly  Glu
```

( 2 ) INFORMATION FOR SEQ ID NO:5:

( i ) SEQUENCE CHARACTERISTICS:
  ( A ) LENGTH: 406 amino acids
  ( B ) TYPE: amino acid
  ( D ) TOPOLOGY: linear ( i i ) MOLECULE TYPE: protein ( i i i ) HYPOTHETICAL: NO ( i v ) ANTI-SENSE: NO ( i x ) FEATURE:
  ( A ) NAME/KEY: Region
  ( B ) LOCATION: 1..152
  ( D ) OTHER INFORMATION: /note= "Factor VII Light Chain"

( i x ) FEATURE:
  ( A ) NAME/KEY: Region
  ( B ) LOCATION: 153..406
  ( D ) OTHER INFORMATION: /note= "Factor VII Heavy Chain"

( x i ) SEQUENCE DESCRIPTION: SEQ ID NO:5:

```
    Ala  Asn  Ala  Phe  Leu  Glu  Glu  Leu  Arg  Pro  Gly  Ser  Leu  Glu  Arg  Glu
    1              5                        10                       15
    Cys  Lys  Glu  Glu  Gln  Cys  Ser  Phe  Glu  Glu  Ala  Arg  Glu  Ile  Phe  Lys
                   20                       25                       30
    Asp  Ala  Glu  Arg  Thr  Lys  Leu  Phe  Trp  Ile  Ser  Tyr  Ser  Asp  Gly  Asp
              35                       40                       45
    Gln  Cys  Ala  Ser  Ser  Pro  Cys  Gln  Asn  Gly  Gly  Ser  Cys  Lys  Asp  Gln
         50                       55                       60
    Leu  Gln  Ser  Tyr  Ile  Cys  Phe  Cys  Leu  Pro  Ala  Phe  Glu  Gly  Arg  Asn
    65                       70                       75                       80
    Cys  Glu  Thr  His  Lys  Asp  Asp  Gln  Leu  Ile  Cys  Val  Asn  Glu  Asn  Gly
                        85                       90                       95
    Gly  Cys  Glu  Gln  Tyr  Cys  Ser  Asp  His  Thr  Gly  Thr  Lys  Arg  Ser  Cys
                   100                      105                      110
    Arg  Cys  His  Glu  Gly  Tyr  Ser  Leu  Leu  Ala  Asp  Gly  Val  Ser  Cys  Thr
              115                      120                      125
    Pro  Thr  Val  Glu  Tyr  Pro  Cys  Gly  Lys  Ile  Pro  Ile  Leu  Glu  Lys  Arg
         130                      135                      140
```

```
Asn  Ala  Ser  Lys  Pro  Gln  Gly  Arg  Ile  Val  Gly  Gly  Lys  Val  Cys  Pro
145                 150                           155                      160

Lys  Gly  Glu  Cys  Pro  Trp  Gln  Val  Leu  Leu  Leu  Val  Asn  Gly  Ala  Gln
               165                      170                      175

Leu  Cys  Gly  Gly  Thr  Leu  Ile  Asn  Thr  Ile  Trp  Val  Val  Ser  Ala  Ala
               180                 185                      190

His  Cys  Phe  Asp  Lys  Ile  Lys  Asn  Trp  Arg  Asn  Leu  Ile  Ala  Val  Leu
          195                 200                      205

Gly  Glu  His  Asp  Leu  Ser  Glu  His  Asp  Gly  Asp  Glu  Gln  Ser  Arg  Arg
     210                      215                      220

Val  Ala  Gln  Val  Ile  Ile  Pro  Ser  Thr  Tyr  Val  Pro  Gly  Thr  Thr  Asn
225                      230                 235                           240

His  Asp  Ile  Ala  Leu  Leu  Arg  Leu  His  Gln  Pro  Val  Val  Leu  Thr  Asp
                    245                      250                      255

His  Val  Val  Pro  Leu  Cys  Leu  Pro  Glu  Arg  Thr  Phe  Ser  Glu  Arg  Thr
               260                 265                      270

Leu  Ala  Phe  Val  Arg  Phe  Ser  Leu  Val  Ser  Gly  Trp  Gly  Gln  Leu  Leu
          275                      280                 285

Asp  Arg  Gly  Ala  Thr  Ala  Leu  Glu  Leu  Met  Val  Leu  Asn  Val  Pro  Arg
     290                      295                      300

Leu  Met  Thr  Gln  Asp  Cys  Leu  Gln  Gln  Ser  Arg  Lys  Val  Gly  Asp  Ser
305                      310                 315                           320

Pro  Asn  Ile  Thr  Glu  Tyr  Met  Phe  Cys  Ala  Gly  Tyr  Ser  Asp  Gly  Ser
               325                      330                      335

Lys  Asp  Ser  Cys  Lys  Gly  Asp  Ser  Gly  Gly  Pro  His  Ala  Thr  His  Tyr
               340                      345                      350

Arg  Gly  Thr  Trp  Tyr  Leu  Thr  Gly  Ile  Val  Ser  Trp  Gly  Gln  Gly  Cys
               355                      360                      365

Ala  Thr  Val  Gly  His  Phe  Gly  Val  Tyr  Thr  Arg  Val  Ser  Gln  Tyr  Ile
     370                      375                      380

Glu  Trp  Leu  Gln  Lys  Leu  Met  Arg  Ser  Glu  Pro  Arg  Pro  Gly  Val  Leu
385                      390                      395                      400

Leu  Arg  Ala  Pro  Phe  Pro
                    405
```

( 2 ) INFORMATION FOR SEQ ID NO:6:

( i ) SEQUENCE CHARACTERISTICS:
        ( A ) LENGTH: 21 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:6:

```
Asn  Ala  Asn  Thr  Pro  Asp  Arg  Leu  Gln  Gln  Ala  Ser  Leu  Pro  Leu  Leu
1                   5                      10                      15

Ser  Asn  Thr  Asn  Cys
               20
```

( 2 ) INFORMATION FOR SEQ ID NO:7:

( i ) SEQUENCE CHARACTERISTICS:
    ( A ) LENGTH: 21 amino acids
    ( B ) TYPE: amino acid
    ( C ) STRANDEDNESS: single
    ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:7:

```
Gly  Thr  Ser  Tyr  Pro  Asp  Val  Leu  Lys  Cys  Leu  Lys  Ala  Pro  Ile  Leu
1                   5                        10                       15
Ser  Asp  Ser  Ser  Cys
                    20
```

( 2 ) INFORMATION FOR SEQ ID NO:8:

( i ) SEQUENCE CHARACTERISTICS:
    ( A ) LENGTH: 15 amino acids
    ( B ) TYPE: amino acid
    ( C ) STRANDEDNESS: single
    ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:8:

```
Val  Lys  Phe  Thr  Ile  Arg  Val  Phe  Asn  Pro  Arg  Asn  Leu  Lys  Ile
1                   5                        10                       15
```

( 2 ) INFORMATION FOR SEQ ID NO:9:

( i ) SEQUENCE CHARACTERISTICS:
    ( A ) LENGTH: 14 amino acids
    ( B ) TYPE: amino acid
    ( C ) STRANDEDNESS: single
    ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:9:

```
Met  His  Lys  Leu  Arg  Glu  Gly  Lys  Trp  Arg  Pro  Lys  Ser  Arg
1                   5                        10
```

( 2 ) INFORMATION FOR SEQ ID NO:10:

( i ) SEQUENCE CHARACTERISTICS:
    ( A ) LENGTH: 15 amino acids
    ( B ) TYPE: amino acid
    ( C ) STRANDEDNESS: single
    ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:10:

```
Pro Gly Val Tyr Ala Arg Val Thr Ala Leu Val Asn Trp Val Gln
1               5                   10                  15
```